US 11,512,351 B2

(12) United States Patent
Deng et al.

(10) Patent No.: US 11,512,351 B2
(45) Date of Patent: *Nov. 29, 2022

(54) ASSAY FOR PRE-OPERATIVE PREDICTION OF ORGAN FUNCTION RECOVERY

(71) Applicant: THE REGENTS OF THE UNIVERSITY OF CALIFORNIA, Oakland, CA (US)

(72) Inventors: Mario Deng, Venice, CA (US); Galyna Bondar, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/888,447

(22) Filed: May 29, 2020

(65) Prior Publication Data
US 2020/0291476 A1 Sep. 17, 2020

Related U.S. Application Data

(63) Continuation of application No. 16/028,369, filed on Jul. 5, 2018, now Pat. No. 10,704,093.
(Continued)

(51) Int. Cl.
*C12Q 1/6883* (2018.01)
*C12Q 1/6876* (2018.01)

(52) U.S. Cl.
CPC ......... *C12Q 1/6876* (2013.01); *C12Q 1/6883* (2013.01); *C12Q 2600/106* (2013.01); *C12Q 2600/158* (2013.01)

(58) Field of Classification Search
CPC ................ C12Q 1/6883; C12Q 1/6886; C12Q 2600/105; C12Q 2600/158
See application file for complete search history.

(56) References Cited

U.S. PATENT DOCUMENTS

| | | | |
|---|---|---|---|
| 10,704,093 B2 * | 7/2020 | Deng | C12Q 1/6883 |
| 2013/0330325 A1 * | 12/2013 | Grabe | G01N 33/5011 424/133.1 |

(Continued)

FOREIGN PATENT DOCUMENTS

| | | |
|---|---|---|
| WO | WO2010103388 A2 | 9/2010 |
| WO | WO2011063382 A1 | 5/2011 |
| WO | WO2012135841 A2 | 10/2012 |

OTHER PUBLICATIONS

Ma, H. et al. International Journal of Cancer 128:771-777 (2011; online Apr. 20, 2010). (Year: 2010).*

(Continued)

*Primary Examiner* — Diana B Johannsen
(74) *Attorney, Agent, or Firm* — Karen S. Canady; canady + lortz LLP

(57) ABSTRACT

Gene expression is measured in a sample of peripheral blood mononuclear cells (PBMCs) obtained from a subject and used to predict organ function recovery. A Function Recovery Potential (FRP) score is assigned to a sample that reflects the measured expression level of the genes identified herein in a direction associated with recovery from organ failure. Treatment of the subject with optimal medical management (OMM) and/or palliative care (PC) is advised when the FRP score is lower than the reference value, and referring the subject for treatment with therapies including—but not limited to—mechanical circulatory support (MCS) surgery, heart transplant (HTx) surgery, or other intervention for advanced heart failure is advised when the FRP score is greater than the reference value. A method for developing an FRP scoring algorithm that predicts a subject's ability to recover from medical intervention for organ failure is also described.

20 Claims, 11 Drawing Sheets
(6 of 11 Drawing Sheet(s) Filed in Color)
Specification includes a Sequence Listing.

Comparing Filtered 0.1 Mann-Whitney Test from improvement and 1-year survival outcome

| ENTREZ ID | Gene Symbol | Fold Change | GROUP I | GROUP II | p-value | p (corr) with FDR |
|---|---|---|---|---|---|---|
| 116071 | BATF2 | -2.2702124 | DOWN | UP | 0.0160601 | 0.0917301 |
| 375790 | AGRN | -2.2644913 | DOWN | UP | 0.0173365 | 0.0917301 |
| 118932 | ANKRD22 | -2.685126 | DOWN | UP | 0.0201359 | 0.0917301 |
| 196968 | DNM1P46 | -2.2071562 | DOWN | UP | 0.0073141 | 0.0917301 |
| 122786 | FRMD6 | -2.4180312 | DOWN | UP | 0.0028534 | 0.0917301 |
| 3805 | KIR2DL4 | -3.4912138 | DOWN | UP | 0.0036256 | 0.0917301 |
| 286554 | BCORP1 | -3.629981 | DOWN | UP | 0.0200527 | 0.0917301 |
| 100316904 | SAP25 | 2.371788 | UP | DOWN | 0.0069457 | 0.0917301 |
| 9476 | NAPSA | 2.1895349 | UP | DOWN | 0.0159894 | 0.0917301 |
| 80072 | HEXA-AS1 | 2.1215222 | UP | DOWN | 0.0186288 | 0.0917301 |
| 7078 | TIMP3 | 2.2165775 | UP | DOWN | 0.0200527 | 0.0917301 |
| 25807 | RHBDD3 | 2.2666128 | UP | DOWN | 0.0224032 | 0.098414 |

Related U.S. Application Data

(60) Provisional application No. 62/595,383, filed on Dec. 6, 2017, provisional application No. 62/528,748, filed on Jul. 5, 2017.

(56) References Cited

U.S. PATENT DOCUMENTS

| | | |
|---|---|---|
| 2014/0018255 A1 | 1/2014 | Galon |
| 2016/0186270 A1 | 6/2016 | Feron |

OTHER PUBLICATIONS

Defamie, V. et al. Oncogene 34:4098 (2015; online Oct. 27, 2014). (Year: 2014).*
Pelletier, S.J. et al. Liver Transpl. 15:859-868. (Year: 2009).*
Alvarado, Michael D et al. A prospective comparison of the 21-gene recurrence score and the PAM50-based prosigna in estrogen receptor-positive early-stage breast cancer. Adv Ther. 2015; 32:1237-1247.
Bao, Tra-Mi, et al. Association between Multidimensional Molecular Biomarkersand Functional Recovery Potential in Advanced Heart Failure. Journal of Heart and Lung Transplantation. Apr. 2018 vol. 37, Issue 4, Supplement, pp. S292-S293. Poster Presented at The International Society for Heart & Lung Transplantation—38th Annual Meeting and Scientific Sessions. Apr. 11, 2018. Nice, France.
Bondar, Galyna, et al. Association between preoperative peripheral blood mononuclear cell gene expression profiles, early postoperative organ function recovery potential and long-term survival in advanced heart failure patients undergoing mechanical circulatory support. PLoS ONE 12(12): e0189420. https://doi.org/10.1371/journal.pone.0189420. Published: Dec. 13, 2017.
Bondar, Galyna, et al. Comparison of Whole Blood and Peripheral Blood Mononuclear Cell Gene Expression for Evaluation of the Perioperative Inflammatory Response in Patients with Advanced Heart Failure. PLoS ONE 9(12):e115097. https://doi.org/10.1371/journal.pone.0115097. Published: Dec. 17, 2014.
Bondar, Galyna, et al. Systems Biological Identification of an Age-Related Predictor of Functional Recovery Potential in Advanced Heart Failure. The Journal of Heart and Lung Transplantation. vol. 37, Issue 4, Supplement, Apr. 2018, pp. S465-S466. Poster Presented at The International Society for Heart & Lung Transplantation—38th Annual Meeting and Scientific Sessions. Apr. 11, 2018. Nice, France.
Caredx, AlloMap—The Standard of Care for Managing Heart Transplant Recipients. LQ 10007R6.0. Retreived from www.caredxinc.com on May 16, 2018.
Caruso R, et al. Association of pre-operative interleukin-6 levels with Interagency Registry for Mechanically Assisted Circulatory Support profiles and intensive care unit stay in left ventricular assist device patients. J Heart Lung Transplant. 2012;31(6):625-33. [PMCID: 22386451].
Caruso R, et al. Eady expression of pro- and anti-inflammatory cytokines in left ventricular assist device recipients with multiple organ failure syndrome. Asaio J. 2010;56(4):313-8. [PMCID: 20445439].
Deng MC, et al. Impact of left ventricular dysfunction on cytokines, hemodynamics, and outcome in bypass grafting. Ann Thorac Surg. 1996;62(1):184-90. [PMCID: 8678641].
Deng MC, et al. Interleukin-6 correlates with hemodynamic impairment during dobutamine administration in chronic heart failure. Int J Cardiol. 1996;57(2):129-34. [PMCID: 9013264].
Deng MC, et al. Proinflammatory cytokines and cardiac pump function. Z Kardiol. 1997;86(10):788-802. [PMCID: 9454446].
Deng MC, et al. The relation of interleukin-6, tumor necrosis factor-alpha, IL-2, and IL-2 receptor levels to cellular rejection, allograft dysfunction, and clinical events early after cardiac transplantation. Transplantation. 1995;60(10):1118-24. [PMCID: 7482719].
Deng MC. The AlloMap™ genomic biomarker story: 10 years after. Clinical Transplantation. Mar. 1, 2017;31(3)e12900.
Deng, MC, et al. A peripheral blood transcriptome biomarker test to diagnose functional recovery potential in advanced heart failure. Biomark Med. Jun. 2018;12(6):619-635. doi: 10.2217/bmm-2018-0097. Epub May 8, 2018.
Deng, MC, et al. Multidimensional Molecular Biomarkers In Advanced Heart Failure—The MyLeukoMAPTM Rationale. 2016 Department of Medicine Research Day. Poster Presented Oct. 1, 2016.
Deng, MC, et al. Noninvasive discrimination of rejection in cardiac allograft recipients using gene expression profiling. Am J Transplant. Jan. 2006;6(1):150-60.
Detsky ME, et al. Discriminative Accuracy of Physician and Nurse Predictions for Survival and Functional Outcomes 6 Months After an ICU Admission. JAMA. 2017;317(21):2187-2195. doi:10.1001/jama.2017.4078.
ECRI Institute, Gene Expression Test (AlloMap) for Monitoring Heart Transplant Rejection, Nov. 2015.
Evans RW, et al. The Economic Implications of Noninvasive Molecular Testing for Cardiac Allograft Rejection. American Journal of Transplantation 2005; 5: 1553-1558.
Foster, Leonard J., et al. A Mammalian Organelle Map by Protein Correlation Profiling. Cell. Apr. 7, 2006;125(1):187-99.
Kaur K, et al. Biology of TNFalpha and IL-10, and their imbalance in heart failure. Heart Fail Rev. 2009;14(2):113-23. [PMCID: 18712475].
Levine B, et al. Elevated circulating levels of tumor necrosis factor in severe chronic heart failure. N Engl J Med. 1990;323(4):236-41. [PMCID: 2195340].
Mann DL. Inflammatory mediators and the failing heart: past, present, and the foreseeable future. Circ Res. 2002;91(11):988-98. [PMCID: 12456484].
Masukawa, et al. Early Postoperative Organ Function Recovery Potential and Long-Term Survival in Advanced Heart Failure Patients Undergoing Mechanical Circulatory Support. The Journal of Heart and Lung Transplantation. vol. 37, Issue 4, Supplement, Apr. 2018, p. S466. Poster Presented at The International Society for Heart & Lung Transplantation—38th Annual Meeting and Scientific Sessions. Apr. 11, 2018. Nice, France.
Ong MK, et al. Looking forward, looking back: assessing variations in hospital resource use and outcomes for elderly patients with heart failure. Circ Cardiovasc Qual Outcomes. 2009;2(6):548-57. [PMCID: 20031892].
Rittirsch D, et al. Harmful molecular mechanisms in sepsis. Nat Rev Immunol. 2008;8(10):776-87. [PMCID: 18802444].
Shah N, et al. National Trends in Utilization, Mortality, Complications, and Cost of Care After Left Ventricular Assist Device Implantation From 2005 to 2011. Ann Thorac Surg 2016;101:1477-84.
Shreibati JB, et al. Cost-effectiveness of left ventricular assist devices in ambulatory patients with advanced heart failure. JACC: Heart Failure. Feb. 28, 2017;5(2):110-9.
Sinha et al. Peripheral blood mononuclear cell transcriptome profiles suggest T-cell immunosuppression after uncomplicated mechanical circulatory support device surgery. Human Immunology. 2010; 71:164-169.
Soejima H, et al. Osteopontin expression of circulating T cells and plasma osteopontin levels are increased in relation to severity of heart failure. Circ J. 2007;71(12):1879-84. [PMCID: 18037740].
Togashi, Ryan, et al. Using a Non-supervised Network Analysis to Contextualize a 28 Predictive Gene Classifier Accessing Functional Recovery Potential of Patients Undergoing Mechanical Support. The Journal of Heart and Lung Transplantation. vol. 37, Issue 4, Supplement, Apr. 2018, p. S217. Poster Presented at The International Society for Heart & Lung Transplantation—38th Annual Meeting and Scientific Sessions. Apr. 11, 2018. Nice, France.
Turnbull AE, et al. Intensivist-reported facilitators and barriers to discussing post-discharge outcomes with intensive care unit surrogates: a qualitative study. Ann Am Thorac Soc. 2016;13(9):1546-1552.
Vincent JL, et al. Sepsis definitions: time for change. Lancet 2013; 381: 774-75.
Welch HG, et al. Income and Cancer Overdiagnosis—When Too Much Care Is Harmful. New England Journal of Medicine. Jun. 8, 2017;376(23):2208-9.
Wisniewski, Nicholas, et al. An integrative model of leukocyte genomics and organ dysfunction in heart failure patients requiring

(56) References Cited

OTHER PUBLICATIONS mechanical circulatory support. bioRxIV. https://doi.org/10.1101/024646. Published Aug. 14, 2015.

Wisniewski, Nicholas, et al. Integrative model of leukocyte genomics and organ dysfunction in heart failure patients requiring mechanical circulatory support: a prospective observational study. Wisniewski et al. BMC Medical Genomics (2017) 10:52. DOI 10.1186/s12920-017-0288-8.

Bassat et al., The extracellular matrix protein Agrin promotes heart regeneration in mice. Nature, Jul. 13, 2017, vol. 647, No. 7662, pp. 179-184. Abstract.

Cao et at., Identification of novel biomarkers in plasma for prediction of treatment response in patients with heart failure. Lancet, Feb. 26, 2015, vol. 385 (suppl 1 ), p. S26. Abstract.

Cho et al., Molecular evidence of stress-induced acute heart injury in a mouse model simulating posttraumatic stress disorder. PNAS, Feb. 25, 2014, vol. 111, No. 8, pp. 3188-3193. Abstract.

Chowdhury et al., Expression of fibulin-6 in failing hearts and its role for cardiac fibroblast migration. Cardiovascular Research, Jun. 20, 2014, vol. 103, No. 4, pp. 509-520. Abstract.

Kashiwagi et al., Expression of SGL T1 in Human Hearts and Impairment of Cardiac Glucose Uptake by Phlorizin during Ischemia-Reperfusion injury in Mice. PLOS ONE, Jun. 29, 2015, vol. 10, No. 6, pp. 1-17, e0130605. Abstract.

Klena et al., Role of Cilia and Left-Right Patterning in Congenital Heart Disease. Etiology and Morphogenesis of Congenital Heart Disease. Springer, Tokyo, Jun. 25, 2016, pp. 67-79. Abstract.

Liu et al., Activin receptor-like kinase 7 mediates high glucose-induced H9c2 cardiomyoblast apoptosis through activation of Smad2/3. The International Journal of Biochemistry & Cell Biology, Jul. 2, 2013, vol. 45, No. 9, pp. 2027-2035. Abstract.

Logue et al., An analysis of gene expression in PTSD implicates genes involved in the glucocorticoid receptor pathway and neural responses to stress. Psychoneuroendocrinology, Jul. 2015, vol. 57, pp. 1-13. Abstract.

Mazitov et al., Deficit in emotional learning in neurotrimin knock-out mice. Behavioural Brain Research, Sep. 28, 2016, vol. 317, pp. 311-318. Abstract; p. 311, col. 1, para 1.

Pan J et al., JAK2-Centered Interactome Hotspot Identified by an Integrative Network Algorithm in Acute Stanford Type A Aortic Dissection. PLOS ONE, Feb. 24, 2014, vol. 9, No. 2, pp. 1-9, e89406. Abstract; p. 2, col. 1, para 2; p. 4, col. 1, last para.

Perez et al., MAP17 and SGLT1 protein expression levels as prognostic markers for cervical tumor patient survival. PLOS ONE, Feb. 13, 2013, vol. 8, No. 2, pp. 1-10, e56169. Abstract; p. 1, col. 1, para 1.

Toriyama et al., The ciliopathy-associated CPLANE proteins direct basal body recruitment of intraflagellar transport machinery. Nature Genetics, Jun. 2016, vol. 48, No. 6, pp. 648-656. Abstract; p. 649, col. 2, para 2; p. 653, col. 2, para 2.

International Search Report and Written Opinion dated Nov. 29, 2018, for PCT/US18/40961 filed Jul. 5, 2018.

Bouras, G. et al. Medicinal Chemistry 10(7):682-699. (Year: 2014).

Iyalomhe, O. et al. Experimental Gerontology 69:159-169 (Sep. 2015).

Chen, C. et al. Cancer Biology & Therapy 16:856 (Jun. 2015).

Heidecker, Bettina, et al., Transcriptomic biomarkers for individual risk assessment in new-onset heart failure, Circulation. Jul. 15, 2008;118(3):238-46. doi: 10.1161/Circulationaha.107.756544. Epub Jun. 30, 2008.

Kim, Jinhee, et al., Gene expression profiles associated with acute myocardial infarction and risk of cardiovascular death, Genome Medicine vol. 6, Article No. 40 (2014).

Extended European Search Report dated Feb. 22, 2021, for corresponding European Application No. 18828712.2 (EP3649250).

\* cited by examiner

Comparing Filtered 0.1 Mann-Whitney Test from improvement and 1-year survival outcome

| ENTREZ ID | Gene Symbol | Fold Change | GROUP I | GROUP II | p-value | p (corr) with FDR |
|---|---|---|---|---|---|---|
| 116071 | BATF2 | -2.2702124 | DOWN | UP | 0.0160601 | 0.0917301 |
| 375790 | AGRN | -2.2644913 | DOWN | UP | 0.0173365 | 0.0917301 |
| 118932 | ANKRD22 | -2.685126 | DOWN | UP | 0.02201359 | 0.0917301 |
| 196968 | DNM1P46 | -2.2071562 | DOWN | UP | 0.0073141 | 0.0917301 |
| 122786 | FRMD6 | -2.4180312 | DOWN | UP | 0.0028534 | 0.0917301 |
| 3805 | KIR2DL4 | -3.4912138 | DOWN | UP | 0.0036256 | 0.0917301 |
| 286554 | BCORP1 | -3.629981 | DOWN | UP | 0.0200527 | 0.0917301 |
| 100316904 | SAP25 | 2.371788 | UP | DOWN | 0.0069457 | 0.0917301 |
| 9476 | NAPSA | 2.1895149 | UP | DOWN | 0.0159894 | 0.0917301 |
| 80072 | HEXA-AS1 | 2.1215222 | UP | DOWN | 0.0186288 | 0.0917301 |
| 7078 | TIMP3 | 2.2165775 | UP | DOWN | 0.0200527 | 0.0917301 |
| 25807 | RHBDD3 | 2.2666128 | UP | DOWN | 0.0224032 | 0.0984414 |

ASSAY FOR PRE-OPERATIVE PREDICTION OF ORGAN FUNCTION RECOVERY

This application claims benefit of United States provisional patent application no. 62/528,748, filed Jul. 5, 2017, and 62/595,383, filed Dec. 6, 2017, the entire contents of each of which are incorporated by reference into this application.

ACKNOWLEDGEMENT OF GOVERNMENT SUPPORT

This invention was made with Government support under HL120040, awarded by the National Institutes of Health. The Government has certain rights in the invention.

REFERENCE TO A SEQUENCE LISTING SUBMITTED VIA EFS-WEB

The content of the ASCII text file of the sequence listing named "UCLA253_seq" which is 3 kb in size was created on Jul. 4, 2018, and electronically submitted via EFS-Web herewith the application is incorporated herein by reference in its entirety.

BACKGROUND OF THE INVENTION

In the United States, heart failure (HF) affects 6 million persons (Yancy 2013). HF with reduced ejection fraction (HFrEF) and HF with preserved ejection fraction (HFpEF) each affect 3 million people. The lifetime risk of developing HF is 1 in 5 for men and women older than 40 years of age. The death rate remains unacceptably high at approximately 50% within 5 years from the time of index diagnosis. In the US, an annually estimated 300,000 persons are diagnosed with Stage D heart failure, also classified as advanced heart failure (AdHF) (Hunt 2009).

SUMMARY OF THE INVENTION

Described herein are methods and systems for treating a cardiovascular disease. In some embodiments, described herein are methods and systems for predicting a prognosis of an individual with a cardiovascular disease following the provision of a treatment to that individual. In some embodiments, a prognosis of an individual following the provision of a treatment to the individual is provided a score. In some embodiments, a treatment modality for an individual is selected based on the score provided to the prognosis of the individual.

A large subgroup of patients with cardiovascular disease are patients with heart failure (HF). Heart failure (HF) is a complex clinical syndrome that causes systemic hypo-perfusion and failure to meet the body's metabolic demands. In an attempt to compensate, chronic upregulation of the sympathetic nervous system and renin-angiotensin-aldosterone leads to further myocardial injury, HF progression and reduced O2-delivery. This triggers progressive organ dysfunction, immune system activation and profound metabolic derangements, creating a milieu similar to other chronic systemic diseases and presenting as advanced HF (AdHF) with severely limited prognosis.

In general, patients with AdHF may benefit from various surgical/interventional therapies such as mechanical circulatory support (MCS) surgery, heart transplant (HTx) surgery, coronary artery bypass graft (CABG) surgery, percutaneous coronary interventions (PCI), aortic valve replacement (AVR) surgery, mitral valve replacement (MVR) surgery, trans-catheter aortic valve replacement (TAVR), transcatheter mitral valve clip, ventricular tachycardia ablation, or stellate gangliectomy in lieu of optimal medical management (OMM) or palliative/hospice care (PC). While the Stage C HF guideline-based medical therapy is well established, the survival benefit of these surgical/interventional therapeutic interventions is not as well established.

We hypothesize that 1-year survival in AdHF after these surgical/interventional therapies is linked to Functional Recovery Potential (FRP), a novel clinical composite parameter that includes HF severity, secondary organ dysfunction, comorbidities, frailty, and disabilities as well as chronological age and that can be diagnosed by a molecular immunological biomarker.

HF is a major public health concern due to its tremendous societal and economic burden, with estimated direct and indirect cost in the U.S. of $37.2 billion in 2009, which is expected to increase to $97 billion by 2030 (Roger 2012). While 25% of all spending occurs during the last year of life (Orszag 2008, Zhang 2009) in patients hospitalized with HF, more resource spending is associated with lower mortality rates (Ong 2009). A key consideration is: Which of these AdHF surgical/interventional therapies does a healthcare provider recommend to the individual AdHF-patient in order to tailor personal benefits in the most cost-effective way?

Across the different AdHF-interventions, the 1-year mortality rate is in the range of 10-30% (Deng 2018). This ambiguity suggests unpredictability of clinical trajectories, even with current clinical prediction tools tailored to the progressive clinical trajectory of HF severity and HF-related organ dysfunction (OD). Such models include Brain Natriuretic Peptide (BNP) measurements (Troughton 2000, Gardner 2003, Doust 2003), the Heart Failure Survival Score (HFSS) (Aaronson 1997), Seattle Heart Failure Model (Levy 2006, Ketchum 2010), MAGGIC score (Sartipy 2014), Frailty Scores (Martinez-Selles 2009, Flint 2012), INTERMACS Score (Smits 2013, Kirklin 2014), UCLA score (Chyu 2014), Sequential Organ Failure Assessment (SOFA) Score (Vincent 1996), HeartMate II risk score (Cowger 2013), Model of End-stage Liver Disease (Matthews 2010), Model of End-stage Liver Disease Except INR (MELD-X1) Score (Abe 2014) and right ventricular failure score (Kormos 2010). However, most validated prediction tools have the tendency to underestimate risk among the most severely ill patients. (Sartipy 2014). The uncertainty of predicting Stage D HF or AdHF-progression has an impact on individual patients' health and healthcare costs.

There remains a need for an improved prediction of risk associated with each of the above treatment options for heart failure, and ultimately an improved prediction of risk reduction when choosing one treatment option over another treatment option, i.e. an improved prediction of comparative survival benefit from the above interventions in AdHF-patients.

In some embodiments, the materials and methods described herein address these needs and more by using gene expression profiles to predict organ function recovery. Described herein is, in a representative embodiment, a method of measuring gene expression in a sample of peripheral blood mononuclear cells (PBMCs) obtained from a subject. The method can also be implemented as a method of predicting treatment outcome for advanced organ failure, such as advanced heart failure, and as a method of treating and/or a method of optimizing treatment of such organ failure. In some embodiments, the method comprises (a) measuring the expression level of a set of at least 8 genes in the sample, wherein the at least 8 genes are selected from those listed in Tables 2 and Table 3; (b) assigning a Function Recovery Potential (FRP) score to the sample that reflects the measured expression level of the genes in a direction associated with recovery from organ failure, wherein the FRP score corresponds to the measured expression level of the set of genes relative to a reference value. In some embodiments, the subject is suffering from heart failure. Optionally, the method further comprises (c) treating the subject with optimal medical management (OMM) and/or palliative care (PC) when the FRP score is lower than the reference value, and referring the subject for treatments including—but not limited to—mechanical circulatory support (MCS) surgery, heart transplant (HTx) surgery, coronary artery bypass graft (CABG) surgery, percutaneous coronary interventions (PCI), aortic valve replacement (AVR) surgery, mitral valve replacement (MVR) surgery, trans-catheter aortic valve replacement (TAVR), transcatheter mitral clip, ventricular tachycardia ablation, or stellate gangliectomy when the FRP score is greater than the reference value. In some embodiments, the expression level of 10-75 genes is measured. Alternatively, the expression level of 10-30 genes is measured. In other embodiments, the expression level of 10-15 genes is measured. In some embodiments, the set of genes is at least 10 of the genes listed in Table 2, at least 10 of the genes listed in Table 3 or at least 10 of the genes listed in Table 4, or comprises one gene selected from each of Tables 1A-1I. Optionally, the method further comprises measuring one or more control genes.

In some embodiments, the reference value corresponds to expression levels of the set of genes observed in subjects who recover from heart failure and/or major organ dysfunction. In one embodiment (see Bondar 2017), the reference value is constituted by averaging the GEP values across the 28 genes identified after 1) creating a dichotomous phenotype framework defined as Group I (High FRP=17 HF-patients who had a good functional recovery, as defined by improvement of Sequential Organ Failure Assessment (SOFA) score and Model of Endstage Liver Disease except INR (MELD-XI) score on day 8 after MCS surgery in comparison to day −1 before MCS-surgery) versus Group II (Low FRP=12 patients how did not fulfill this clinical criterion), 2) filtering the entire set of mRNA transcripts (36,938) (20th-100th percentile), retaining of the resulting 26,571 entities only those with a fold change of at least 2.0 (123 transcripts) for statistical analysis with the unpaired Mann-Whitney test and Benjamini-Hochberg correction analysis (FDR=0.1), identifying 28 genes as differentially expressed between GROUP I and GROUP II on day −1 and 3) building a model using the support vector machine (SVM) algorithm by randomly selecting 20 samples out of 29 total, stratified by membership in Group I versus Group II. To test the model, the remaining 9 samples were stratified by membership in Group I or Group II. An average prediction accuracy of 93% (range: 78-100%) was achieved after re-running the stratified random selection model building process 25 times. Thus, for any new HF-patient's blood sample with an unknown level of gene expression in the 28 genes listed in Table 3, the imputation of expression value of the 28 genes yields a dichotomous decision whether this sample is to be allocated to Group I or Group II with an accuracy of 93% and therefore allows with an accuracy of 93% to predict before the scheduled HF-=intervention whether this new HF-patient has a high FRP (GROUP I) or low FRP (GROUP II) (see two patient examples in FIG. 8). With this information added to the other clinical data available to this patient's doctor, the doctor can make a more precisely informed recommendation to the patient about whether or not to undergo the scheduled HF-intervention. In some embodiments such as the example above, the subject is suffering from HF and the method comprises (c) treating the subject with optimal medical management (OMM) and/or palliative care (PC) when the FRP score is low and referring the subject for treatments including—but not limited to—mechanical circulatory support (MCS) surgery, heart transplant (HTx) surgery, coronary artery bypass graft (CABG) surgery, percutaneous coronary interventions (PCI), aortic valve replacement (AVR) surgery, mitral valve replacement (MVR) surgery, trans-catheter aortic valve replacement (TAVR), transcatheter mitral clip, ventricular tachycardia ablation, or stellate gangliectomy when the FRP is high. In other embodiments, the expression level of 10-30 genes is measured. In some embodiments, the set of genes is at least 10 of the genes listed in Table 2, at least 10 of the genes listed in Table 3 or at least 10 of the genes listed in Table 4A and 4B, or comprises one gene selected from each of Tables 1A-1I. In some embodiments, the reference value corresponds to expression levels of the set of genes observed in subjects who recover from heart failure and/or major organ dysfunction. Optionally, the method further comprises measuring one or more control genes.

In one representative embodiment, the FRP score is between 1 (lowest) and 10 (highest), and the reference value is 5.5. The treating of step (c) comprises treating the subject with optimal medical management (OMM) and/or palliative care (PC) when the FRP score is 5 or less, and treating the subject with mechanical circulatory support (MCS) surgery, heart transplant (HTx) surgery, coronary artery bypass graft (CABG) surgery, percutaneous coronary interventions (PCI), aortic valve replacement (AVR) surgery, mitral valve replacement (MVR) surgery, trans-catheter aortic valve replacement (TAVR), transcatheter mitral clip, ventricular tachycardia ablation, or stellate gangliectomy when the FRP score is 6 to 10. In some embodiments, the lower scores are assigned to "Group II", while the higher scores are assigned to "Group I". In some embodiments, scores of 1-4 are assigned to Group II, while scores of 7-10 are assigned to Group I, and scores of 5-6 are considered an indeterminate zone, to be evaluated with additional circumstances taken into account, such as factors that weigh in favor of palliative care or factors that favor aggressive treatment, notwithstanding the less convincing FRP score.

In some embodiments, the measuring comprises polymerase chain reaction (PCR) or next generation sequencing (NGS). In some embodiments, the PCR is performed using one or more primers selected from GAPDH-f: CCACTCCTCCACCTTTGAC (SEQ ID NO: 1); GAPDH-r: ACCCTGTTGCTGTAGCCA (SEQ ID NO: 2); KIR2DL4-f: ACCCACTGCCTGTTTCTGTC (SEQ ID NO: 3); KIR2DL4-r: ATCACAGCATGCAGGTGTCT (SEQ ID NO: 4); NAPSA-f: CAGGACACCTGGGTTCACAC (SEQ ID NO: 5); NAPSA-r: GGTTGGACTCGATGAAGAGG (SEQ ID NO: 6); BATF2-f: AAAGGCAGCTGAAGAAGCAG (SEQ ID NO: 7); BATF2-r: TCTTTTTCCAGAGACTCGTGC (SEQ ID NO: 8); ANKRD22-f: CTCAGCCAGGAAGGATTTG (SEQ ID NO: 9); ANKRD22-r: TGATAGGCTGCTTGGCAGAT (SEQ ID NO: 10).

In some embodiments, the measuring is performed one to three days, or 72 hours, prior to treatment with an AdHF intervention. In one embodiment, the measuring is performed one day prior to treatment. In some embodiments, the subject is suffering from heart failure with reduced ejection fraction or preserved ejection fraction.

Also provided is a method of predicting outcome of AdHF intervention in a patient suffering from heart failure. The method typically comprises performing the method of measuring gene expression in a sample as described herein, wherein a poor outcome is predicted when the FRP score is greater than the reference value. Optionally, the method further comprises treating the subject with OMM, PC, MCS, HTx, or other AdHF intervention when the FRP score is less than the reference value.

Additionally provided is a method of monitoring progression of heart failure in a subject. In one embodiment, the method comprises performing the method of measuring gene expression in a sample as described herein. In a typical embodiment, progression is detected when the FRP score is reduced relative to a prior measurement obtained from the subject. In one embodiment, progression is detected when the FRP score is reduced by 2 (on a scale of 1-10) relative to a prior measurement.

In some embodiments, the FRP score is determined on the basis of a linear discriminant analysis (LDA) of at least 10 of the 28 genes listed in Table 3 using preoperative and postoperative expression levels of the at least 10 genes observed in a population of patients treated with AdHF intervention, wherein the FRP score is adjusted by weighting the contribution of each of the genes in accordance with the linear discriminant analysis. In some embodiments, the FRP score is determined on the basis of a linear discriminant analysis (LDA) of at least 10 of the genes listed in Table 4A and 4B. The linear discriminant analysis can be based on expression levels of fewer than 10, or up to all 28 of the genes listed in Table 3. In some embodiments, the linear discriminant analysis is based on expression levels of fewer than 10, or up to all of the genes listed in Table 4A and 4B. In some embodiments, the analysis takes into account additional genes, such as those listed in Table 2, or identified elsewhere. Those skilled in the art will recognize that the analysis can be performed using additional data from a larger patient population. In some embodiments, the preoperative expression levels are obtained one to three days prior to treatment. In some embodiments, the postoperative expression levels are obtained 7-10 days, and typically 5-40 days, after treatment. Examples of treatment include, but are not limited to, mechanical circulatory support (MCS) surgery, heart transplant (HTx) surgery, coronary artery bypass graft (CABG) surgery, percutaneous coronary interventions (PCI), aortic valve replacement (AVR) surgery, mitral valve replacement (MVR) surgery, trans-catheter aortic valve replacement (TAVR), transcatheter mitral clip, ventricular tachycardia ablation, or stellate gangliectomy.

Also provided is a non-transitory computer-readable medium encoded with computer-executable instructions for performing the methods described herein (FIG. 2). In another embodiment, the invention provides a non-transitory computer-readable medium embodying at least one program that, when executed by a computing device comprising at least one processor, causes the computing device to perform one or more of the methods described herein. In some embodiments, the at least one program contains algorithms, instructions or codes for causing the at least one processor to perform the method(s). Likewise, the invention provides a non-transitory computer-readable storage medium storing computer-readable algorithms, instructions or codes that, when executed by a computing device comprising at least one processor, cause or instruct the at least one processor to perform a method described herein.

The invention also provides a method of treating a subject suffering from heart failure. In one embodiment, the method comprises (a) measuring the expression level of a set of at least 8 genes in the sample, wherein the at least 8 genes are selected from those listed in Tables 2 and Table 3; (b) assigning a Function Recovery Potential (FRP) score between 1 (lowest) and 10 (highest) to the sample that reflects the measured expression level of the genes in a direction associated with recovery from organ failure; and (c) treating the subject with optimal medical management (OMM) and/or palliative care (PC) when the FRP score 5 or less, and referring the subject for treatment with mechanical circulatory support (MCS) surgery, heart transplant (HTx) surgery, coronary artery bypass graft (CABG) surgery, percutaneous coronary interventions (PCI), aortic valve replacement (AVR) surgery, mitral valve replacement (MVR) surgery, trans-catheter aortic valve replacement (TAVR), transcatheter mitral clip, ventricular tachycardia ablation, or stellate gangliectomy when the FRP score is 6 to 10. In one embodiment, the set of genes is BATF2, AGRN, ANKRD22, DNM1P46, FRMD6, KIR2DL4, BCORP1, SAP25, NAPSA, HEXA-AS1, TIMP3, and RHBDD3.

Also described herein is a method for developing a function recovery potential (FRP) scoring algorithm that predicts a subject's ability to recover from medical intervention for organ failure. In one embodiment, the method comprises (a) obtaining the expression levels of at least 10 of the 28 genes listed in Table 3 or at least 10 of the genes listed in Table 4A and 4B using pre-intervention and post-intervention expression levels of the at least 10 genes observed in PBMC samples obtained from a population of patients treated with medical intervention for organ failure; (b) performing linear discriminant analysis of the expression levels obtained in (a) to classify the PBMC samples into Group I (post-intervention improvement) or Group II (non-improvement); (c) estimating the effect size of each of the gene expression levels on the classification of a sample into Group I or Group II; and (d) adjusting the FRP scoring algorithm by weighting the contribution of each of the genes in accordance with the effect size. In one embodiment, the medical intervention is surgery. In some embodiments, the surgery is an organ transplant, or provision of mechanical support for the organ, such as circulatory support or dialysis. In some embodiments, the AdHF intervention includes treatments—but is not limited to—mechanical circulatory support (MCS) surgery, heart transplant (HTx) surgery, coronary artery bypass graft (CABG) surgery, percutaneous coronary interventions (PCI), aortic valve replacement (AVR) surgery, mitral valve replacement (MVR) surgery, trans-catheter aortic valve replacement (TAVR), transcatheter mitral clip, ventricular tachycardia ablation, or stellate gangliectomy.

Also provided herein are methods for treating an individual, comprising: (i) receiving a sample from the individual; (ii) determining a gene expression level in the sample for at least one gene comprising RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, or FITM1; and (iii) providing a treatment to the individual based on the gene expression level. In some embodiments, the sample comprises blood, urine, sputum, hair, or skin. In some embodiments, the gene expression level is either an increase or a decrease in expression of the at least one gene relative to an expected expression level value. In some embodiments, the gene expression level in the sample that is determined is for two genes comprising RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, or FITM1. In some embodiments, the gene expression level is assigned a score, and wherein the treatment is determined based on the score. In some embodiments, the score comprises a Function Recovery Potential (FRP) score. In some embodiments, the score is determined based on a linear discriminant analysis of data comprising known gene expression levels and known FRP scores of a plurality of individuals. In some embodiments, the treatment is selected from—but not limited to—mechanical circulatory support (MCS) surgery, heart transplant (HTx) surgery, coronary artery bypass graft (CABG) surgery, percutaneous coronary interventions (PCI), aortic valve replacement (AVR) surgery, mitral valve replacement (MVR) surgery, trans-catheter aortic valve replacement (TAVR), transcatheter mitral clip, ventricular tachycardia ablation, or stellate gangliectomy. In some embodiments, the gene expression level is a level determined by polymerase chain reaction (PCR), next generation sequencing (NGS), or other gene expression profiling assay platform such as Nanostring's NCounter hybridization platform. In some embodiments, the PCR is performed using at least one primer selected from GAPDH-f: CCACTCCTC-CACCTTTGAC (SEQ ID NO: 1); GAPDH-r: ACCCTGTTGCTGTAGCCA (SEQ ID NO: 2); KIR2DL4-f: ACCCACTGCCTGTTTCTGTC (SEQ ID NO: 3); KIR2DL4-r: ATCACAGCATGCAGGTGTCT (SEQ ID NO: 4); NAPSA-f: CAGGACACCTGGGTTCACAC (SEQ ID NO: 5); NAPSA-r: GGTTGGACTCGATGAAGAGG (SEQ ID NO: 6); BATF2-f: AAAGGCAGCT-GAAGAAGCAG (SEQ ID NO: 7); BATF2-r: TCTTTTTCCAGAGACTCGTGC (SEQ ID NO: 8); ANKRD22-f: CTCAGCCAGGAAGGATTTTG (SEQ ID NO: 9); ANKRD22-r: TGATAGGCTGCTTGGCAGAT (SEQ ID NO: 10).

Further provided herein are computer implemented systems, comprising: (a) a sample receiver for receiving a sample provided by an individual; (b) a digital processing device comprising an operating system configured to perform executable instructions and a memory; (c) a computer program including instructions executable by the digital processing device to provide a treatment to a healthcare provider based on the sample, the computer program comprising: (i) an gene analysis module configured to determine a gene expression level in the sample for at least one gene comprising RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, or FITM1; (ii) a treatment determination module configured to determine the treatment based on the gene expression level; and (iii) a display module configured to provide the treatment to the healthcare provider. In some embodiments, the sample comprises blood, urine, sputum, hair, or skin. In some embodiments, the gene expression level is either an increase or a decrease in expression of the at least one gene relative to an expected expression level value. In some embodiments, the gene expression level in the sample that is determined is for two genes comprising RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, or FITM1. In some embodiments, the gene expression level is assigned a score. and wherein the treatment is determined based on the score. In some embodiments, the score comprises a Function Recovery Potential (FRP) score. In some embodiments, the score is determined based on a linear discriminant analysis of data comprising known gene expression levels and known FRP scores of a plurality of individuals. In some embodiments, the treatment is selected from mechanical circulatory support (MCS) surgery, heart transplant (HTx) surgery, coronary artery bypass graft (CABG) surgery, percutaneous coronary interventions (PCI), aortic valve replacement (AVR) surgery, mitral valve replacement (MVR) surgery, trans-catheter aortic valve replacement (TAVR), transcatheter mitral clip, ventricular tachycardia ablation, or stellate gangliectomy. In some embodiments, the gene expression level is a level determined by polymerase chain reaction (PCR), next generation sequencing (NGS), or other gene expression profiling assay platform such as Nanostring's NCounter hybridization platform. In some embodiments, the PCR is performed using at least one primer selected from GAPDH-f: CCACTCCTC-CACCTTTGAC (SEQ ID NO: 1); GAPDH-r: ACCCTGTTGCTGTAGCCA (SEQ ID NO: 2); KIR2DL4-f: ACCCACTGCCTGTTTCTGTC (SEQ ID NO: 3); KIR2DL4-r: ATCACAGCATGCAGGTGTCT (SEQ ID NO: 4); NAPSA-f: CAGGACACCTGGGTTCACAC (SEQ ID NO: 5); NAPSA-r: GGTTGGACTCGATGAAGAGG (SEQ ID NO: 6); BATF2-f: AAAGGCAGCT-GAAGAAGCAG (SEQ ID NO: 7); BATF2-r: TCTTTTTCCAGAGACTCGTGC (SEQ ID NO: 8); ANKRD22-f: CTCAGCCAGGAAGGATTTTG (SEQ ID NO: 9); ANKRD22-r: TGATAGGCTGCTTGGCAGAT (SEQ ID NO: 10).

Described herein is a Non-transitory computer-readable storage media encoded with a computer program including instructions executable by a processor to cause the processor to determine a gene expression level in a sample for at least one gene comprising RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, or FITM1; and provide a suggestion for a treatment to the individual based on the gene expression level. In some embodiments, the gene expression level is either an increase or a decrease in expression of the at least one gene relative to an expected expression level value. In some embodiments, the gene expression level in the sample that is determined is for two genes comprising RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, or FITM1. In some embodiments, the gene expression level is assigned a score, and wherein the treatment is determined based on the score. In some embodiments, the score comprises a Function Recovery Potential (FRP) score. In some embodiments, the score is determined based on a linear discriminant analysis of data comprising known gene expression levels and known FRP scores of a plurality of individuals. In some embodiments, the treatment is selected from mechanical circulatory support (MCS) surgery, heart transplant (HTx) surgery, coronary artery bypass graft (CABG) surgery, percutaneous coronary interventions (PCI), aortic valve replacement (AVR) surgery, mitral valve replacement (MVR) surgery, trans-catheter aortic valve replacement (TAVR), transcatheter mitral clip, ventricular tachycardia ablation, or stellate ganglicctomy. In some embodiments, the gene expression level is a level determined by polymerase chain reaction (PCR), next generation sequencing (NGS) or other platform such as Nanostring's NCounter hybridization platform. In some embodiments, the PCR is performed using at least one primer selected from GAPDH-f: CCACTCCTCCACCTTTGAC (SEQ ID NO: 1); GAPDH-r: ACCCTGTTGCTGTAGCCA (SEQ ID NO: 2); KIR2DL4-f: ACCCACTGCCTGTTTCTGTC (SEQ ID NO: 3); KIR2DL4-r: ATCACAGCATGCAGGTGTCT (SEQ ID NO: 4); NAPSA-f: CAGGACACCTGGGTTCACAC (SEQ ID NO: 5); NAPSA-r: GGTTGGACTCGATGAAGAGG (SEQ ID NO: 6); BATF2-f: AAAGGCAGCTGAAGAAGCAG (SEQ ID NO: 7); BATF2-r: TCTTTTTCCAGAGACTCGTGC (SEQ ID NO: 8); ANKRD22-f: CTCAGCCAGGAAGGATTTTG (SEQ ID NO: 9); ANKRD22-r: TGATAGGCTGCTTGGCAGAT (SEQ ID NO: 10).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows a schematic of an exemplary predictive model and theoretical framework. FIG. 1B shows an exemplary algorithm for determining an FRP score from gene expression values of selected genes.

FIG. 3A shows organ function and outcomes of 29 patients across five time points. FIG. 3B shows that, out of 29 AdHF-patients undergoing MCS-surgery, 17 patients improved (Group I, upper right quadrant) and 12 patients did not improve (Group II, remaining 3 quadrants) from day −1 (TP1) to day 8 (TP5). Each large dark bullet represents one patient who died within one year.

FIG. 5A shows hierarchical clustering of significant genes day −1 (TP1). Left: The Volcano plot of 28 genes, which are differentially expressed between Group I and Group II. Right: Hierarchical clustering of the 28 candidate genes for the prediction test demonstrates the differential gene expression between Group I and Group II. FIG. 5B shows hierarchical clustering of genes associated with survival benefit. Left: The Volcano plot of 105 genes, which are differentially expressed between Group I and Group II. Right: Hierarchical clustering 17 of the 105 candidate genes for the prediction test demonstrates the differential gene expression between Group I=Survival, Group II=Non-survival. FIG. 5C shows overlap genes from both improvement group and 1-year survival outcome. Left: Venn-Diagram shows the 28 DEGs identified in the comparison by Improvement Score (red; left circle) and the Right shows the 105 DEGs identified by comparing 1-Year Survival (blue; right circle). 12 DEGs were shared across the two comparisons. Right: The 12 overlap genes.

DETAILED DESCRIPTION OF THE INVENTION

Figure 1A:
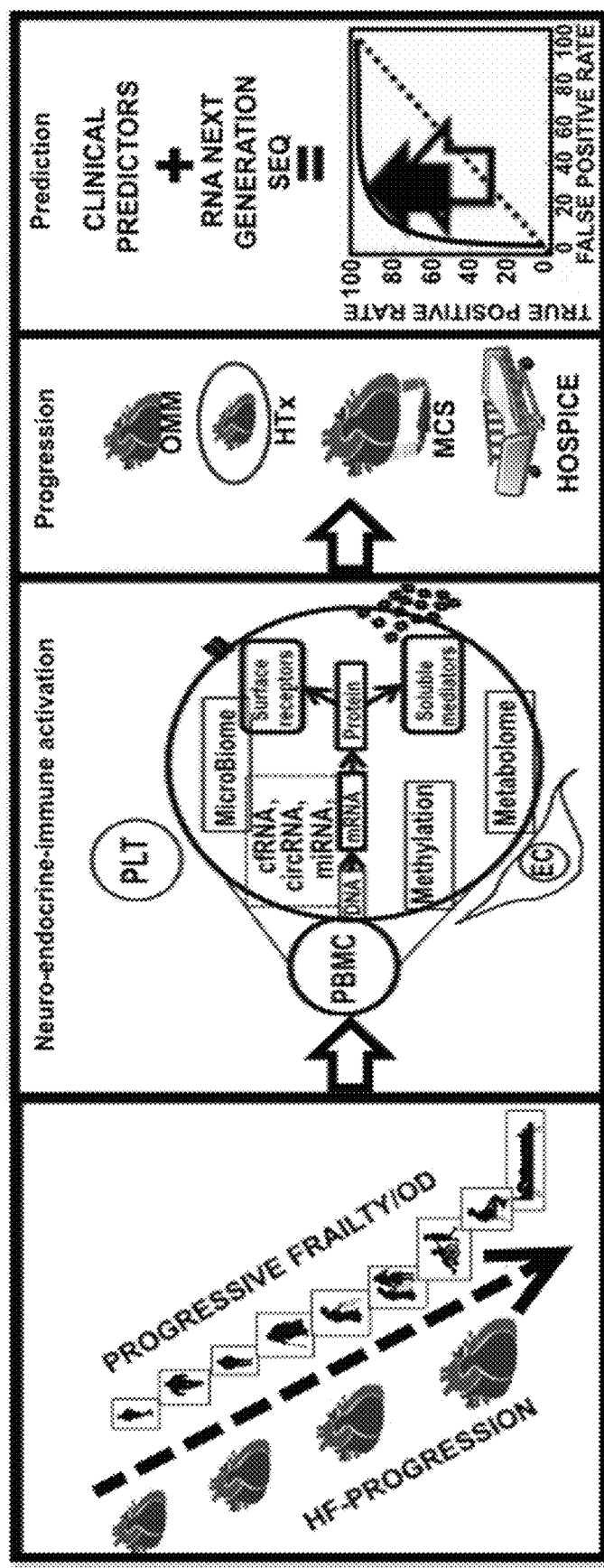
FIGS. 1A-1B show schematic illustrations of exemplary methods and frameworks described herein.

Described herein are methods and systems for providing a treatment to an individual based on a gene expression profile assay and classification system for predicting whether an individual has the potential to recover organ function after AdHF-surgical/interventional therapies, particularly for an individual suffering from heart failure and/or multiorgan dysfunction syndrome.

Definitions

All scientific and technical terms used in this application have meanings commonly used in the art unless otherwise specified. As used in this application, the following words or phrases have the meanings specified.

As used herein, "AdHF intervention" refers to treatments for advanced heart failure. Representative examples of AdHF surgical/interventional therapies include, but are not limited to: mechanical circulatory support (MCS), heart transplantation (HTx), coronary artery bypass graft (CABG) surgery, percutaneous coronary interventions (PCI), aortic valve replacement (AVR) surgery, mitral valve replacement (MVR) surgery, trans-catheter aortic valve replacement (TAVR), transcatheter Mitra-Clip, ventricular tachycardia ablation and stellate gangliectomy.

As used herein, "reference" in the context of gene expression levels refers to that observed in healthy volunteers, or in a subject who recovers from heart failure and/or major organ dysfunction. In some embodiments, the reference group is a set of normalization or control genes, as described herein.

As used herein, a "normalization gene" refers to a gene whose measured expression level does not discriminate between subjects who improve and those who do not improve with small standard deviations across samples.

As used herein, "a" or "an" means at least one, unless clearly indicated otherwise.

As used herein, to "prevent" or "protect against" a condition or disease means to hinder, reduce or delay the onset or progression of the condition or disease.

"About" a number, as used herein, refers to range including the number and ranging from 10% below that number to 10% above that number. "About" a range refers to 10% below the lower limit of the range, spanning to 10% above the upper limit of the range.

As used herein, the terms "treatment," "treating," "ameliorating a symptom," and the like, in some cases, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a heart condition, such as heart failure, in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. Treating may refer to any indicia of success in the treatment or amelioration or prevention of an heart condition, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms is based on one or more objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with heart disease or other diseases. The term "therapeutic effect" refers to the reduction, elimination, or prevention of the disease, symptoms of the disease, or side effects of the disease in the subject. A treatment, in some embodiments, comprises taking a course of action with respect to an individual. In some embodiments, a course of action taken with respect to an individual comprises no medical procedure being performed on the individual. In, some embodiments, a course of action taken with respect to an individual comprises conservative care or no additional care being provided.

Methods of Treatment

In some embodiments, there are provided methods of treating an individual in need thereof, such as methods of treating an individual suffering from a heart disease, such as heart failure. In some embodiments, there are provided methods of predicting treatment outcomes in an individual in need of heart failure interventional/surgical therapies. Some such methods comprise obtaining a gene expression value from a biological sample from the individual. In some embodiments, methods of treatment herein comprise (i) receiving a sample from an individual; and (ii) determining a gene expression level in the sample for at least one gene. In some embodiments, methods of treatment herein comprise providing a treatment to the individual based on the gene expression level. In some embodiments, methods herein comprise recommending a treatment to the individual based on the gene expression level. In some embodiments, the gene comprises at least one of RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, or FITM1. In some embodiments, the gene expression level in the sample is determined for at least two genes of RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, or FITM1.

In some embodiments, methods of treatment provided herein further comprise determining a function recovery potential (FRP) score based on the gene expression level. Function Recovery Potential (FRP=Resilience) score between 1 (lowest) and 10 (highest) to the sample that reflects the measured expression level of the genes. In one embodiment, as exemplified in the proof-of-concept study (Example 1), the FRP is defined using the Sequential Organ Failure Assessment score and Model of End-stage Liver Disease Except INR score (measured one day before and eight days after surgery): Group I=improving (both scores improved from day −1 to day 8) and Group II=not improving (either one or both scores did not improve from day −1 to day 8). The FRP correlates with 1-year survival. In some embodiments, the method further comprises (c) selecting a treatment of optimal medical management (OMM) and/or palliative care (PC) for the individual when the FRP score is 5 or less, and selecting a treatment of an AdHF intervention for the individual when the FRP score is 6 to 10. Examples of treatments comprising AdHF intervention include, but are not limited to, mechanical circulatory support (MCS) surgery, heart transplant (HTx) surgery, coronary artery bypass graft (CABG) surgery, percutaneous coronary interventions (PCI), aortic valve replacement (AVR) surgery, mitral valve replacement (MVR) surgery, trans-catheter aortic valve replacement (TAVR), transcatheter mitral clip, ventricular tachycardia ablation, and stellate gangliectomy.

Figure 1B:
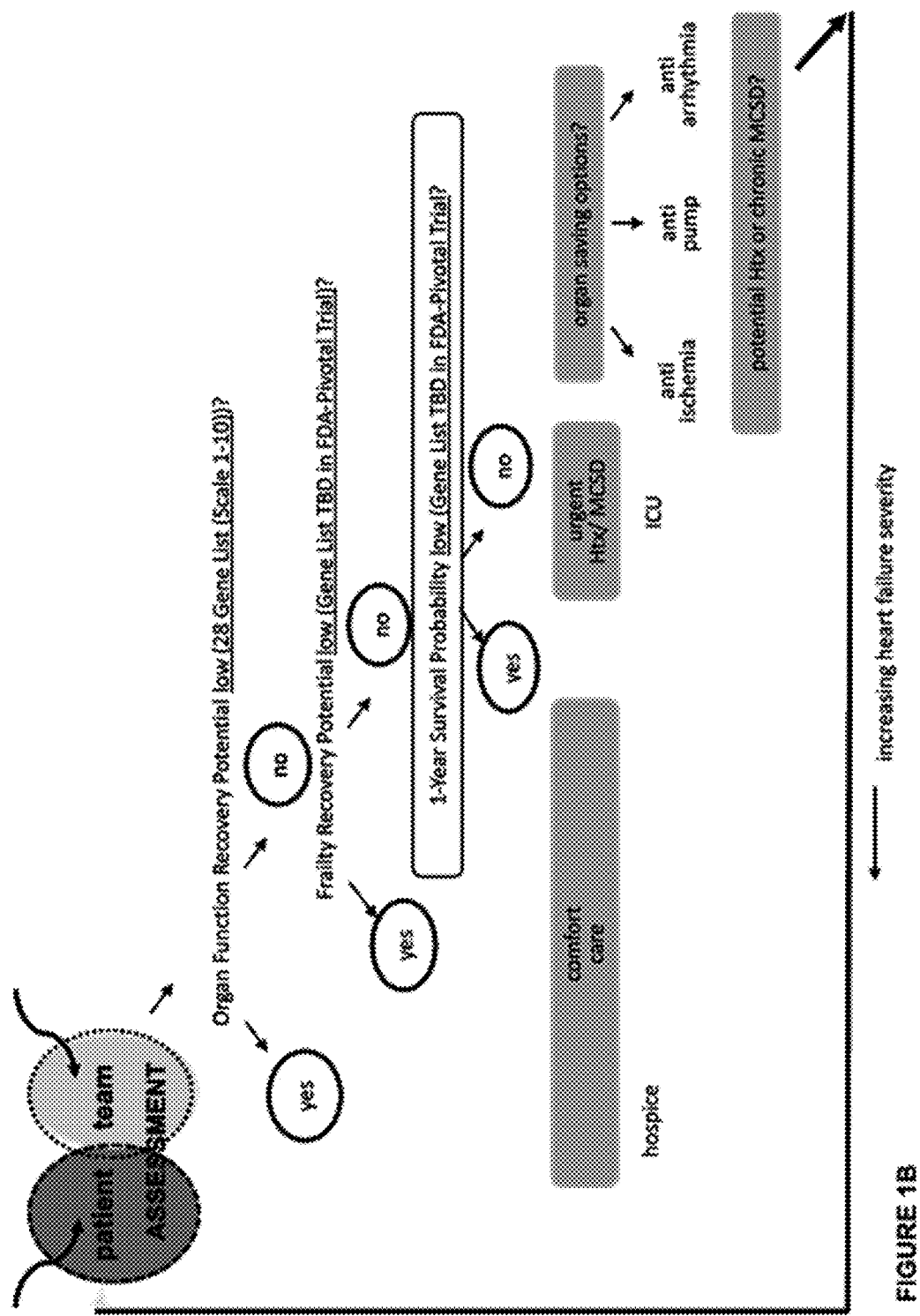

FIG. 1A illustrates an exemplary predictive model and theoretical framework. Worsening heart failure with reduced ejection fraction (HFrEF; left panel) is linked to progressive frailty/organ dysfunction (OD) via neuro-endocrine-immune activation mediated by complex interactions between diseased myocyte, peripheral blood mononuclear cells (PBMCs), endothelial cells (EC), and platelets (PLT) (middle panel). Outcome and comparative survival benefit prediction is improved by adding the molecular immunology biomarker or multidimensional molecular biomarker (MMB) to clinical predictors (upward arrow in bottom right ROC curve; right panel). FIG. 1B shows an exemplary algorithm for determining an FRP score from gene expression values of selected genes as described herein.

Gene Expression Profiling

In one embodiment, the invention provides a method of measuring gene expression in a biological sample obtained from a subject suffering from heart failure. In a related embodiment, the invention provides a method of reducing risk and optimizing treatment outcome for a subject suffering from organ failure. In one embodiment, the method comprises profiling gene expression in a sample of peripheral blood mononuclear cells (PBMCs). Typical steps of the method comprise: (a) measuring the expression level of a set of genes in the sample, wherein the set of genes are selected from those listed Tables 1A-1l, Table 2, Table 3, or Table 4A and 4B; and, based on this gene expression test result, (b) assigning a—clinical—Function Recovery Potential (FRP=Resilience) score between 1 (lowest) and 10 (highest) to the sample that reflects the measured expression level of the genes. The FRP is defined using the Sequential Organ Failure Assessment score and Model of End-stage Liver Disease Except INR score (measured one day before and eight days after surgery): Group I=improving (both scores improved from day −1 to day 8) and Group II=not improving (either one or both scores did not improve from day −1 to day 8). The FRP correlates with 1-year survival. In some embodiments, therefore, the method further comprises (c) referring the subject for treatment with optimal medical management (OMM) and/or palliative care (PC) if the FRP score is 5 or less, and referring the subject for treatment with an AdHF intervention if the FRP score is 6 to 10. Examples of AdHF intervention include, but are not limited to, mechanical circulatory support (MCS) surgery, heart transplant (HTx) surgery, coronary artery bypass graft (CABG) surgery, percutaneous coronary interventions (PCI), aortic valve replacement (AVR) surgery, mitral valve replacement (MVR) surgery, trans-catheter aortic valve replacement (TAVR), transcatheter mitral clip, ventricular tachycardia ablation, and stellate gangliectomy.

In some embodiments, the gene expression level varies from an expected expression level value. In some embodiments, the gene expression level is determined relative to another gene, such as a housekeeping gene or other appropriate gene exemplified herein. In some embodiments, the gene expression level is increased relative to an expected expression level value. In some embodiments, the gene expression level is decreased relative to an expected expression level value. In some cases, the gene expression level is assigned a score, such as an FRP score. In some embodiments, methods of treatment herein are determined based on the score. In some embodiments, the score is determined based on a linear discriminant analysis of data comprising known gene expression levels and known FRP scores of a plurality of individuals.

The number of genes included in the set of genes whose expression level is measured can range, during iterations of test development, from 5 to 100. In a typical embodiment, the expression level of at least 8 genes is measured. In some embodiments, the expression level of 10-75 genes is measured. In other embodiments, the expression level of 10-20, or 10-30 genes is measured. In one embodiment, the expression level of 10-15 genes is measured. In some illustrative specific embodiments, the set of genes is at least 10 of the genes listed in Table 2, at least 10 of the genes listed in Table 3 or at least 10 of the genes listed in Table 4A or 4B, or comprises one gene selected from each of Tables 1A-1I. In some embodiments, all of the genes listed in Tables 1, 2, 3, and/or 4 are measured. In one embodiment, the expression level of at least one gene in each of Tables 1A-1I is measured.

In a typical embodiment, the measuring comprises, for example, any one or a combination of RNA quantification, such as by next generation sequencing (NGS), polymerase chain reaction (PCR), gene array technology, or a hybridization platform (such as, for example, the NanoString nCounter system). In one embodiment, the measuring employs NanoString NCounter Hybridization. Those skilled in the art will appreciate alternative methods of measuring gene expression that can be employed. Likewise, where amplification methods require the use of primers, those skilled in the art can obtain appropriate primers either by referring to the exemplary primers described herein, or through publicly accessible databases. The methods can be performed using, for example, techniques for detecting gene expression, such as PCR, including RT-PCR, RNA-Seq, DNA microarrays, etc. Other assays can be employed, as will be understood to those skilled in the art.

For use in the methods described herein, representative examples of the sample include, but are not limited to, blood, plasma, serum, urine, or sputum, and other bodily fluids, particularly those containing PBMCs. PBMCs can be isolated, for example, from venous blood obtained via phlebotomy. RNA can be isolated from the PBMCs for use in the assays described herein. In some embodiments, the sample comprises blood, urine, sputum, hair, or skin.

In one embodiment, the method further comprises measuring normalization genes that will be empirically selected using PCR data from the training samples. Genes that do not discriminate between subjects who improve and those who do not improve with small standard deviations across all samples are considered as normalization genes. Specifically, normalization genes are chosen from a set of over 200 gene assays that include at least 10 genes described in the literature as housekeeping genes. The final control genes are selected using the following criteria: First, the amplicon assays need to show very low variance. Second, they must not show discrimination between Group I and Group II samples. Third, we identify amplicons that cover a range of CT values in a typical CP tube sample so as to control for CT dependent efficiency changes. The use of a set of control genes to normalize the amount of RNA present is based on the premise that an average from several measurements would be more robust than any single measurement and would also take into account any RNA abundance dependent effects.

In a typical embodiment, the measuring is performed one day prior to MCS or HTx surgery or other AdHF intervention. In some embodiments, the measuring is performed within 72 hours prior to surgery or other intervention. This approach facilitates tailoring the treatment of the subject to the subject's condition and prospects for improvement and recovery at the relevant point in time. A subject whose FRP score leads to recommending treatment with OMM or PC at one point in time can be evaluated again at a later point in time and subsequently be recommended for treatment with MCS or HTx or other AdHF intervention.

In some embodiments, the subject is suffering from heart failure with reduced ejection fraction. In some embodiments, the subject is suffering from heart failure with preserved ejection fraction.

The invention provides a method of predicting outcome of MCS or HTx or other AdHF intervention in a patient suffering from heart failure, comprising performing the method described above, wherein a poor outcome is predicted if the FRP score is 5 or less. In some embodiments, the methods of the invention further comprise treating the subject with OMM, PC, MCS, or HTx or other AdHF intervention, in accordance with the FRP score. In some embodiments, a poor outcome is predicted if the FRP score is 1-4, a score of 7-10 is predictive of recovery following advanced heart failure intervention, and a score of 5-6 is considered intermediate. For intermediate cases, other factors may be brought into the decision-making for treatment. In some embodiments, such other factors will include a subject's willingness to accept greater risk, or a preference for less aggressive treatment.

Further provided herein are methods of treating an individual. In some embodiments, methods of treatment comprise treatment for heart disease, such as heart failure or congestive heart failure. Methods of treatment provided herein comprise (i) receiving a sample from an individual; (ii) determining a gene expression level in the sample for at least one gene; and providing a treatment to the individual based on the gene expression level. In some embodiments, the gene comprises at least one of RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, or FITM1. In some embodiments, the gene expression level in the sample is determined for at least two genes of RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, or FITM1.

Also provided is a method of monitoring progression of heart failure in a subject. In one embodiment, the method comprises performing the method described above, wherein progression is detected if the FRP score is reduced by 2 relative to a prior measurement and wherein improvement is detected if the FRP score is increased by 2 relative to a prior measurement.

In some embodiments, the FRP corresponds to the measured expression level of the set of genes relative to a reference group of expression levels. The reference group may correspond to expression levels of the set of genes observed in healthy volunteers, or in a subject who recovers from heart failure and/or major organ dysfunction. In some embodiments, the reference group is a set of normalization or control genes, as described above.

Provided below is a list of genes whose expression levels can be measured for this assay. The 28 predictive genes have been grouped by WGCNA-derived modules representing integrated systems biological roles. Tables 1A-1I (or referred to collectively as "Table 1") list the 28 genes identified using a Mann-Whitney test based evaluation of data predicting day 8 organ function recovery. The full list of 28 genes appears as one group in Table 3 (known gene function summary in Table 5). Table 2 lists the 71 genes whose expression is predictive of day 8 organ function recovery based on t-test evaluation of data. Table 4A lists 12 genes that overlap between the genes listed in Table 3, predictive of day 8 organ function recovery, and genes whose expression is predictive of one-year survival. Table 4B lists genes whose expression is predictive of one-year survival.

Gene Test Combination Options:

In one embodiment, the gene is at least one gene selected from Table 1-4. In one embodiment, at least two or more genes of Table 1, 2 and/or 3 is used in combination. In one embodiment, at least three or more genes of Table 1, 2 and/or 3 is used in combination. In one embodiment, at least four or more genes of Table 1, 2 and/or 3 is used in combination. In one embodiment, at least five or more genes of Table 1, 2 and/or 3 is used in combination. In one embodiment, at least six or more genes of Table 1, 2 and/or 3 is used in combination. In one embodiment, at least seven or more genes of Table 1, 2 and/or 3 is used in combination. In one embodiment, at least eight or more genes of Table 1, 2 and/or 3 is used in combination. In one embodiment, at least nine or more genes of Table 1, 2 and/or 3 is used in combination. In one embodiment, at least ten or more genes of Table 1, 2 and/or 3 is used in combination. In one embodiment, at least 11 or more genes of Table 1, 2 and/or 3 is used in combination. In one embodiment, at least 12 or more genes of Table 1, 2 and/or 3 is used in combination. In one embodiment, at least 13 or more genes of Table 1, 2 and/or 3 is used in combination. In one embodiment, at least 14 or more genes of Table 1, 2 and/or 3 is used in combination. In one embodiment, at least 15 or more genes of Table 1, 2 and/or 3 is used in combination. In one embodiment, at least 16 or more genes of Table 1, 2 and/or 3 is used in combination. In one embodiment, at least 17 or more genes of Table 1, 2 and/or 3 is used in combination. In one embodiment, at least 18 or more genes of Table 1, 2 and/or 3 is used in combination. In one embodiment, at least 19 or more genes of Table 1, 2 and/or 3 is used in combination. In one embodiment, at least 20 or more genes of Table 1, 2 and/or 3 is used in combination. In one embodiment, at least 21 or more genes of Table 1, 2 and/or 3 is used in combination. In one embodiment, at least 22 or more genes of Table 1, 2 and/or 3 is used in combination. In one embodiment, at least 23 or more genes of Table 1, 2 and/or 3 is used in combination. In one embodiment, at least 24 or more genes of Table 1, 2 and/or 3 is used in combination. In one embodiment, at least 25 or more genes of Table 1, 2 and/or 3 is used in combination. In one embodiment, at least 26 or more genes of Table 1, 2 and/or 3 is used in combination. In one embodiment, at least 27 or more genes of Table 1, 2 and/or 3 is used in combination. In one embodiment, at least 28 or more genes of Table 1, 2 and/or 3 is used in combination. Examples of combinations of genes include: BATF2 and an additional gene selected from Table 1, 2, or 3; AGRN and an additional gene selected from Table 1, 2, or 3; ANKRD22 and an additional gene selected from Table 1, 2, or 3; DNM1P46 and an additional gene selected from Table 1, 2, or 3; FRMD6 and an additional gene selected from Table 1, 2, or 3; IL-17A and an additional gene selected from Table 1, 2, or 3; KIR2DL4 and an additional gene selected from Table 1, 2, or 3; BCORP1 and an additional gene selected from Table 1, 2, or 3; SAP25 and an additional gene selected from Table 1, 2, or 3; NAPSA and an additional gene selected from Table 1, 2, or 3; HEXA-AS1 and an additional gene selected from Table 1, 2, or 3; TIMP3 and an additional gene selected from Table 1, 2, or 3; RHBDD3 and an additional gene selected from Table 1, 2, or 3; any combination of 3 or more genes selected from Tables 1, 2 and 3; any combination of 4, 5, 6, 7, 8, 9, 10, 11, or 12 genes of Tables 1, 2 and 3. In one embodiment, the combination of genes is 2, 3, 4, or 5 genes selected from Table 1. In another embodiment, the combination of genes is at least one gene from Table 1, and at least one gene from Table 2. In another embodiment, the combination of genes is at least one gene from Table 1, and at least one gene from Table 3. In another embodiment, the combination of genes is at least one gene from Table 2, and at least one gene from Table 3. In another embodiment, the combination of genes is at least one gene from each of Tables 1, 2, and 3. In one embodiment, the combination of genes is all or a subset of the genes listed in one or more of Tables 1-4.

In some embodiments, the combination of genes comprises at least one gene selected from Table 1A. In some embodiments, the combination of genes comprises at least one gene selected from Table 1B. In some embodiments, the combination of genes comprises at least one gene selected from Table 10. In some embodiments, the combination of genes comprises at least one gene selected from Table 1D. In some embodiments, the combination of genes comprises at least one gene selected from Table 1E. In some embodiments, the combination of genes comprises at least one gene selected from Table 1F. In some embodiments, the combination of genes comprises at least one gene selected from Table 1G. In some embodiments, the combination of genes comprises at least one gene selected from Table 1H. In some embodiments, the combination of genes comprises at least one gene selected from Table 1I. In some embodiments, the combination of genes comprises at least two genes selected from Table 1A. In some embodiments, the combination of genes comprises at least two genes selected from Table 1B. In some embodiments, the combination of genes comprises at least two genes selected from Table 10. In some embodiments, the combination of genes comprises at least two genes selected from Table 1D. In some embodiments, the combination of genes comprises at least two genes selected from Table 1E. In some embodiments, the combination of genes comprises at least two genes selected from Table 1F. In some embodiments, the combination of genes comprises at least two genes selected from Table 1G. In some embodiments, the combination of genes comprises at least two genes selected from Table 1H. In some embodiments, the combination of genes comprises at least one gene selected from Table 1A, at least one gene selected from Table 1B, at least one gene selected from Table 10, at least one gene selected from Table 1D, at least one gene selected from Table 1E, at least one gene selected from Table 1F, at least one gene selected from Table 1G, at least one gene selected from Table 1H, and at least one gene selected from Table 1I. In some embodiments, the combination of genes comprises at least one gene selected from Table 1A, at least one gene selected from Table 1B, at least one gene selected from Table 10, at least one gene selected from Table 1D, at least one gene selected from Table 1E, at least one gene selected from Table 1F, at least one gene selected from Table 1G, at least one gene selected from Table 1H, and/or at least one gene selected from Table 1I.

In some embodiments, the combination of genes comprises at least one gene selected from Table 2. In some embodiments, the combination of genes comprises at least two genes selected from Table 2. In some embodiments, the combination of genes comprises at least three genes selected from Table 2. In some embodiments, the combination of genes comprises at least four genes selected from Table 2. In some embodiments, the combination of genes comprises at least five genes selected from Table 2. In some embodiments, the combination of genes comprises at least six genes selected from Table 2. In some embodiments, the combination of genes comprises at least seven genes selected from Table 2. In some embodiments, the combination of genes comprises at least eight genes selected from Table 2. In some embodiments, the combination of genes comprises at least nine genes selected from Table 2. In some embodiments, the combination of genes comprises at least ten genes selected from Table 2. In some embodiments, the combination of genes comprises at least 11 genes selected from Table 2. In some embodiments, the combination of genes comprises at least 12 genes selected from Table 2. In some embodiments, the combination of genes comprises at least 13 genes selected from Table 2. In some embodiments, the combination of genes comprises at least 14 genes selected from Table 2. In some embodiments, the combination of genes comprises at least 15 genes selected from Table 2. In some embodiments, the combination of genes comprises at least 16 genes selected from Table 2. In some embodiments, the combination of genes comprises at least 17 genes selected from Table 2. In some embodiments, the combination of genes comprises at least 18 genes selected from Table 2. In some embodiments, the combination of genes comprises at least 19 genes selected from Table 2. In some embodiments, the combination of genes comprises at least 20 genes selected from Table 2. In some embodiments, the combination of genes comprises at least 21 genes selected from Table 2. In some embodiments, the combination of genes comprises at least 22 genes selected from Table 2. In some embodiments, the combination of genes comprises at least 23 genes selected from Table 2. In some embodiments, the combination of genes comprises at least 24 genes selected from Table 2. In some embodiments, the combination of genes comprises at least 25 genes selected from Table 2. In some embodiments, the combination of genes comprises at least 26 genes selected from Table 2. In some embodiments, the combination of genes comprises at least 27 genes selected from Table 2. In some embodiments, the combination of genes comprises at least 28 genes selected from Table 2. In some embodiments, the combination of genes comprises AGRN and at least one additional gene from Table 2. In some embodiments, the combination of genes comprises RSG1 and at least one additional gene from Table 2. In some embodiments, the combination of genes comprises LOC728431 and at least one additional gene from Table 2. In some embodiments, the combination of genes comprises PDZK1IP1 and at least one additional gene from Table 2. In some embodiments, the combination of genes comprises NEGR1 and at least one additional gene from Table 2. In some embodiments, the combination of genes comprises HMCN1 and at least one additional gene from Table 2. In some embodiments, the combination of genes comprises CKAP2L and at least one additional gene from Table 2. In some embodiments, the combination of genes comprises ACVR1C and at least one additional gene from Table 2. In some embodiments, the combination of genes comprises KCNH8 and at least one additional gene from Table 2. In some embodiments, the combination of genes comprises CCR8 and at least one additional gene from Table 2. In some embodiments, the combination of genes comprises TPRA1 and at least one additional gene from Table 2. In some embodiments, the combination of genes comprises IGSF10 and at least one additional gene from Table 2. In some embodiments, the combination of genes comprises MME and at least one additional gene from Table 2. In some embodiments, the combination of genes comprises ETV5 and at least one additional gene from Table 2. In some embodiments, the combination of genes comprises CXCL9 and at least one additional gene from Table 2. In some embodiments, the combination of genes comprises HBEGF and at least one additional gene from Table 2. In some embodiments, the combination of genes comprises RANBP17 and at least one additional gene from Table 2. In some embodiments, the combination of genes comprises DDX43 and at least one additional gene from Table 2. In some embodiments, the combination of genes comprises C6orf164 and at least one additional gene from Table 2. In some embodiments, the combination of genes comprises GPR63 and at least one additional gene from Table 2. In some embodiments, the combination of genes comprises SLC22A1 and at least one additional gene from Table 2. In some embodiments, the combination of genes comprises C7orf50 and at least one additional gene from Table 2. In some embodiments, the combination of genes comprises SAP25 and at least one additional gene from Table 2. In some embodiments, the combination of genes comprises NEFL and at least one additional gene from Table 2. In some embodiments, the combination of genes comprises CDCA2 and at least one additional gene from Table 2. In some embodiments, the combination of genes comprises MFSD3 and at least one additional gene from Table 2. In some embodiments, the combination of genes comprises ALDH1A1 and at least one additional gene from Table 2. In some embodiments, the combination of genes comprises OLFM1 and at least one additional gene from Table 2. In some embodiments, the combination of genes comprises ANKRD22 and at least one additional gene from Table 2. In some embodiments, the combination of genes comprises FADS3 and at least one additional gene from Table 2. In some embodiments, the combination of genes comprises BATF2 and at least one additional gene from Table 2. In some embodiments, the combination of genes comprises SAC3D1 and at least one additional gene from Table 2. In some embodiments, the combination of genes comprises FZD4 and at least one additional gene from Table 2. In some embodiments, the combination of genes comprises FITM1 and at least one additional gene from Table 2. In some embodiments, the combination of genes comprises FRMD6 and at least one additional gene from Table 2. In some embodiments, the combination of genes comprises SPTBN5 and at least one additional gene from Table 2. In some embodiments, the combination of genes comprises RBPMS2 and at least one additional gene from Table 2. In some embodiments, the combination of genes comprises HEXA-AS1 and at least one additional gene from Table 2. In some embodiments, the combination of genes comprises C15orf38 and at least one additional gene from Table 2. In some embodiments, the combination of genes comprises DNM1P46 and at least one additional gene from Table 2. In some embodiments, the combination of genes comprises CEMP1 and at least one additional gene from Table 2. In some embodiments, the combination of genes comprises ST6GALNAC1 and at least one additional gene from Table 2. In some embodiments, the combination of genes comprises CHMP6 and at least one additional gene from Table 2. In some embodiments, the combination of genes comprises ASPSCR1 and at least one additional gene from Table 2. In some embodiments, the combination of genes comprises SKA1 and at least one additional gene from Table 2. In some embodiments, the combination of genes comprises CD209 and at least one additional gene from Table 2. In some embodiments, the combination of genes comprises SNAPC2 and at least one additional gene from Table 2. In some embodiments, the combination of genes comprises AXL and at least one additional gene from Table 2. In some embodiments, the combination of genes comprises NAPSB and at least one additional gene from Table 2. In some embodiments, the combination of genes comprises NAPSA and at least one additional gene from Table 2. In some embodiments, the combination of genes comprises KIR2DL1 and at least one additional gene from Table 2. In some embodiments, the combination of genes comprises KIR2DL4 and at least one additional gene from Table 2. In some embodiments, the combination of genes comprises NLRP2 and at least one additional gene from Table 2. In some embodiments, the combination of genes comprises NTSR1 and at least one additional gene from Table 2. In some embodiments, the combination of genes comprises SEPT5 and at least one additional gene from Table 2. In some embodiments, the combination of genes comprises RHBDD3 and at least one additional gene from Table 2. In some embodiments, the combination of genes comprises TIMP3 and at least one additional gene from Table 2. In some embodiments, the combination of genes comprises KAL1 and at least one additional gene from Table 2. In some embodiments, the combination of genes comprises PRRG1 and at least one additional gene from Table 2. In some embodiments, the combination of genes comprises XIST and at least one additional gene from Table 2. In some embodiments, the combination of genes comprises RPS4Y1 and at least one additional gene from Table 2. In some embodiments, the combination of genes comprises ZFY and at least one additional gene from Table 2. In some embodiments, the combination of genes comprises PRKY and at least one additional gene from Table 2. In some embodiments, the combination of genes comprises TTTY15 and at least one additional gene from Table 2. In some embodiments, the combination of genes comprises USP9Y and at least one additional gene from Table 2. In some embodiments, the combination of genes comprises DDX3Y and at least one additional gene from Table 2. In some embodiments, the combination of genes comprises UTY and at least one additional gene from Table 2. In some embodiments, the combination of genes comprises BCORP1 and at least one additional gene from Table 2. In some embodiments, the combination of genes comprises TXLNG2P and at least one additional gene from Table 2. In some embodiments, the combination of genes comprises KDM5D and at least one additional gene from Table 2. In some embodiments, the combination of genes comprises EIF1AY and at least one additional gene from Table 2.

In some embodiments, the combination of genes comprises at least one gene selected from Table 3. In some embodiments, the combination of genes comprises at least two genes selected from Table 3. In some embodiments, the combination of genes comprises at least three genes selected from Table 3. In some embodiments, the combination of genes comprises at least four genes selected from Table 3. In some embodiments, the combination of genes comprises at least five genes selected from Table 3. In some embodiments, the combination of genes comprises at least six genes selected from Table 3. In some embodiments, the combination of genes comprises at least seven genes selected from Table 3. In some embodiments, the combination of genes comprises at least eight genes selected from Table 3. In some embodiments, the combination of genes comprises at least nine genes selected from Table 3. In some embodiments, the combination of genes comprises at least ten genes selected from Table 3. In some embodiments, the combination of genes comprises at least 11 genes selected from Table 3. In some embodiments, the combination of genes comprises at least 12 genes selected from Table 3. In some embodiments, the combination of genes comprises at least 13 genes selected from Table 3. In some embodiments, the combination of genes comprises at least 14 genes selected from Table 3. In some embodiments, the combination of genes comprises at least 15 genes selected from Table 3. In some embodiments, the combination of genes comprises at least 16 genes selected from Table 3. In some embodiments, the combination of genes comprises at least 17 genes selected from Table 3. In some embodiments, the combination of genes comprises at least 18 genes selected from Table 3. In some embodiments, the combination of genes comprises at least 19 genes selected from Table 3. In some embodiments, the combination of genes comprises at least 20 genes selected from Table 3. In some embodiments, the combination of genes comprises at least 21 genes selected from Table 3. In some embodiments, the combination of genes comprises at least 22 genes selected from Table 3. In some embodiments, the combination of genes comprises at least 23 genes selected from Table 3. In some embodiments, the combination of genes comprises at least 24 genes selected from Table 3. In some embodiments, the combination of genes comprises at least 25 genes selected from Table 3. In some embodiments, the combination of genes comprises at least 26 genes selected from Table 3. In some embodiments, the combination of genes comprises at least 27 genes selected from Table 3. In some embodiments, the combination of genes comprises USP9Y and at least one additional gene from Table 3. In some embodiments, the combination of genes comprises BATF2 and at least one additional gene from Table 3. In some embodiments, the combination of genes comprises AGRN and at least one additional gene from Table 3. In some embodiments, the combination of genes comprises ANKRD22 and at least one additional gene from Table 3. In some embodiments, the combination of genes comprises HMCN1 and at least one additional gene from Table 3. In some embodiments, the combination of genes comprises ACVR1C and at least one additional gene from Table 3. In some embodiments, the combination of genes comprises GPR63 and at least one additional gene from Table 3. In some embodiments, the combination of genes comprises DNM1P46 and at least one additional gene from Table 3. In some embodiments, the combination of genes comprises CKAP2L and at least one additional gene from Table 3. In some embodiments, the combination of genes comprises FRMD6 and at least one additional gene from Table 3. In some embodiments, the combination of genes comprises KIR2DL4 and at least one additional gene from Table 3. In some embodiments, the combination of genes comprises IGSF10 and at least one additional gene from Table 3. In some embodiments, the combination of genes comprises BCORP1 and at least one additional gene from Table 3. In some embodiments, the combination of genes comprises SAP25 and at least one additional gene from Table 3. In some embodiments, the combination of genes comprises NAPSA and at least one additional gene from Table 3. In some embodiments, the combination of genes comprises FITM1 and at least one additional gene from Table 3. In some embodiments, the combination of genes comprises SPTBN5 and at least one additional gene from Table 3. In some embodiments, the combination of genes comprises HEXA-AS1 and at least one additional gene from Table 3. In some embodiments, the combination of genes comprises SLC22A1 and at least one additional gene from Table 3. In some embodiments, the combination of genes comprises RSG1 and at least one additional gene from Table 3. In some embodiments, the combination of genes comprises TIM P3 and at least one additional gene from Table 3. In some embodiments, the combination of genes comprises TPRA1 and at least one additional gene from Table 3. In some embodiments, the combination of genes comprises CEMP1 and at least one additional gene from Table 3. In some embodiments, the combination of genes comprises ASPSCR1 and at least one additional gene from Table 3. In some embodiments, the combination of genes comprises MFSD3 and at least one additional gene from Table 3. In some embodiments, the combination of genes comprises NAPSB and at least one additional gene from Table 3. In some embodiments, the combination of genes comprises NLRP2 and at least one additional gene from Table 3. In some embodiments, the combination of genes comprises RHBDD3 and at least one additional gene from Table 3.

In some embodiments, the combination of genes comprises at least one gene selected from Table 4A. In some embodiments, the combination of genes comprises at least two genes selected from Table 4A. In some embodiments, the combination of genes comprises at least three genes selected from Table 4A. In some embodiments, the combination of genes comprises at least four genes selected from Table 4A. In some embodiments, the combination of genes comprises at least five genes selected from Table 4A. In some embodiments, the combination of genes comprises at least six genes selected from Table 4A. In some embodiments, the combination of genes comprises at least seven genes selected from Table 4A. In some embodiments, the combination of genes comprises at least eight genes selected from Table 4A. In some embodiments, the combination of genes comprises at least nine genes selected from Table 4A.

In some embodiments, the combination of genes comprises at least ten genes selected from Table 4A. In some embodiments, the combination of genes comprises at least 11 genes selected from Table 4A. In some embodiments, the combination of genes comprises BATF2 and at least one additional gene from Table 2. In some embodiments, the combination of genes comprises AGRN and at least one additional gene from Table 2. In some embodiments, the combination of genes comprises ANKRD22 and at least one additional gene from Table 2. In some embodiments, the combination of genes comprises DNM1P46 and at least one additional gene from Table 2. In some embodiments, the combination of genes comprises FRMD6 and at least one additional gene from Table 2. In some embodiments, the combination of genes comprises KIR2DL4 and at least one additional gene from Table 2. In some embodiments, the combination of genes comprises BCORP1 and at least one additional gene from Table 2. In some embodiments, the combination of genes comprises SAP25 and at least one additional gene from Table 2. In some embodiments, the combination of genes comprises NAPSA and at least one additional gene from Table 2. In some embodiments, the combination of genes comprises HEXA-AS1 and at least one additional gene from Table 2. In some embodiments, the combination of genes comprises TIMP3 and at least one additional gene from Table 2. In some embodiments, the combination of genes comprises RHBDD3 and at least one additional gene from Table 2.

In some embodiments, the combination of genes comprises at least one gene selected from Table 4B. In some embodiments, the combination of genes comprises at least two genes selected from Table 4B. In some embodiments, the combination of genes comprises at least three genes selected from Table 4B. In some embodiments, the combination of genes comprises at least four genes selected from Table 4B. In some embodiments, the combination of genes comprises at least five genes selected from Table 4B. In some embodiments, the combination of genes comprises at least six genes selected from Table 4B. In some embodiments, the combination of genes comprises at least seven genes selected from Table 4B. In some embodiments, the combination of genes comprises at least eight genes selected from Table 4B. In some embodiments, the combination of genes comprises at least nine genes selected from Table 4B. In some embodiments, the combination of genes comprises at least ten genes selected from Table 4B. In some embodiments, the combination of genes comprises at least 11 genes selected from Table 4B. In some embodiments, the combination of genes comprises at least 12 genes selected from Table 4B. In some embodiments, the combination of genes comprises at least 13 genes selected from Table 4B. In some embodiments, the combination of genes comprises at least 14 genes selected from Table 4B. In some embodiments, the combination of genes comprises at least 15 genes selected from Table 4B. In some embodiments, the combination of genes comprises at least 16 genes selected from Table 4B. In some embodiments, the combination of genes comprises at least 17 genes selected from Table 4B. In some embodiments, the combination of genes comprises at least 18 genes selected from Table 4B. In some embodiments, the combination of genes comprises at least 19 genes selected from Table 4B. In some embodiments, the combination of genes comprises at least 20 genes selected from Table 4B. In some embodiments, the combination of genes comprises at least 21 genes selected from Table 4B. In some embodiments, the combination of genes comprises at least 22 genes selected from Table 4B. In some embodiments, the combination of genes comprises at least 23 genes selected from Table 4B. In some embodiments, the combination of genes comprises at least 24 genes selected from Table 4B. In some embodiments, the combination of genes comprises at least 25 genes selected from Table 4B. In some embodiments, the combination of genes comprises at least 26 genes selected from Table 4B. In some embodiments, the combination of genes comprises at least 27 genes selected from Table 4B. In some embodiments, the combination of genes comprises at least 28 genes selected from Table 4B.

TABLE 1A (12 members of module blue (Metabolism); right two columns indicate direction of regulation):

| Gene ID | Gene Symbol | Recovery Group | OMM/PC Group |
|---|---|---|---|
| 79363 | RSG1 | Up | Down |
| 131601 | TPRA1 | Up | Down |
| 100316904 | SAP25 | Up | Down |
| 113655 | MFSD3 | Up | Down |
| 161247 | FITM1 | Up | Down |
| 51332 | SPTBN5 | Up | Down |
| 752014 | CEMP1 | Up | Down |
| 79058 | ASPSCR1 | Up | Down |
| 256236 | NAPSB | Up | Down |
| 9476 | NAPSA | Up | Down |
| 55655 | NLRP2 | Up | Down |
| 25807 | RHBDD3 | Up | Down |

TABLE 1B (2 members of module black (Catabolic Metabolism); right two columns indicate direction of regulation):

| Gene ID | Gene Symbol | Recovery Group | OMM/PC Group |
|---|---|---|---|
| 122786 | FRMD6 | Down | Up |
| 7078 | TIMP3 | Up | Down |

TABLE 1C (2 members of module green (T Cell Regulation); right two columns indicate direction of regulation):

| Gene ID | Gene Symbol | Recovery Group | OMM/PC Group |
|---|---|---|---|
| 130399 | ACVR1C | Down | Up |
| 196968 | DNM1P46 | Down | Up |

TABLE 1D (2 members of module pink (Immune System Development); right two columns indicate direction of regulation):

| Gene ID | Gene Symbol | Recovery Group | OMM/PC Group |
|---|---|---|---|
| 3805 | KIR2DL4 | Down | Up |
| 8287 | USP9Y | Down | Up |

TABLE 1E (2 members of module turquoise (RNA Metabolism); right two columns indicate direction of regulation):

| Gene ID | Gene Symbol | Recovery Group | OMM/PC Group |
|---|---|---|---|
| 118932 | ANKRD22 | Down | Up |
| 286554 | BCORP1 | Down | Up |

TABLE 1F (2 members of module lightgreen (* GO Biological Process Not Classified); right two columns indicate direction of regulation):

| Gene ID | Gene Symbol | Recovery Group | OMM/PC Group |
|---|---|---|---|
| 83872 | HMCN1 | Down | Up |
| 81491 | GPR63 | Down | Up |

TABLE 1G (1 member of module cyan (Innate Immunity); right two columns indicate direction of regulation):

| Gene ID | Gene Symbol | Recovery Group | OMM/PC Group |
|---|---|---|---|
| 116071 | BATF2 | Down | Up |

TABLE 1H (1 member of module darkred (Immune Process); right two columns indicate direction of regulation):

| Gene ID | Gene Symbol | Recovery Group | OMM/PC Group |
|---|---|---|---|
| 6580 | SLC22A1 | Up | Down |

TABLE 1I (4 members of module grey (Unclustered); right two columns indicate direction of regulation):

| Gene ID | Gene Symbol | Recovery Group | OMM/PC Group |
|---|---|---|---|
| 375790 | AGRN | Down | Up |
| 150468 | CKAP2L | Down | Up |
| 285313 | IGSF10 | Down | Up |
| 80072 | HEXA-AS1 | Up | Down |

TABLE 2

(UCLA t-test based list of 71 genes predicting day 8 organ function recovery)

| Gene ID | Gene Symbol | Recovery Group | OMM/PC Group |
|---|---|---|---|
| 375790 | AGRN | Down | Up |
| 79363 | RSG1 | Up | Down |
| 728431 | LOC728431 | Up | Down |
| 10158 | PDZK1IP1 | Up | Down |
| 257194 | NEGR1 | Down | Up |
| 83872 | HMCN1 | Down | Up |
| 150468 | CKAP2L | Down | Up |
| 130399 | ACVR1C | Down | Up |
| 131096 | KCNH8 | Down | Up |
| 1237 | CCR8 | Down | Up |
| 131601 | TPRA1 | Up | Down |
| 285313 | IGSF10 | Down | Up |
| 4311 | MME | Down | Up |
| 2119 | ETV5 | Up | Down |
| 4283 | CXCL9 | Down | Up |
| 1839 | HBEGF | Down | Up |
| 64901 | RANBP17 | Up | Down |
| 55510 | DDX43 | Down | Up |
| 63914 | C6orf164 | Up | Down |
| 81491 | GPR63 | Down | Up |
| 6580 | SLC22A1 | Up | Down |
| 84310 | C7orf50 | Up | Down |
| 1E+08 | SAP25 | Up | Down |
| 4747 | NEFL | Down | Up |
| 157313 | CDCA2 | Down | Up |
| 113655 | MFSD3 | Up | Down |
| 216 | ALDH1A1 | Down | Up |
| 10439 | OLFM1 | Down | Up |
| 118932 | ANKRD22 | Down | Up |
| 3995 | FADS3 | Up | Down |
| 116071 | BATF2 | Down | Up |
| 29901 | SAC3D1 | Up | Down |
| 8322 | FZD4 | Down | Up |
| 161247 | FITM1 | Up | Down |
| 122786 | FRMD6 | Down | Up |
| 51332 | SPTBN5 | Up | Down |
| 348093 | RBPMS2 | Up | Down |
| 80072 | HEXA-AS1 | Up | Down |
| 348110 | C15orf38 | Down | Up |
| 196968 | DNM1P46 | Down | Up |
| 752014 | CEMP1 | Up | Down |
| 55808 | ST6GALNAC1 | Down | Up |
| 79643 | CHMP6 | Up | Down |
| 79058 | ASPSCR1 | Up | Down |
| 220134 | SKA1 | Down | Up |
| 30835 | CD209 | Down | Up |
| 6618 | SNAPC2 | Up | Down |
| 558 | AXL | Down | Up |
| 256236 | NAPSB | Up | Down |
| 9476 | NAPSA | Up | Down |
| 3802 | KIR2DL1 | Down | Up |
| 3805 | KIR2DL4 | Down | Up |
| 55655 | NLRP2 | Up | Down |
| 4923 | NTSR1 | Up | Down |
| 5413 | SEPT5 | Up | Down |
| 25807 | RHBDD3 | Up | Down |
| 7078 | TIMP3 | Up | Down |
| 3730 | KAL1 | Down | Up |
| 5638 | PRRG1 | Down | Up |
| 7503 | XIST | Up | Down |
| 6192 | RPS4Y1 | Down | Up |
| 7544 | ZFY | Down | Up |
| 5616 | PRKY | Down | Up |
| 64595 | TTTY15 | Down | Up |
| 8287 | USP9Y | Down | Up |
| 8653 | DDX3Y | Down | Up |
| 7404 | UTY | Down | Up |
| 286554 | BCORP1 | Down | Up |
| 246126 | TXLNG2P | Down | Up |
| 8284 | KDM5D | Down | Up |
| 9086 | EIF1AY | Down | Up |

TABLE 3

(UCLA Mann-Whitney-test based list of 28 genes predicting day 8 organ function recovery)

| Gene ID | Gene Symbol | Recovery Group | OMM/PC Group |
|---|---|---|---|
| 8287 | USP9Y | Down | Up |
| 116071 | BATF2 | Down | Up |
| 375790 | AGRN | Down | Up |
| 118932 | ANKRD22 | Down | Up |
| 83872 | HMCN1 | Down | Up |
| 130399 | ACVR1C | Down | Up |
| 81491 | GPR63 | Down | Up |
| 196968 | DNM1P46 | Down | Up |
| 150468 | CKAP2L | Down | Up |
| 122786 | FRMD6 | Down | Up |
| 3805 | KIR2DL4 | Down | Up |
| 2855313 | IGSF10 | Down | Up |
| 286554 | BCORP1 | Down | Up |
| 100316904 | SAP25 | Up | Down |
| 9476 | NAPSA | Up | Down |
| 161247 | FITM1 | Up | Down |
| 51332 | SPTBN5 | Up | Down |
| 80072 | HEXA-AS1 | Up | Down |

TABLE 3-continued (UCLA Mann-Whitney-test based list of 28 genes predicting day 8 organ function recovery)

| Gene ID | Gene Symbol | Recovery Group | OMM/PC Group |
|---|---|---|---|
| 6580 | SLC22A1 | Up | Down |
| 79363 | RSG1 | Up | Down |
| 7078 | TIMP3 | Up | Down |
| 131601 | TPRA1 | Up | Down |
| 752014 | CEMP1 | Up | Down |
| 79058 | ASPSCR1 | Up | Down |
| 113655 | MFSD3 | Up | Down |
| 256236 | NAPSB | Up | Down |
| 55655 | NLRP2 | Up | Down |
| 25807 | RHBDD3 | Up | Down |

TABLE 4A (12 gene overlap list of UCLA Mann-Whitney-test based list of 28 genes predicting day 8 organ function recovery and predicting 1-year survival)

| Gene ID | Gene Symbol | Recovery Group | OMM/PC Group |
|---|---|---|---|
| 116071 | BATF2 | Down | Up |
| 375790 | AGRN | Down | Up |
| 118932 | ANKRD22 | Down | Up |
| 196968 | DNM1P46 | Down | Up |
| 122786 | FRMD6 | Down | Up |
| 3805 | KIR2DL4 | Down | Up |
| 286554 | BCORP1 | Down | Up |
| 100316904 | SAP25 | Up | Down |
| 9476 | NAPSA | Up | Down |
| 80072 | HEXA-AS1 | Up | Down |
| 7078 | TIMP3 | Up | Down |
| 25807 | RHBDD3 | UP | Down |

TABLE 4B (105 genes predicting 1-year survival)

| Gene ID | Gene Symbol | Regulation in 1-year survival group |
|---|---|---|
| 375790 | AGRN* | down |
| 10911 | UTS2 | down |
| 90853 | SPOCD1 | up |
| 728431 | LOC728431 | up |
| 26027 | ACOT11 | up |
| 257194 | NEGR1 | down |
| 388646 | GBP7 | down |
| 163351 | GBP6 | down |
| 1952 | CELSR2 | down |
| 644591 | PPIAL4G | up |
| 913 | CD1E | down |
| 116123 | FMO9P | down |
| 8497 | PPFIA4 | up |
| 400950 | C2orf91 | down |
| 84279 | PRADC1 | up |
| 3625 | INHBB | down |
| 5270 | SERPINE2 | up |
| 643387 | LOC643387 | down |
| 79750 | ZNF385D | up |
| 115560 | ZNF501 | down |
| 2815 | GP9 | up |
| 55214 | LEPREL1 | down |
| 151963 | MB21D2 | down |
| 200958 | MUC20 | up |
| 401115 | C4orf48 | up |
| 84740 | AFAP1-AS1 | down |
| 152831 | KLB | down |
| 677810 | SNORA26 | down |
| 8492 | PRSS12 | down |
| 79931 | TNIP3 | down |
| 7098 | TLR3 | down |
| 3003 | GZMK | down |

TABLE 4B-continued (105 genes predicting 1-year survival)

| Gene ID | Gene Symbol | Regulation in 1-year survival group |
|---|---|---|
| 140947 | C5orf20 | down |
| 9832 | JAKMIP2 | down |
| 9509 | ADAMTS2 | up |
| 51149 | C5orf45 | up |
| 10471 | PFDN6 | down |
| 594839 | SNORA33 | up |
| 84310 | C7orf50 | up |
| 2791 | GNG11 | up |
| 100316904 | SAP25* | up |
| 4747 | NEFL | down |
| 1135 | CHRNA2 | up |
| 6129 | RPL7 | down |
| 157638 | FAM84B | down |
| 26149 | ZNF658 | down |
| 216 | ALDH1A1 | down |
| 10439 | OLFM1 | down |
| 1959 | EGR2 | down |
| 118881 | COMTD1 | up |
| 118932 | ANKRD22* | down |
| 619562 | SNORA3 | down |
| 79080 | CCDC86 | down |
| 11251 | PTGDR2 | down |
| 116071 | BATF2* | down |
| 55359 | STYK1 | down |
| 6297 | SALL2 | down |
| 122786 | FRMD6* | down |
| 161291 | TMEM30B | down |
| 100750247 | HIF1A-AS2 | up |
| 8747 | ADAM21 | down |
| 440278 | CATSPER2P1 | down |
| 348093 | RBPMS2 | up |
| 595097 | SNORD16 | down |
| 80072 | HEXA-AS1* | up |
| 348110 | C15orf38 | down |
| 196968 | DNM1P46* | down |
| 645811 | CCDC154 | up |
| 5376 | PMP22 | down |
| 400617 | KCNJ2-AS1 | up |
| 645158 | CBX3P2 | down |
| 220134 | SKA1 | down |
| 79839 | CCDC102B | down |
| 284451 | ODF3L2 | down |
| 79187 | FSD1 | up |
| 30835 | CD209 | down |
| 4066 | LYL1 | up |
| 773 | CACNA1A | down |
| 26659 | OR7A5 | down |
| 126248 | WDR88 | up |
| 3743 | KCNA7 | down |
| 9476 | NAPSA* | up |
| 79986 | ZNF702P | down |
| 94059 | LENG9 | up |
| 3805 | KIR2DL4* | down |
| 282566 | LINC00515 | up |
| 9510 | ADAMTS1 | down |
| 11274 | USP18 | down |
| 5413 | SEPT5 | up |
| 100526833 | SEPT5-GP1BB | up |
| 2812 | GP1BB | up |
| 1415 | CRYBB2 | down |
| 91353 | IGLL3P | down |
| 23544 | SEZ6L | down |
| 25807 | RHBDD3* | up |
| 7078 | TIMP3* | up |
| 79924 | ADM2 | down |
| 284942 | RPL23AP82 | down |
| 5638 | PRRG1 | down |
| 27238 | GPKOW | down |
| 139189 | DGKK | down |
| 1741 | DLG3 | down |
| 56000 | NXF3 | up |
| 8653 | DDX3Y | down |
| 286554 | BCORP1* | down |

*indicates overlap with genes listed in Table 3

FRP Scoring

In certain embodiments of methods provided herein, a functional recovery potential (FRP) score is based on a linear discriminant analysis of the gene expression profiles on day −1 (or up to 72 hours) before the AdHF intervention that are predictive of improvement in organ function recovery, or "functional recovery", after the AdHF intervention, such as can be obtained from the information described in Tables 1-4 herein. One can perform this linear discriminant analysis using all 28 of the genes listed in Table 3, a select subset, for example, of 10-20 genes shown to be predictive of FRP. The linear discriminant analysis is adapted from the development of the Allomap test (Deng et al. AJT 2006:6:150), the first in history FDA-cleared cardiovascular in-vitro-diagnostic multivariate index assay (IVDMIA) test to assist the clinician in ruling out heart transplantation rejection, to select genes and/or metagenes that, in combination, optimally predict functional recovery. As more data are gathered, for example, following completion of a planned 1000 patient FDA-Pivotal Trial, the functional recovery potential (FRP) can be refined further according to the rationale described in Deng, M C, A peripheral blood transcriptome biomarker test to diagnose functional recovery potential in advanced heart failure. Biomark Med. 2018 May 8. doi: 10.2217/bmm-2018-0097. Such further refinement includes, for example, weighting the contribution of individual genes to the FRP score as the analysis reveals which genes have greater predictive value.

Thus, the invention provides a method for developing a function recovery potential (FRP) scoring algorithm that predicts a subject's ability to recover from medical intervention for organ failure. In one embodiment, the method comprises (a) obtaining the expression levels of at least 10 of the 28 genes listed in Table 3 using pre-intervention and post-intervention expression levels of the at least 10 genes observed in PBMC samples obtained from a population of patients treated with medical intervention for organ failure; (b) performing linear discriminant analysis of the expression levels obtained in (a) to classify the PBMC samples into Group I (post-intervention improvement) or Group II (non-improvement); (c) estimating the effect size of each of the gene expression levels on the classification of a sample into Group I or Group II; and (d) adjusting the FRP scoring algorithm by weighting the contribution of each of the genes in accordance with the effect size. Estimating the effect size can comprise, for example, determining the eigenvalue for each gene, or it can be based on the canonical correlation.

As described in the Examples below, and now published as Bondar, G. et al., PLoS One 2017 Dec. 13; 12(12), one can construct a PBMC-GEP-prediction model using preoperative day −1 patient data to predict and classify postoperative Group I (functional recovery; low risk; high FRP score) vs. Group II (no recovery of organ function; high risk; low FRP score). In the proof of concept study (Bondar, G. et al. 2017 cited above), to achieve a prediction model with highest accuracy for classification of patients into Group I vs. Group II, Strand NGS v2.9 was used for the alignment and analysis of the RNA-Seq data. After alignment, DESeq normalization, filtering and fold change analysis of genes expressed above noise levels resulted in 28 genes.

The 28 PBMC-genes that are differentially expressed between Group I and Group II were identified by non-parametric statistics (Mann-Whitney test with Benjamini-Hochberg correction). Since the original False Discovery Rate (FDR) methodology is too conservative for genomics applications and results in a substantial loss of power, we used a more relaxed criteria (FDR 0.1). Only those genes with fold change of at least 2.0 were included in the analysis. Biological significance was assessed using gene ontology, pathway analysis and via GeneCards database. The list of 28 genes was then used to build the model to classify postoperative Group I vs. Group II. We constructed this prediction model on preoperative day −1 gene expression data using the support vector machine (SVM) algorithm. Out of 29 samples, 20 were randomly selected to build the model and the remaining 9 samples, stratified by membership in Group I or Group II, were used to test the model. The prediction model was tested on 25 repetitions with random sampling. Hence, the model was built on a 20×28 matrix. Testing of the model showed prediction of Group I versus Group II membership with 93% accuracy. One-year survival in Group I was 15/17 and in Group II 3/11, indicating lower risk in Group I (Fisher's Exact Test p<0.005). Importantly, the time-to-event Kaplan-Meier survival analysis suggested that the significantly elevated risk of death in Group II vs. Group I continued over the 1-year period following MCS-surgery (log rank p=0.00182).

In one illustrative example, a subject's blood sample is assayed for expression levels of the 12 genes listed in Table 4. The amount of gene expression is determined relative to a reference value. The reference value is the level of a normalization gene (one known NOT to be related to FRP) and/or it can be a level known to be representative of healthy individuals and/or individuals known to recover from heart failure. A neutral score on the 10-point FRP scale would be 5.5. The average fold-change in gene expression would contribute to an increase or decrease from 5.5, depending on whether it was in the direction of change associated with recovery, to arrive at the FRP score for that subject. As shown in Table 4, down-regulation of the first seven genes is associated with recovery from heart failure, while up-regulation of the last five genes is associated with recovery. Optionally, the contribution of each gene's expression level is weighted based on the linear discriminant analysis to adjust for differences amongst genes in their predictive value.

Those skilled in the art will recognize that the FRP scale can be expressed on the basis of other numerical ranges and still operate in the same manner as the 10-point scale described herein. For example, the FRP scale can be a 0-5 point range, a 0-50 point range, or a 0-100 point range. Deviation relative to a neutral midpoint can still be calculated in a manner that is based on the relative expression levels of the genes listed in Tables 1-4, and adjusted to take into account appropriate weighting and other parameters considered predictive of functional recovery.

Kits and Assay Standards

In some embodiments the invention provides kits for measuring gene expression for one or more of the genes provided in Tables 1-4. Some such kits comprise a set of reagents as described herein that specifically bind one or more genes of the invention, and optionally, one or more suitable containers containing reagents of the invention. In some embodiments, reagents herein specifically bind to at least one gene comprising RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, or FITM1. Reagents include molecules that specifically bind one or more genes or gene products of the invention, including primers and probes. Reagents can optionally include a detectable label. Labels can be fluorescent, luminescent, enzymatic, chromogenic, or radioactive.

Kits of the invention optionally comprise an assay standard or a set of assay standards, either separately or together with other reagents. An assay standard can serve as a normal control by providing a reference level of normal expression for a given marker that is representative of a healthy individual.

Kits can include probes for detection of alternative gene expression products The kit can optionally include a buffer. While some embodiments use the NGS-platform, other embodiments use qPCR/Nanostring/Nanopore technology.

In some embodiments the invention provides for the establishment of one or more central laboratories to which patient blood samples can be shipped for assay using polymerase chain reaction (PCR), next generation sequencing (NGS), or other gene expression profiling assay for one or more of the genes provided in Tables 1-4.

Computer Implementations

Figure 2:
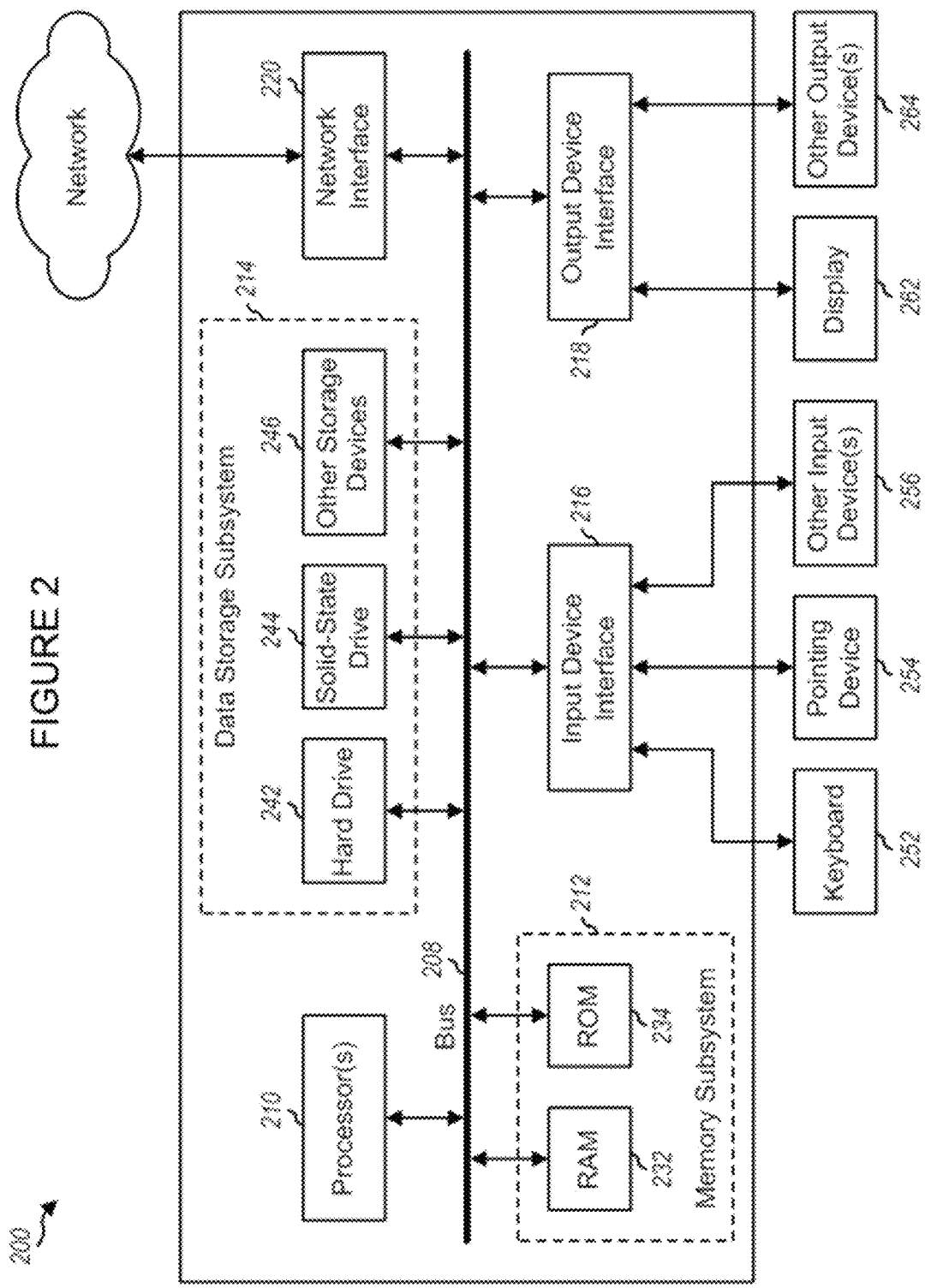
FIG. 2 is a block diagram of an embodiment of a computer system that can be used to implement a method as described herein.

Provided herein, in certain aspects, are computer implemented systems for use in methods herein, such as methods of treatment, methods of gene expression profiling, and methods of recommending a treatment (FIG. 2). In some embodiments, computer implemented systems herein comprise: (a) a sample receiver for receiving a sample provided by an individual; (b) a digital processing device comprising an operating system configured to perform executable instructions and a memory; and (c) a computer program including instructions executable by the digital processing device to provide a treatment to a healthcare provider based on the sample. In some embodiments, the computer program comprises: (i) an gene analysis module configured to determine a gene expression level in the sample for at least one gene comprising RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, or FITM1; (ii) a treatment determination module configured to determine the treatment based on the gene expression level; and (iii) a display module configured to provide the treatment to the healthcare provider.

The invention provides a non-transitory computer-readable medium encoded with computer-executable instructions for performing the methods described herein. In another embodiment, the invention provides a non-transitory computer-readable medium embodying at least one program that, when executed by a computing device comprising at least one processor, causes the computing device to perform one or more of the methods described herein. In some embodiments, the at least one program contains algorithms, instructions or codes for causing the at least one processor to perform the method(s). Likewise, the invention provides a non-transitory computer-readable storage medium storing computer-readable algorithms, instructions or codes that, when executed by a computing device comprising at least one processor, cause or instruct the at least one processor to perform a method described herein.

Those of ordinary skill in the art would understand that the various embodiments of the method described herein, including analysis of gene expression profiles, generation of FRP scores, and prediction of outcomes, for example, can be implemented in electronic hardware, computer software, or a combination of both (e.g., firmware). Whether the present method is implemented in hardware and/or software may depend on, e.g., the particular application and design constraints imposed on the overall system. Ordinary artisans can implement the present method in varying ways depending on, e.g., particular application and design constraints, but such implementation decisions do not depart from the scope of the present disclosure.

The computer programs/algorithms for performing the present method can be implemented with, e.g., a general-purpose processor, a digital signal processor (DSP), an application-specific integrated circuit (ASIC), a field-programmable gate array (FPGA), or other programmable logic device, discrete gate or transistor logic, discrete hardware components, or any combination thereof designed to perform the functions and steps described herein. A general-purpose processor can be a microprocessor, but alternatively the processor can be any conventional processor, controller, microcontroller or state machine. A processor can also be implemented as a combination of computing devices, e.g., a combination of a DSP and a microprocessor, a plurality of microprocessors, one or more microprocessors in conjunction with a DSP core, or any other such configuration.

The steps of the present method, or the computer programs/algorithms for performing the method, can be embodied directly in hardware, in a software module executed by a processor, or in a combination of hardware and software (e.g., firmware). A software module can reside in, e.g., RAM memory, flash memory, ROM memory, EPROM memory, EEPROM memory, registers, a hard drive, a solid-state drive, a removable disk or disc, a CD-ROM, or any other form of storage medium known in the art. An exemplary storage medium is coupled to the processor such that the processor can read information from, and write information to, the storage medium. Alternatively, the storage medium can be integral to the processor. The processor and the storage medium can reside in, e.g., an ASIC, which in turn can reside in, e.g., a user terminal. In the alternative, the processor and the storage medium can reside as discrete components in, e.g., a user terminal.

In one or more exemplary designs, the functions for carrying out the method described herein can be implemented in hardware, software, firmware or any combination thereof. If implemented in software, the functions can be stored on or transmitted over a computer-readable medium as instructions or codes. Computer-readable media include without limitation computer storage media and communication media, including any medium that facilitates transfer of a computer program/algorithm from one place to another. A storage medium can be any available medium that can be accessed by a general-purpose or special-purpose computer or processor. As a non-limiting example, computer-readable media can comprise RAM, ROM, EEPROM, CD-ROM or other optical disc storage, magnetic disk storage or other magnetic storage devices, or any other medium that can be used to carry or store a computer program/algorithm in the form of instructions/codes and/or data structures and that can be accessed by a general-purpose or special-purpose computer or processor. In addition, any connection is deemed a computer-readable medium. For example, if the software is transmitted from a website, a server or other remote source using a coaxial cable, fiber optic cable, twisted pair, digital subscriber line (DSL), or a wireless technology such as infrared, radio wave or microwave, then the coaxial cable, fiber optic cable, twisted pair, DSL, or wireless technology such as infrared, radio wave or microwave are computer-readable media. Discs and disks include without limitation compact disc (CD), laser disc, optical disc, digital versatile disc (DVD), blu-ray disc, hard disk and floppy disk, where discs normally reproduce data optically using a laser, while disks normally reproduce data magnetically. Combinations of the above are also included within the scope of computer-readable media.

The methods described herein can be automated. Accordingly, in some embodiments the method is implemented with a computer system (e.g., a server, a desktop computer, a laptop, a tablet or a smartphone) comprising at least one processor. The computer system can be configured or provided with algorithms, instructions or codes for performing the method which are executable by the at least one processor. The computer system can generate a report containing information on any or all aspects relating to the method, including results of the analysis of the biological sample from the subject. The disclosure further provides a non-transitory computer-readable medium encoded with computer-executable instructions for performing the present method.

FIG. 2 is a block diagram of an embodiment of a computer system 200 that can be used to implement a method as described herein. System 200 includes a bus 208 that interconnects major subsystems such as one or more processors 210, a memory subsystem 212, a data storage subsystem 214, an input device interface 216, an output device interface 218, and a network interface 220. Processor(s) 210 perform many of the processing functions for system 200 and communicate with a number of peripheral devices via bus 208.

Memory subsystem 212 can include, e.g., a RAM 232 and a ROM 234 used to store codes/instructions/algorithms and data that implement various aspects of the present method. Data storage subsystem 214 provides non-volatile storage for program codes/instructions/algorithms and data that implement various aspects of the present method, and can include, e.g., a hard disk drive 242, a solid-state drive 244, and other storage devices 246 (e.g., a CD-ROM drive, an optical drive, a removable-media drive, and so on). Memory subsystem 212 and/or data storage subsystem 214 can be used to store, e.g., the gene expression profile and the FRP score of subjects, and the therapeutic outcome of treatment of those subjects with a particular AdHF or other intervention. The codes/instructions/algorithms for implementing certain aspects of the present method can be operatively disposed in memory subsystem 212 or stored in data storage subsystem 214.

Input device interface 216 provides interface with various input devices, such as a keyboard 252, a pointing device 254 (e.g., a mouse, a trackball, a scanner, a pen, a tablet, a touch pad or a touch screen), and other input device(s) 256. Output device interface 218 provides an interface with various output devices, such as a display 262 (e.g., a CRT or an LCD) and other output device(s) 264. Network interface 220 provides an interface for computer system 200 to communicate with other computer systems coupled to a network to which system 200 is coupled.

Other devices and/or subsystems can also be coupled to computer system 200. In addition, it is not necessary for all of the devices and subsystems shown in FIG. 2 to be present to practice the method described herein. Furthermore, the devices and subsystems can be interconnected in configurations different from that shown in FIG. 2.

EXAMPLES

The following examples are presented to illustrate the present invention and to assist one of ordinary skill in making and using the same. The examples are not intended in any way to otherwise limit the scope of the invention.

Example 1: Association Between Preoperative PBMC Gene Expression Profiles, Early Postoperative Organ Function Recovery Potential, and Long-Term Survival in Advanced Hearth Failure Patients Undergoing Mechanical Circulatory Support This Example demonstrates that preoperative PBMC-GEP predicts early changes in organ function scores and correlates with long-term outcomes in AdHF patients following MCS implantation. Therefore, gene expression lends itself to outcome prediction and warrants further studies in larger longitudinal cohorts.

Heart failure (HF) is a complex clinical syndrome that results from any structural or functional cardiovascular disorder causing a mismatch between demand and supply of oxygenated blood and consecutive failure of the body's organs. In the United States, HF affects about 6 million persons [1]. HF with reduced ejection fraction (HFrEF) affects 3 million people [2]. The lifetime risk of developing HF for men and women older than 40 years of age is 1 in 5. The death rate remains unacceptably high at approximately 50% within 5 years from time of initial diagnosis. Stage D, or advanced heart failure (AdHF), designates patients with truly refractory HF (estimated at 300,000 persons in the US annually) [2].

AdHF patients may benefit from the following therapeutic options: optimal medical management (OMM) or palliative/hospice care (PC, n=300,000), mechanical circulatory support (MCS, n=30,000) or heart transplantation (HTx, n=3,000) [3]. MCS devices, originally used for patients with AdHF as a bridge-to-transplant or bridge-to-recovery, are now increasingly used as destination (lifelong) therapy and have the potential to outnumber HTx by a factor of 1:10, currently showing an improved survival rate of approximately 80% at 1 year [4].

Because of this success, destination MCS is increasingly being offered to patients with challenging clinical profiles. There is significant patient-to-patient variability for risk of adverse events, including death, after MCS-surgery. The ability to preoperatively predict this risk for the individual AdHF-patient before surgery and the impact of this risk on the associated long-term survival prognosis would be a very important component of clinical decision-making and management. Currently, we have our clinical expertise and validated clinical tools [4-18] for risk prediction.

However, despite our clinical expertise and validated tools, it is not easy to assess this risk and, therefore, make recommendations about which therapy benefits the individual patient most with respect to long-term survival. Often, elderly and frail AdHF patients, if not doing well on OMM, are also at increased risk for organ dysfunction (OD) and death after MCS-surgery. One of the reasons for the current challenges of risk prediction is the difficulty in assessing the degree of frailty and OD in the individual AdHF patient who often suffers from malnutrition, immune dysfunction, and poor infection coping potential.

Preoperative HF-related immunologic impairment is a component of poor outcomes after MCS and HTx, owing to the known associations between increased age, T cell and innate immune cell dysfunction, frailty, increased numbers of terminally differentiated T cells, immune senescence (deficient replicative ability), and immune exhaustion (impaired antigen response) [19-23]. Multi-organ dysfunction syndrome (MOD) is one of the leading causes of morbidity and mortality. It is associated with grossly aberrant immune activation [4-18, 24-26].

None of the current established clinical scoring and prediction tools integrate immune function parameters. They have the tendency to be imprecise in estimating risk among severely ill patients [11, 12], making the therapeutic recommendation with the best survival estimate for the individual patient very difficult. Our central postulate is that OD and patient death after MCS- or HTx-surgery results from innate and adaptive immune cell dysfunction. Therefore, our goal is to use leukocyte immune-biology information to develop a preoperative test, which would precisely predict postoperative outcomes in the individual AdHF patient. We utilized the widely accepted Sequential Organ Failure Assessment (SOFA) [27] and Model of End Stage Liver Disease without INR (MELD-XI) [24, 28, 29] scores as quantitative assessment tools to interpret the PBMC data and to develop a predictive leukocyte biomarker.

In order to achieve this goal, we hypothesize that in AdHF patients undergoing MCS-surgery, HF-related preoperative peripheral blood mononuclear cell (PBMC) gene expression profiles (GEP) correlate with and predict changes of early postoperative organ function status as surrogates for 1 year survival.

In our prior studies, we reported on PBMC GEP time course analyses after MCS-surgery [30-32]. Here, we present data to support our hypotheses that, in AdHF patients undergoing MCS implantation, preoperative differential PBMC-GEP are associated with and are predictive of early postoperative SOFA and MELD-XI score changes, defined as score difference between immediately before surgery to 8 days after surgery as a surrogate marker for long term mortality risk.

The findings support the concept of developing a Functional Recovery Potential (FRP), seen as a person's quantifiable potential to improve after being exposed to a stressor, such as MCS-surgery.

Methods & Design

Study Design

To address the most pressing clinical problem of MCS-related perioperative MOD [4, 33, 34], we chose to base this analysis on a control population of AdHF-patients undergoing MCS-surgery alone. We conducted a study with 29 AdHF patients undergoing MCS-surgery at UCLA Medical Center between August 2012-2014 under UCLA Medical Institutional Review Board 1 approved Protocol Number 12-000351. Written informed consent was obtained from each participant.

Clinical Management.

All study participants were referred to the UCLA Integrated AdHF Program and evaluated for the various therapeutic options, including OMM, MCS, and HTx. All patients were optimized regarding HF therapy, consented to and underwent MCS-therapy according to established guidelines [35, 36], based on the recommendations of the multidisciplinary heart transplant selection committee.

After anesthesia induction, patients were intubated and placed on cardiopulmonary bypass. The type of MCS-device selected depended on the acuity and severity of the heart failure syndrome, as well as patient characteristics [37]. For left ventricular support, patients underwent either Heartmate II (HeartMate II® pumps are valveless, rotary, continuous flow pumps) or HVAD (HeartWare® HVAD pumps are valveless, centrifugal, continuous flow pumps). For biventricular support, patients underwent either Centrimag-BVAD (Centrimag® pumps are valveless, centrifugal, continuous flow pumps that are external to the body), PVAD biventricular assist device (BVAD) (Thoratec® Paracorporeal Ventricular Assist Device (PVAD) pumps each contain two mechanical tilting disk valves) or the t-TAH (the Temporary Total Artificial Heart consists of two artificial ventricles that are used to replace the failing heart).

Various combinations of cardiovascular inotropic and vasoactive drugs were used to support patient's hemodynamics postoperatively, tailored to the individual requirements. In addition, other temporary organ system support was administered as required (e.g. mechanical ventilation, hemodialysis, blood transfusions, and antibiotic therapy).

Clinical Phenotyping.

Demographic variables were obtained for all patients. Twelve distinct parameters were collected on a daily basis for time-dependent clinical phenotyping of the patient cohort, which included serum bilirubin, serum creatinine, leukocyte count, platelet count, alveolar oxygen pressure, fraction of inspired oxygen (FiO2), mean systemic arterial pressure (MAP), INR (International Normalized Ratio, for prothrombin time), blood glucose, heart rate, respiratory rate, temperature, and the Glasgow Coma Scale (GCS).

Using combinations of these parameters, we also calculated two validated and commonly used composite OD scores, SOFA [27] and MELD-XI [24]. The SOFA score is a validated and widely accepted measure that rates degree of organ failure across six major organ systems (cardiovascular, respiratory, neurological, renal, hepatic, and coagulation). The MELD-XI score is a variation of the MELD score that uses only the bilirubin and creatinine levels, and eliminates the INR, which is typically not interpretable in these patients given the need of anticoagulation.

We also used the Interagency Registry for Mechanically Assisted Circulatory Support (INTERMACS) scoring system, which has been developed to improve patient selection and timing of MCS therapy [4] for preoperative HF-severity assessment. Higher INTERMACS risk categories are considered predictors of worse survival. While INTERMACS identifies clinical outcomes and risk of MOD, it does not provide insights into the underlying immunological mechanisms of disease.

Clinical Outcome Parameter.

One of the most significant clinical outcome parameters for AdHF patients undergoing MCS is the probability of organ function improvement from one day before to eight days after surgery.

From a clinical utility perspective, we aim to provide AdHF-patients with the most precise prediction of short- and long-term outcome [38, 39] on either OMM or MCS. Since many AdHF patients have varying recovery potential, we chose a short-term improvement criteria, i.e. 8 days postoperatively, as a surrogate outcome parameter for long-term survival. For these reasons, we chose not to use a static preoperative organ function severity score to develop our biomarker. The most logical clinical parameter is the potential for organ function improvement, which we named the short-term functional recovery potential (FRP). This parameter may identify patients who benefit from aggressive therapies, such as MCS, even if they are very ill.

Therefore, patients were grouped into two organ failure risk strata: Group I=improving (both SOFA and MELD-XI scores improve from day −1 to day 8) and Group II=not improving (SOFA and/or MELD-XI score(s) do not improve from day −1 to day 8). In other words, if the MCS-surgery improves the hemodynamic situation without complications, then the patient's organ function is expected to recover by postoperative day 5 and clearly by postoperative day 8, which should be reflected in a concordant improvement of SOFA and MELD-XI score, from day −1 to day 8. On the other hand, if SOFA or MELD-XI, or both, scores do not improve from day −1 to day 8, we hypothesize that this problem may potentially impact long-term survival.

PBMC sample processing & GEP protocol.

PBMC samples were collected one day before surgery (day −1). Clinical data was collected on day −1 and day 8 postoperatively. We chose, based on our successful Allomap™ biomarker test development experience [40-43], to focus on the mixed PBMC population.

Eight ml of blood was drawn into a CPT tube (Becton Dickinson, Franklin Lakes, N.J.). Peripheral Blood Mononuclear cells (PBMC) from each sample were purified within 2 h of phlebotomy. The collected blood was mixed and centrifuged at room temperature (22° C.) for 20 min at 3000 RPM. Two ml of plasma was separated without disturbing the cell layer into an eppendorf tube (Sigma-Aldrich, St. Louis, Mo.) and stored at −80° C. for future experiments. The cell layer was collected, transferred to 15 ml conical tubes and re-suspended in cold Phosphate Buffer Saline (PBS) (Sigma-Aldrich, St. Louis, Mo.) and centrifuged for 20 min at 1135 RPM at 4° C. The supernatant was aspirated and discharged. The cell pellet was re-suspended in cold PBS, transferred into an eppendorf tube and centrifuged for 20 min at 5.6 RPM at 4° C. The supernatant was discharged. The pellet was re-suspended in 0.5 ml RNA Protect Cell Reagent (Qiagen, Valencia, Calif.) and frozen at −80° C.

PBMC Transcriptome RNA Sequencing.

All samples were processed using next-generation RNA sequencing transcriptome analysis at the UCLA Technology Center for Genomics & Bioinformatics. Briefly, the RNA was isolated from the PBMC using RNeasy Mini Kit (Qiagen, Valencia, Calif.). The quality of the total RNA was assessed using NanoDrop® ND-1000 spectrophotometer (NanoDrop Technologies, Wilmington, Del.) and Agilent 2100 Bioanalyzer (Agilent Technologies, Palo Alto, Calif.) concentration above 50 ng/µl., purity—260/280~2.0., integrity—RIN>9.0 and average>9.5. Then, mRNA library was prepared with Illumina TruSeq RNA kit according to the manufacturer's instructions (Illumina, San Diego, Calif.). Library construction consists of random fragmentation of the polyA mRNA, followed by cDNA production using random polymers. The cDNA libraries were quantitated using Qubit and size distribution was checked on Bioanalyzer 2100 (Agilent Technologies, Palo Alto, Calif.). The library was sequenced on HiSeq 2500. Clusters were generated to yield approximately 725K-825K clusters/mm2. Cluster density and quality was determined during the run after the first base addition parameters were assessed. We performed single end sequencing runs to align the cDNA sequences to the reference genome. Generated FASTQ files were transferred to the AdHF Research Data Center where Avadis NGS 1.5 (Agilent, Palo Alto, Calif. and Strand Scientific, CA) was used to align the raw RNA-Seq FASTQ reads to the reference genome. After RNA extraction, quantification and quality assessment, total mRNA was amplified and sequenced on the whole-genome Illumina HiSeq 2500. Data was then subjected to DeSeq normalization using NGS Strand/Avadis (v2.1 Oct. 10, 2014). Batch effects were removed using the ComBat algorithm in R [44].

Statistical Analysis

Transcriptome Analysis.

We were interested in finding the preoperatively differentially expressed genes (DEG) in the GEP of 29 patients, as they correlate to early postoperative organ function improvement as markers for long-term survival outcome. PBMC-genes differentially expressed between Group I and Group II were identified by non-parametric statistics (Mann-Whitney test with Benjamini-Hochberg correction). Since the original False Discovery Rate (FDR) methodology [45] is too conservative for genomics applications and results in a substantial loss of power [46], we used a more relaxed criteria (FDR 0.1) values as an exploratory guide for which entities to investigate further. Only those genes with fold change of at least 2.0 were included in the analysis. Biological significance was assessed using gene ontology, pathway analysis and via GeneCards database.

Prediction Model Building and Testing.

To classify postoperative Group I vs. Group II, we constructed a PBMC-GEP prediction model on preoperative day −1 gene expression data using the support vector machine (SVM) algorithm. Out of 29 samples, 20 were randomly selected to build the model and the remaining 9 samples, stratified by membership in Group I or Group II, were used to test the model. The prediction model was tested on 25 repetitions with random sampling.

Quantitative Real-Time Polymerase Chain Reaction (RT-qPCR) Validation.

NGS data were validated by Quantitative PCR obtained from PBMC of 6 samples taken across Group I (n=3) and Group II (n=3). Total RNA from PBMC were purified using RNeasy Mini Kit (Qiagen, Valencia, Calif.). CDNA was synthesized with iScript supermix for RT-qPCR (BioRad, Hercules, Calif.). RT-qPCR analysis was carried out with iTaq SYBR green supermix (BioRad, Hercules, Calif.) on the 7500 Fast Real-time PCR system (Applied Biosystems, Foster City, Calif.). GAPDH levels were used as an internal control for RT-qPCR. Sequences of the primer pairs used were as follows: GAPDH-f: CCACTCCTCCACCTTTGAC (SEQ ID NO: 1); GAPDH-r: ACCCTGTTGCTGTAGCCA (SEQ ID NO: 2); KIR2DL4-f: ACCCACTGCCTGTTTCTGTC (SEQ ID NO: 3); KIR2DL4-r: ATCACAGCATGCAGGTGTCT (SEQ ID NO: 4); NAPSA-f: CAGGACACCTGGGTTCACAC (SEQ ID NO: 5); NAPSA-r: GGTTGGACTCGATGAAGAGG (SEQ ID NO: 6); BATF2-f: AAAGGCAGCTGAAGAAGCAG (SEQ ID NO: 7); BATF2-r: TCTTTTTCCAGAGACTCGTGC (SEQ ID NO: 8); ANKRD22-f: CTCAGCCAGGAAGGATTTTG (SEQ ID NO: 9); ANKRD22-r: TGATAGGCTGCTTGGCAGAT (SEQ ID NO: 10).

Results

Clinical Profiles and Outcomes

Pre-, Intra- and Postoperative Clinical Profiles and Long-Term Survival.

Figures 3A, 3B:
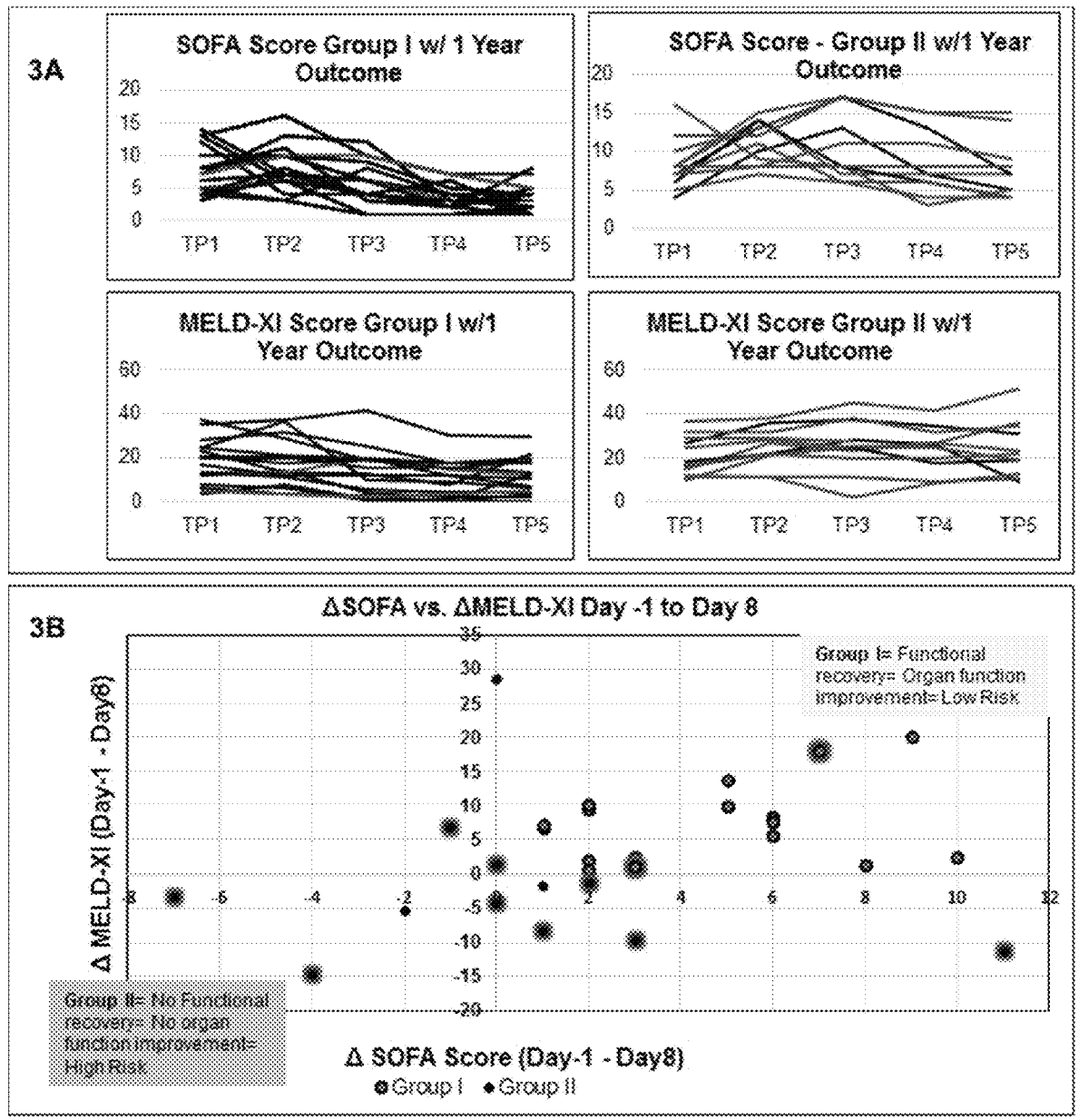
FIGS. 3A-3B illustrate organ function and outcomes.
Figure 4:
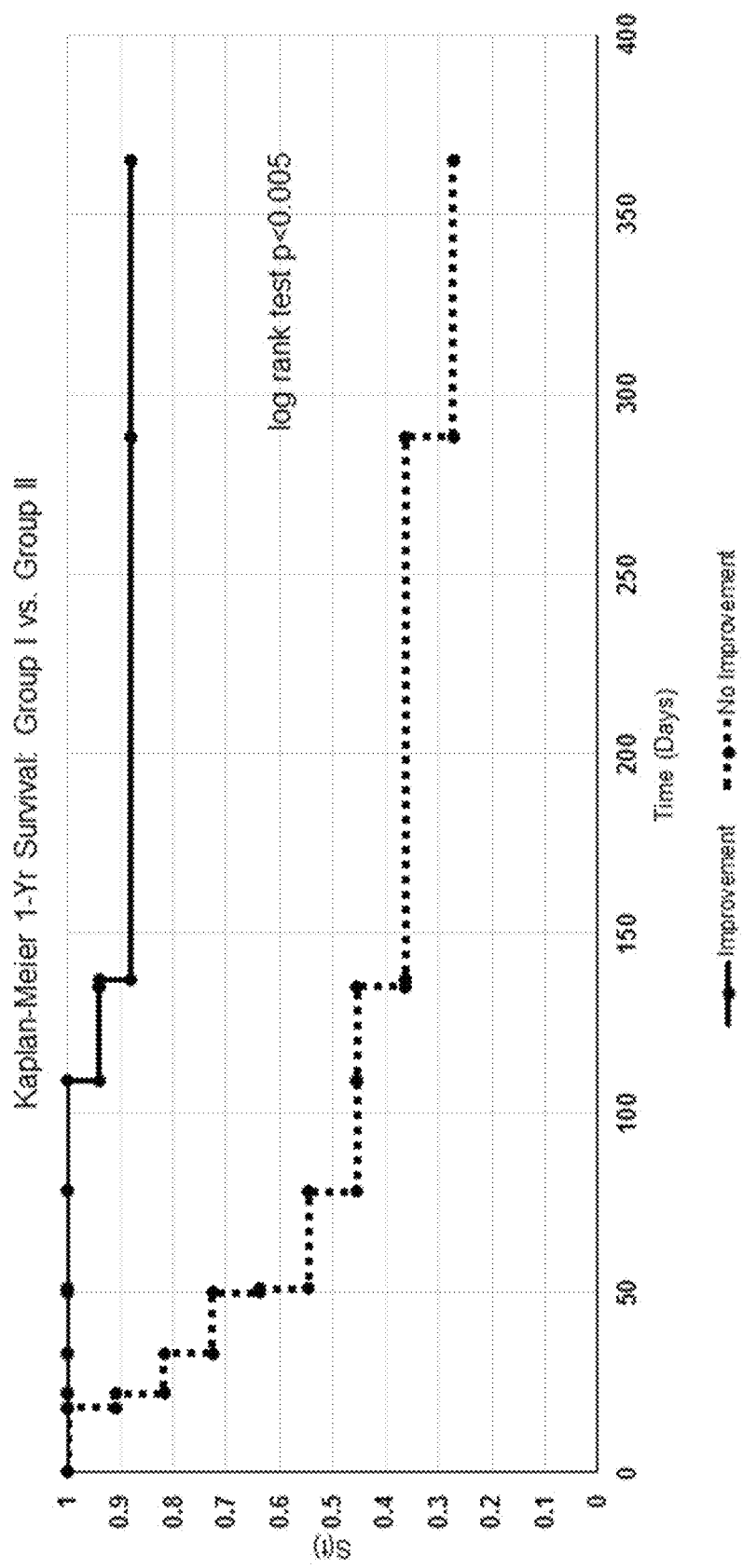
FIG. 4 shows the Kaplan-Meier 1-year survival in Group I vs. Group II.

Out of 29 patients, 17 were preoperatively in INTERMACS class 1-2 (a state of critical cardiogenic shock or progressively declining on inotropic support), while the remaining 12 patients were in INTERMACS class 3-4 (inotrope dependent or resting symptoms) [4]. Characteristics of the patients are shown in Table 1 of Bondar, G. et al., 2017, PLoS ONE 12(12): e0189420. The SOFA and MELD-XI OD trajectory for each group is summarized in FIG. 3A. The same data in terms of amount of improvement is shown in FIG. 3B. One-year survival in Group I was 15/17 and in Group II 3/11, indicating lower risk in Group I (Fisher's Exact Test p<0.005). Importantly, the time-to-event Kaplan-Meier survival analysis suggested that the significantly elevated risk of death in Group II vs. Group I continued over the 1-year period following MCS-surgery (log rank p=0.00182; FIG. 4).

Neither correlation between preoperative clinical variables (i.e. INTERMACS class, SOFA median score, MELD-XI median score, and Seattle Heart Failure Model, excluding respiratory rate) nor intra/postoperative clinical variables predict Group I versus Group II membership or year 1 survival status. We grouped preoperative right ventricular function, defined by echocardiographic criteria, into two groups: normal to mildly reduced right ventricular function (n=12) and moderately to severely reduced right ventricular function (n=17). The chi-square p-value for postoperative Group I versus II membership was non-significant (p=0.42). We grouped preoperative inotrope support levels into the following categories: no inotrope (n=7), 1 inotrope (n=3), 2 inotropes (n=11), inotropes or MCS (e.g. VA ECMO) (n=8). The chi-square p-value for postoperative Group I versus II membership was non-significant (p=0.61). Additional preoperative clinical information data (i.e. bilirubin, creatinine, international normalized ratio, white blood cells, heart rate, and glucose level, all non-significant chi-square p-value) (respiratory rate, p=0.03) are also summarized in Table 1. None of the 29 patients had a clinical infection episode on the day prior to MCS surgery.

The intraoperative median cardiopulmonary bypass (CPB) time was 107 min (25%/75%: 75 min/145 min). We categorized patient CPB time into two groups: patients with no CPB (e.g. minimally invasive LVAD-placement) or CPB time shorter than the median time (n=15) and patients with CPB time equal to or longer than the median time (n=14). The chi-square p-value for Group I versus II membership was non-significant (p=0.51). Additionally, the group without major intraoperative bleeding (n=20) was compared to those patients with major bleeding (n=9). Bleeding severity was defined per INTERMACS criteria as greater than or equal to 4 RBC per any 24 h period during the first 8 postoperative days. The chi-square p-value for postoperative Group I versus II membership was non-significant (p=0.06).

Out of 11 patients who died postoperatively, 9 patients died from MOD, 1 patient from gastro-intestinal hemorrhage and 1 patient from sepsis.

Correlation Between Preoperative PBMC-Transcriptome and Clinical Outcomes

PBMC-Transcriptome and Clinical Course.

Out of 29 patients undergoing MCS-surgery, 17 were in Group I and 12 in Group II. Twenty-eight MCS-surgery patients were alive 8 days postoperatively. Since our study explored how the preoperative PBMC-transcriptome can predict postoperative clinical outcomes, we restricted our analysis to the relationship between preoperative day −1 PBMC data and change of clinical data from preoperative day −1 to postoperative day 8. This project is based on our previously published studies that characterized the postoperative correlation between PBMC GEP and clinical parameters [30, 31], as well as our time-course analysis of the correlation between PBMC GEP module eigengenome and clinical parameters [32].

Preoperative PBMC-Transcriptome and Early Postoperative Organ Function Changes.

Figure 5A:
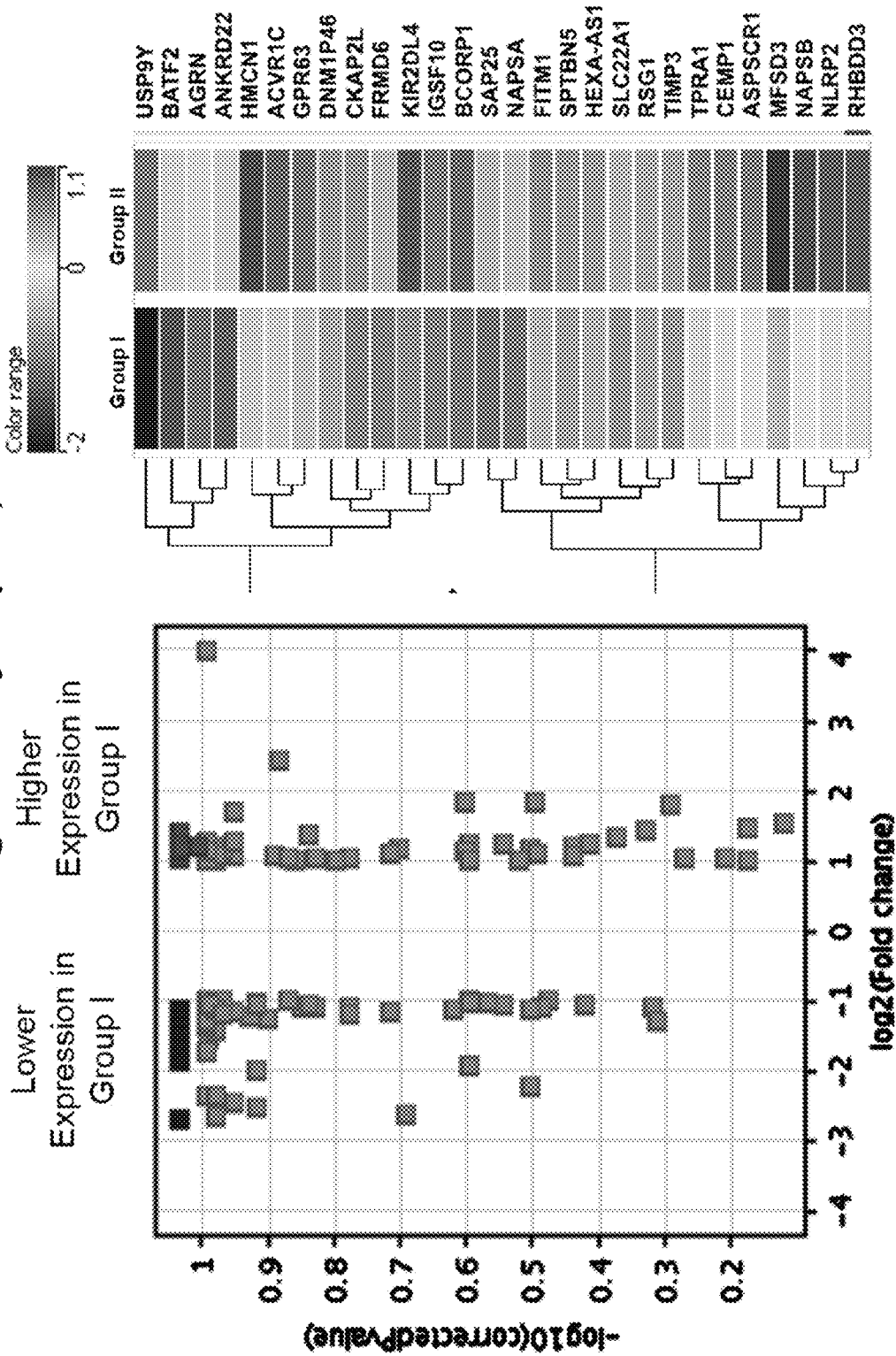
FIGS. 5A-5C show overlap of significant genes associated with organ function improvement and survival benefit. The indicated color range in FIGS. 5A and 5B corresponds to the differential expression, ranging from blue (−2) to gray, to yellow (0), to orange, to red (1.1).

In order to identify day −1 transcripts related to organ function change, the entire set of mRNA transcripts (36,938) was filtered (20th-100th percentile) [44]. Of the resulting 26,571 entities, only those with a fold change of at least 2.0 (123 transcripts) were retained for statistical analysis with the unpaired Mann-Whitney test and Benjamini-Hochberg correction analysis (FDR=0.1). After these filtering steps, 28 genes were identified as differentially expressed between the two groups on day −1 (FIG. 5A, Table 5).

Preoperative PBMC-Transcriptome and 1-Year Outcome.

Figure 5B:
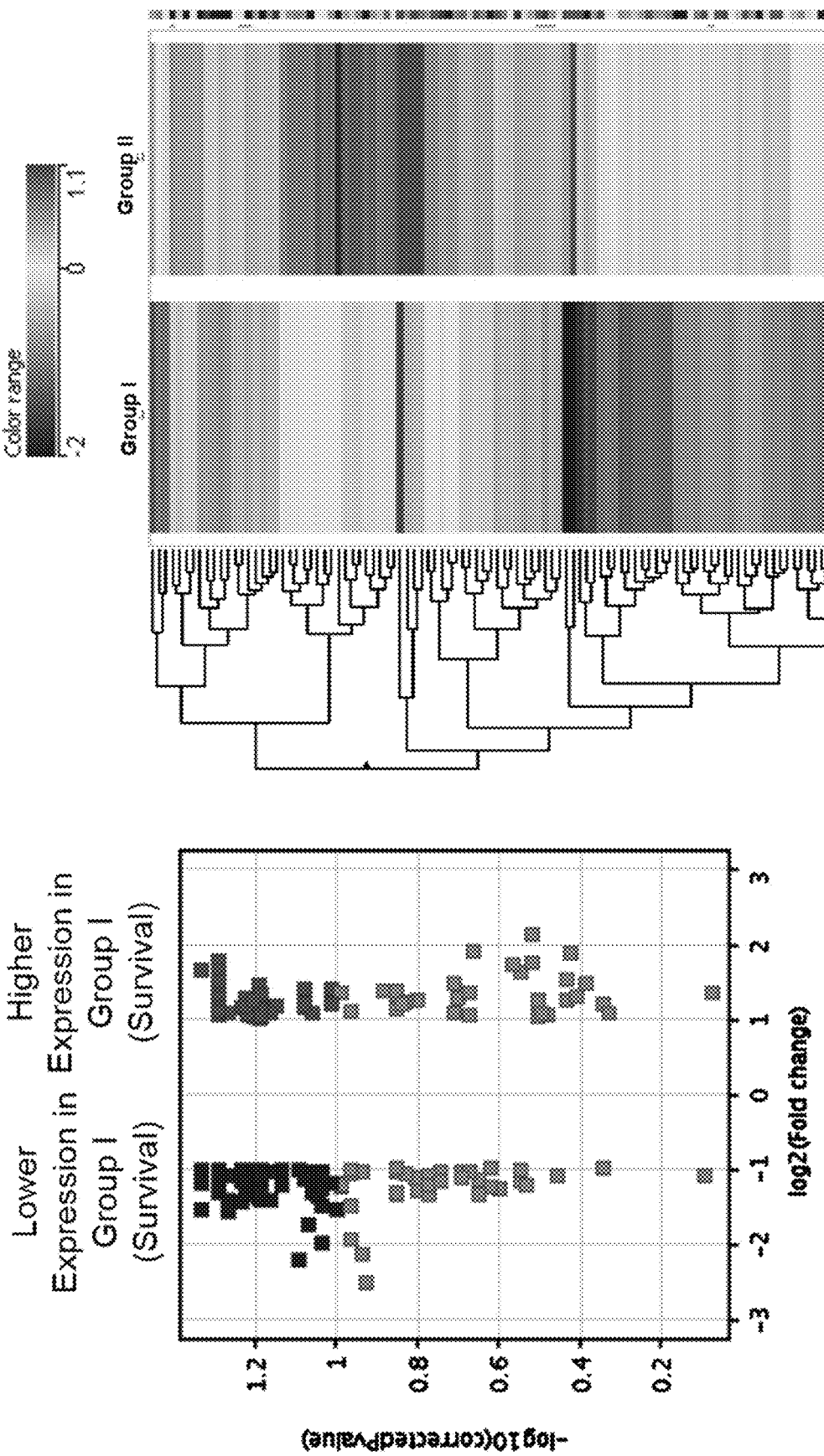
Figure 5C:
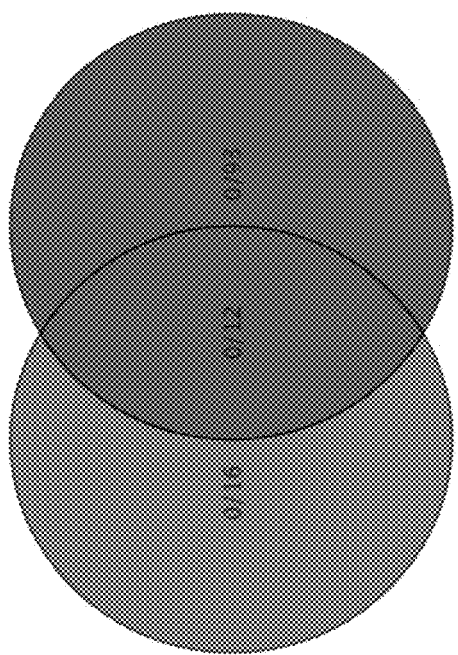

Eighteen out of 29 patients were alive after 1 year while 11/29 died during year 1. The causes of death are summarized in Table 1 of Bondar, G. et al. 2017. The preoperative GEP was different in year 1 survivors and non-survivors. The filtered 25,319 entities were analyzed using 2.0 fold change criteria. The 177 differentially expressed genes were analyzed by unpaired Mann-Whitney test with Benjamini-Hochberg correction, resulting in 105 transcripts (FDR=0.1). Hierarchical clustering was used on the 105 differentially expressed genes (Corresponding 105 genes in Table 4B and publication Bondar et al 2017) for the year 1 survival patients (FIG. 5B). Out of these genes, 12 overlap with the 28 genes that correlated with day 8 organ function improvement (FIG. 5C, Table 5).

Out of the 28 genes that were differentially expressed between the two groups (Group I vs Group II membership) on postoperative day 8, 12 genes overlapped with 1-year survival status (blue rows).

TABLE 5

Known Function of 28 Gene Classifier

| ENTREZ ID | Gene Symbol | Fold Change | GROUP I | GROUP II | p-value | p (corr) with FDR | Gene Summary |
|---|---|---|---|---|---|---|---|
| 8287 | USP9Y | −6.442405 | DOWN | UP | 0.01792041 | 0.09173012 | USP9Y is associated to Ubiquitin-Proteasome Dependent Proteolysis, and essential component of TGF-beta/BMP signaling cascade. Within nondiabetic heart failure-associated genes with ischemic cardiomyopathy, it was shown to have a high degree of upregulation |
| 116071 | BATF2 | −2.2702124 | DOWN | UP | 0.01606008 | 0.09173012 | BATF2 controls the differentiation of lineage-specific cells in the immune system. Following infection, participates in the differentiation of CD8(+) thymic conventional dendritic cells in the immune system. Selectively suppresses |

TABLE 5-continued

Known Function of 28 Gene Classifier

| ENTREZ ID | Gene Symbol | Fold Change | GROUP I | GROUP II | p-value | p (corr) with FDR | Gene Summary |
|---|---|---|---|---|---|---|---|
| | | | | | | | CYR61/CCN1 transcription and hence blocks the downstream cell proliferation signals produced by CYR61 and inhibits CYR61-induced anchorage-independent growth and invasion in several cancer types; IFNs, apart from their function as antiviral infection agents, exert a variety of inhibitory effects on cell growth, apoptosis, and angiogenesis. IFNs induce growth inhibition by a variety of pathways that involve many IFN-stimulated genes BATF2 is one of these genes and can be induced by IFNb, which indicates that BATF2 may be a key component involved in IFN signaling. |
| 375790 | AGRN | −2.2644913 | DOWN | UP | 0.0173365 | 0.09173012 | AGRN is responsible for the maintenance of neuromuscular junction (NMJ) and directs key events in postsynaptic differentiation |
| 118932 | ANKRD22 | −2.685126 | DOWN | UP | 0.02013588 | 0.09173012 | ANKRD22 shows the highest upregulation with a value of 3.06 in the RT-qPCR analysis in finding diagnostic biomarkers in Pancreatic Adenocarcinoma Patients. The function of ANKRD22 remains unknown, but it has been patented by Rosenthal et al. as a possible biomarker for several types of cancer and by Brichard et al. for identification of the patient response to cancer immunotherapy |
| 83872 | HMCN1 | −2.608948 | DOWN | UP | 0.00819846 | 0.09173012 | HMCN1 encodes a large extracellular member of the immunoglobulin superfamily it is associated with Age-Related and Postpartum Depression |
| 130399 | ACVR1C | −2.2228224 | DOWN | UP | 0.00538353 | 0.09173012 | ACVR1C is a type I receptor for the TGFB, Plays a role in cell differentiation, growth arrest and apoptosis. |
| 81491 | GPR63 | 2.2556078 | DOWN | UP | 0.00260203 | 0.09173012 | GPR63 is a G-protein coupled receptor activity and plays a role in brain function. |
| 196968 | DNM1P46 | −2.2071562 | DOWN | UP | 0.00731407 | 0.09173012 | DNM1P46 is a pseudogene. Although not fully functional, pseudogenes may be functional, similar to other kinds of noncoding DNA, which can perform regulatory functions. |
| 150468 | CKAP2L | −2.7842844 | DOWN | UP | 0.00412917 | 0.09173012 | CKAP2L is a microtubule-associated protein. |
| 122786 | FRMD6 | −2.4180312 | DOWN | UP | 0.00285335 | 0.09173012 | FRMD6 is a Protein Coding gene. Among its related pathways are Cytoskeletal Signaling and Hippo signaling pathway |
| 3805 | KIR2DL4 | −3.4912138 | DOWN | UP | 0.00362563 | 0.09173012 | KIR2DL4 is part of the killer cell immunoglobulin-like receptors (KIRs) which are transmembrane glycoproteins expressed by natural killer cells and subsets of T cells. Inhibits the activity of NK cells thus preventing cell lysis. Unlike classic HLA class I molecules, HLA-G does not seem to possess significant immune stimulatory functions, and even responses directed against allogeneic HLA-G have not been reported. HLA-G, however, possesses the capability common to HLA class I molecules, to bind inhibitory receptors (FIG. 1C). |

TABLE 5-continued

Known Function of 28 Gene Classifier

| ENTREZ ID | Gene Symbol | Fold Change | GROUP I | GROUP II | p-value | p (corr) with FDR | Gene Summary |
|---|---|---|---|---|---|---|---|
| 285313 | IGSF10 | −3.154924 | DOWN | UP | 0.00996186 | 0.09173012 | Three HLA-G receptors have been described: ILT2/CD85j/LILRB1 (ILT2), ILT4/CD85d/LILRB2 (ILT4), and KIR2DL4/CD158d (KIR2DL4) IGSF10 (Immunoglobulin Superfamily Member 10) is a Protein Coding gene |
| 286554 | BCORP1 | −3.629981 | DOWN | UP | 0.0200527 | 0.09173012 | BCORP1 is a pseudogene. Although not fully functional, pseudogenes may be functional, similar to other kinds of noncoding DNA, which can perform regulatory functions. |
| 100316904 | SAP25 | 2.371788 | UP | DOWN | 0.00694567 | 0.09173012 | SAP25 is a new member of the growing family of nucleocytoplasmic shuttling proteins that are located in PML nuclear bodies. PML nuclear bodies are implicated in diverse cellular functions such as gene regulation, apoptosis, senescence, DNA repair, and antiviral response. Involved in the transcriptional repression |
| 9476 | NAPSA | 2.1895149 | UP | DOWN | 0.01598942 | 0.09173012 | NAPSA is a pronapsin A which may have considerable diagnostic value as a marker for primary lung cancer. In contrast, the pronapsin B gene, which lacks an in-frame stop codon and so may be a transcribed pseudogene, is expressed at comparable levels in normal human spleen, thymus, cytotoxic and helper Tlymphocytes, natural killer (NK) cells and Blymphocytes; may also function in protein catabolism |
| 161247 | FIT1 | 2.272873 | UP | DOWN | 0.00938506 | 0.09173012 | FIT1 in skeletal muscle and FIT2 in adipose, it is interesting to speculate that FIT1 might be essential for the rapid oxidation of FAs stored as TG in LDs while FIT2 is required for the longterm storage of TG in adipocytes. Plays an important role in lipid droplet accumulation. |
| 51332 | SPTBN5 | 2.3029516 | UP | DOWN | 0.01434127 | 0.09173012 | SPTBN5 is related to pathways of Interleukin-3, 5 and GM-CSF signaling and Signaling by GPCR |
| 80072 | HEXA-AS1 | 2.1215222 | UP | DOWN | 0.01862884 | 0.09173012 | SPTBN5 (Spectrin Beta, Non-Erythrocytic 5) is a Protein Coding gene. HEXA-AS1 (HEXA Antisense RNA 1) is an RNA Gene, and is affiliated with the antisense RNA class. |
| 6580 | SLC22A1 | 2.033342 | UP | DOWN | 0.0173365 | 0.09173012 | SLC22A1 (Solute Carrier Family 22 Member 1) is a Protein Coding gene. Plays a critical for elimination of many endogenous small organic cations as well as a wide array of drugs and environmental toxins |
| 79363 | RSG1 | 2.0549338 | UP | DOWN | 0.00735565 | 0.09173012 | Differential expression of ABCA1, RSG1 and ADBR2 was replicated in monocyte gene expression in patients with early onset coronary artery disease (CAD). These three genes identified expressed differently in CAD cases which might play a role in the pathogenesis of atherosclerotic vascular disease. Potential effector of the planar cell polarity signaling pathway. |
| 7078 | TIMP3 | 2.2165775 | UP | DOWN | 0.0200527 | 0.09173012 | TIMP3 blocks the binding of VEGF to VEGF receptor-2 and inhibits downstream signaling and angiogenesis. This property seems to be independent of its MMP-inhibitory activity, indicating a new function for this molecule. |

TABLE 5-continued

Known Function of 28 Gene Classifier

| ENTREZ ID | Gene Symbol | Fold Change | GROUP I | GROUP II | p-value | p (corr) with FDR | Gene Summary |
|---|---|---|---|---|---|---|---|
| 131601 | TPRA1 | 2.0833867 | UP | DOWN | 0.01276787 | 0.09173012 | Complexes with metalloproteinases (such as collagenases) and irreversibly inactivates them by binding to their catalytic zinc cofactor. Diseases associated with TIMP3 include Sorsby Fundus Dystrophy and Pseudoinflammatory TPRA1 whose physiological functions are unknown, was first cloned as a GLP-1 receptor homolog in 3T3-L1 adipocytes and is also expressed in tissues whose development requires Hh signaling, including heart, brain, lung, pancreas, and muscle |
| 752014 | CEMP1 | 2.0399396 | UP | DOWN | 0.01435211 | 0.09173012 | CEMP1 (Cementum Protein 1) is a Protein Coding gene. Diseases associated with CEMP1 include Coccidiosis. |
| 79058 | ASPSCR1 | 2.0533528 | UP | DOWN | 0.01435211 | 0.09173012 | ASPSCR1 encodes a protein that contains a UBX domain and interacts with glucose transporter type 4 (GLUT4). This protein is a tether, which sequesters the GLUT4 in intracellular vesicles in muscle and fat cells in the absence of insulin, and redistributes the GLUT4 to the plasma membrane within minutes of insulin stimulation |
| 113655 | MFSD3 | 2.3885236 | UP | DOWN | 0.00672813 | 0.09173012 | Membrane-bound solute carriers (SLCs) are essential as they maintain several physiological functions, such as nutrient uptake, ion transport and waste removal. The SLC family comprise about 400 transporters, and two new putative family members were identified, major facilitator superfamily domain containing 1 (MFSD1) and 3 (MFSD3). |
| 256236 | NAPSB | 2.6573431 | UP | DOWN | 0.01610727 | 0.09173012 | NAPSB is a pseudogene. Although not fully functional, pseudogenes may be functional, similar to other kinds of noncoding DNA, which can perform regulatory functions. |
| 55655 | NLRP2 | 2.3330774 | UP | DOWN | 0.01434127 | 0.09173012 | NLRP2 suppresses TNF- and CD40-induced NFKB1 activity at the level of the IKK complex, by inhibiting NFKBIA degradation induced by TNF. When associated with PYCARD, activates CASP1, leading to the secretion of mature proinflammatory cytokine IL1B. May be a component of the inflammasome, a protein complex which also includes PYCARD, CARD8 and CASP1 and whose function would be the activation of pro-inflammatory caspases. |
| 25807 | RHBDD3 | 2.2666128 | UP | DOWN | 0.02240318 | 0.09841397 | Rhbdd3, a member of the rhomboid family of proteases, suppressed the activation of DCs and production of interleukin 6 (IL-6) triggered by Toll-like receptors (TLRs). Rhbdd3-deficient mice spontaneously developed autoimmune diseases characterized by an increased abundance of the TH17 subset of helper T cells and decreased number of regulatory T cells due to the increase in IL-6 from DCs" |

PBMC-GEP Prediction Model Development

Clinical Profiles and Outcome Correlation.

Figure 6:
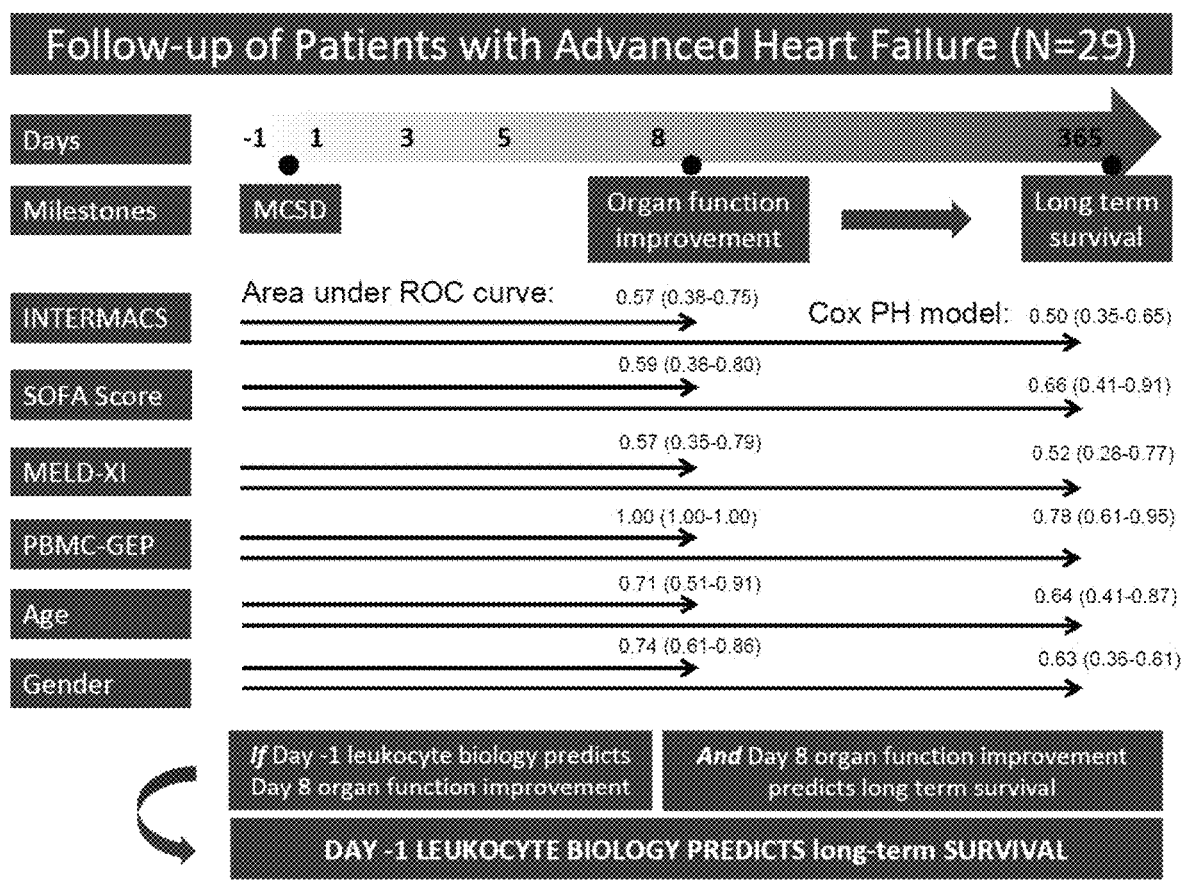
FIG. 6 shows an exemplary prediction biomarker development rationale.

Neither preoperative clinical variables including INTERMACS [4] class, SOFA median score, MELD-XI median score, and Seattle Heart Failure Model (SHFM) nor intra/postoperative clinical variables (except for respiratory rate) predict Group I versus Group II membership nor year 1 survival status. On day 8, 17 patients had organ function improvement (Group I) and 12 patients had no organ function improvement (Group II), with one died on postoperative day 3. Nine patients in INTERMACS class 1-2 preoperatively improved at day 8, while 8 patients did not improve (Fisher's Exact Test p<0.005). Eight patients in INTERMACS class 3-4 improved while 4 did not improve (FIG. 6). The inefficiency of clinical scores in correlating with OD in critically ill AdHF patients [10] supports our rationale in developing a preoperative biomarker prediction test.

Prediction of Early Postoperative Organ Function Changes.

We built a model using the SVM algorithm by randomly selecting 20 samples out of 29 total, stratified by membership in Group I versus Group II. To test the model, the remaining 9 samples were stratified by membership in Group I or Group II. An average prediction accuracy of 93% (range: 78-100%) was achieved after running the model building process 25 times (Table 6).

TABLE 6

Prediction of Organ Function Improvement Group I vs II.

| | Run Accuracy % |
|---|---|
| PM1 | 100 |
| PM2 | 100 |
| PM3 | 100 |
| PM4 | 89 |
| PM5 | 89 |
| PM6 | 78 |
| PM7 | 100 |
| PM8 | 89 |
| PM9 | 89 |
| PM10 | 89 |
| PM11 | 100 |
| PM12 | 100 |
| PM13 | 100 |
| PM14 | 100 |
| PM15 | 89 |
| PM16 | 100 |
| PM17 | 89 |
| PM18 | 100 |
| PM19 | 100 |
| PM20 | 89 |
| PM21 | 89 |
| PM22 | 100 |
| PM23 | 100 |
| PM24 | 89 |
| PM25 | 89 |
| Average | 94 |

Out of 29 samples, 20 were randomly selected, stratified by membership in Group I or Group II, were used to build the model and the remaining 9 samples were used to test the model.

RT-qPCR Validation.

To validate the NGS results in this study, we performed a limited RT-qPCR experiment to assay the 4 highest ranked genes (by statistical significance and correlation between Group I and Group II expression levels). Results show that 2 out of 4 genes (KIR2DL4, BATF2) concordantly correlated between NGS and RT-qPCR expression levels, showing downregulation in Group I and upregulation in Group II. Those 2 genes therefore might become candidates for the prognostic test development. The RT-qPCR results of ANKRD22 and NAPSA expression level showed an equivocal relationship to the NGS results. We attributed this discrepancy to the difference in method. This result is in agreement with the internal validation during the Allomap™ test development, in which 68 out of 252 candidate genes discovered by high-throughput technology were confirmed by concordant expression changes using RT-qPCR. Therefore, these 68 genes were retained for further Allomap™ test development.

FIGS. 3A-3B. illustrate organ function and outcomes. FIG. 3A shows organ function and outcomes of 29 patients across five time points. Out of 29 AdHF-patients undergoing MCS-surgery, 17 patients had organ function improvement from preoperative day −1 (TP1) to day 8 (TP5) (Group I) and 12 patients had no organ function improvement (Group II). Each black line represents one 1-year survivor while each red line represents one 1-year non-survivor. In each group, non-survivors are shown in red. FIG. 3B shows that, out of 29 AdHF-patients undergoing MCS-surgery, 17 patients improved (Group I, upper right quadrant) and 12 patients did not improve (Group II, remaining 3 quadrants) from day −1 (TP1) to day 8 (TP5). Each large dark bullet represents one patient who died within one year. Absence of improvement of either score was associated with reduced 1-year survival.

FIG. 4 show the Kaplan-Meier 1-year survival in Group I vs. Group II. In the 17 patients who improved (Group I=Functional recovery=Organ function improving=Low Risk) vs. the 11 patients who did not improve (Group II=No functional recovery=Organ function not improving=High Risk), the time-to-event Kaplan-Meier survival analysis suggested that the significantly elevated risk (log rank test p=0.00182) of death in Group II continued over the 1-year period following MCS-surgery.

FIGS. 5A-5C show overlap of significant genes associated with organ function improvement and survival benefit. FIG. 5A shows hierarchical clustering of significant genes day −1 (TP1). Left: The Volcano plot of 28 genes, which are differentially expressed between Group I and Group II. Right: Hierarchical clustering of the 28 candidate genes for the prediction test demonstrates the differential gene expression between Group I and Group II. FIG. 5B shows hierarchical clustering of genes associated with survival benefit. Left: The Volcano plot of 105 genes, which are differentially expressed between Group I and Group II. Right: Hierarchical clustering 17 of the 105 candidate genes for the prediction test demonstrates the differential gene expression between Group I=Survival, Group II=Non-survival. FIG. 5C shows overlap genes from both improvement group and 1-year survival outcome. Left: Venn-Diagram shows the 28 DEGs identified in the comparison by Improvement Score (red) and the Right shows the 105 DEGs identified by comparing 1-Year Survival (blue). 12 DEGs were shared across the two comparisons. Right: The 12 overlap genes.

FIG. 6 shows an exemplary prediction biomarker development rationale. Preoperative clinical heart failure/organ function severity scores (INTERMACS class, SOFA median score, MELD-XI median score) and demographics (age, gender) did not reliably discriminate postoperative organ function improvement (ROC, 95% confidence interval) and long term survival (Cox Proportional Hazard Model, 95% confidence interval). In contrast, the PBMC-GEP correlates well with postoperative organ function improvement and long term survival.

Discussion

We present data to support our hypotheses that in AdHF patients undergoing MCS implantation, preoperative differential PBMC-GEP are associated with and are predictive of early postoperative SOFA and MELD-XI score changes. We defined these clinical parameters as the difference in score between one day before surgery and 8 days after surgery as a surrogate marker for long-term mortality risk. Our studies show the set of 28 genes derived from preoperative PBMC GEP is predictive of early postoperative improvement or non-improvement of SOFA and MELD-XI scores. Out of the 28 preoperative genes, the following 12 genes are of specific biological interest due to their overlap in differentiating early postoperative organ function improvement and year 1 survivor status.

Potential Biological Implications of Overlapping Genes

Hypothetical Mechanisms of Up-Regulated Genes in Non-Improvement of SOFA Score and MELD-XI Score and Year 1 Non-Survivors.

BATF2 belongs to a class of transcription factors that regulate various immunological functions and control the development and differentiation of immune cells. Functional studies demonstrated a predominant role for BATF2 in controlling Th2 cell functions and lineage development of T lymphocytes. Following infection, BATF2 participates in the development of and differentiation of CD8 (+) thymic conventional dendritic cells in the immune system [47]. BATF2 plays a key component involved in IFN signaling and positive regulation of immune responses by altering expression of cytokines and chemokines. Therefore, it possibly maintains the balance in inflammatory processes. BATF2 is an essential transcription factor for gene regulation and effector functions in classical macrophage activation [48]. AGRIN is a gene with a ubiquitous role and is evolutionarily conserved in the extracellular matrix (ECM) [49]. Its intracellular processes include proliferation, apoptosis, migration, motility, autophagy, angiogenesis, tumorigenesis, and immunological responses [50, 51]. AGRIN interacts with the α/ρ-dystroglycan receptor in the formation of immunological synapses with lymphocytes and aids in activation [52] as well as maintaining monocyte cell survival downstream in an α-dystroglycan dependent manner [53]. The AGRIN LG3 domain has been used as a biomarker for detection of prematurely ruptured fetal membranes [54]. ANKR22, involved in the lipid modification of proteins [55], has been patented as a possible biomarker for several types of cancers [56, 57] to identify patient responses to cancer immunotherapy. FRMD6 has been linked to various complex diseases, such as asthma, Alzheimer's disease, and lung cancer. It plays a critical role in regulating both cell proliferation and apoptosis, where it is thought to have tumor suppressor properties. FRMD6 may help mediate the process by which Vitamin D inhibits the proliferation of immune cells [58, 59]. Upregulation of FRMD6 has been suggested as a prognostic marker in colorectal cancer [59]. KIR2DL4 codes for transmembrane glycoproteins expressed by natural killer (NK) cells and subsets of T cells. KIR2DL4 inhibits the activity of NK cells and may reduce activation induced cell death in these T cells in Sézary syndrome [60], [61, 62]. KIR2DL4 is an unusual member of the KIR family that recognizes human leukocyte antigen G and mediates NK-cell activation [63] and has been suggested as a useful diagnostic biomarker of neoplastic NK-cell proliferations [64].

Hypothetical mechanisms of down-regulated genes in non-improvement of SOFA score and MELD-XI score and year 1 non-survivors.

SAP25 is a member of the nucleocytoplasmic shuttling proteins that are located in promyelocytic leukemia (PML) nuclear bodies. PML nuclear bodies are implicated in diverse cellular functions, such as gene regulation, apoptosis, senescence, DNA repair, and antiviral response [65], [66, 67]. NAPSA is a pronapsin gene, which may have a considerable diagnostic value as a marker for primary lung cancer. NAPSA was detected in a subset of poorly differentiated papillary thyroid carcinomas and anaplastic carcinomas [68]. TIMP3 is an extracellular matrix-bound protein, which regulates matrix composition and affects tumor growth. TIMP3 suppresses tumor inactivation in cancer by mechanisms of invasion and angiogenesis [69]. TIMP-3 downregulation is associated with aggressive non-small cell lung cancer and hepatocarcinoma cells, as compared with less invasive and/or normal lung and liver cells [70]. It mediates vascular endothelial growth factor (VEGF) by blocking the binding of VEGF to VEGF receptor-2, inhibiting downstream signaling, and prevents angiogenesis. These inhibitive properties seem to be independent of its matrix metalloproteinases (MMP)-inhibitory activity, which indicates a new function for this molecule. RHBDD3 is a member of the rhomboid family of proteases that suppresses the activation of dendritic cells (DCs) and production of interleukin 6 (IL-6) triggered by Toll-like receptors. The rhomboid proteins are involved in signaling via the receptor for epidermal growth factor, mitochondrial homeostasis and parasite invasion [71, 72]. RHBDD3 negatively controls the activation of DCs and maintains the balance of regulatory T cells and TH17 cells by inhibiting the production of IL-6 by DCs, thus contributing to the prevention of autoimmune diseases [72].

In summary, our central postulate is that OD and death after MCS- or HTx-surgery results from innate and adaptive immune cell dysfunction. Therefore, leukocyte immune-biology information may be used to develop a preoperative test, which more precisely predicts postoperative outcomes in the individual AdHF-patient. To meet this clinical goal, we have developed a novel concept of FRP, which is based on our assessment that the key prognostic information is the preoperative potential to postoperatively restore an equilibrium rather than the absolute magnitude of preoperative OD. In this clinical context, we interpret the potential biological role of the 12 overlap genes as follows: we hypothesize BATF2 is chronically more activated in GROUP II AdHF-patients in comparison to GROUP I patients. BATF2 activation is due to its attempts to repair the cell necrosis-mediated damage caused by OD. This hyper-activation leads to exhaustion of adaptive immunity cells, which may explain the protracted time-course-to-death in Group II patients. (FIG. 4). To garner support for this hypothesis, we have initiated a study that incorporated multiplex flow cytometry markers, cell free methylated DNA, and mitochondrial DNA into the study protocol. For RHBDD3, its downregulation in patients with rheumatoid arthritis, ulcerative colitis and Crohn's disease [72] may be beneficial in preventing auto-immune aggression. However, its downregulation in AdHF-patients undergoing MCS-surgery might exacerbate an inappropriate innate inflammatory response and inappropriate adaptive immune-incompetence via a less inhibitory effect on the IL6-pathway [73]. Furthermore, it is interesting to note that upregulation of genes, such as ANKRD22, FRMD6, and KIR3DL2, and downregulation of genes, such as TIMP3, SAP25, NAPSA, and TIM P are associated with a worse prognosis in cancer, are also associated with a worse prognosis in AdHF. This raises the question about common pathways in both clinical syndromes.

Health System Implication Perspectives.

Our data suggest that the preoperative dynamic recovery potential, rather than the static severity of OD, is the key prognostic property to restoring equilibrium after surgery. This also presents the possibility of using a preoperative blood sample to identify AdHF-patients who may have a high chance of early postoperative recovery and a potentially good long-term prognosis. If the preoperative blood test result predicts a high FRP (Group I), this data might lead to the recommendation to undergo surgery. If the preoperative blood test suggests a low FRP (Group II), the healthcare team may avoid a potentially harmful recommendation of surgery at that time. In the US, we estimate that out of 30,000-60,000 individuals per year with AdHF and potential candidates for MCS, at least 7,500-15,000 might not benefit from undergoing surgery based on the test results if they are too sick to benefit from MCS surgery. Since HF is a major public health concern due to its tremendous societal and economic burden, with estimated costs in the U.S. of $37.2 billion in 2009 and with expectations to increase to $97.0 billion by 2030, our proposed prediction test would simultaneously allow to tailor the individual patient's personal benefits and also enhance cost-effectiveness in U.S. healthcare.

The clinical decision-making challenge at the time of AdHF evaluation often culminates in the choice between modern medicine and compassionate end of life care. This ultimate scenario is demanding medically, ethically and economically. It deserves the best evidence-based decision making support that personalized precision medicine research has to offer that lives up to the highest humanistic expectations that society entrusts us with.

Limitations.

First, our outcome parameter in this proof-of-principle study used a dichotomous endpoint (Improvement versus No Improvement of organ function on day 8 postoperatively). In a planned expansion of the study to include a larger cohort, we will treat the outcome parameter as a quantitative continuous variable. Second, we have not incorporated multisystem level protein markers into our analysis. In a planned extension of the project, we will include multiplex flow cytometry and cytokine parameters. Third, the study had a small sample size. This poses inherent limitations on Group I vs Group II comparisons. The logistic regression/Cox-PH models were constructed with only one predictor variable each due to sample size constraints. We also reported the coefficients/accuracy measures from these models with 95% confidence intervals, which properly reflect our uncertainty about the parameter estimates as a function of sample size. Fourth, the RT-qPCR validation was limited by a lack of biological material necessary to complete the test. We will expand this validation to include all candidate genes in a follow-up study. Fifth, as in translational biomarker development in general, many results were a consequence of operator/researcher-dependent decisions. Sixth, while we chose to base our analysis on AdHF-patients undergoing MCS-surgery alone to address the problem of MCS-related perioperative MOD [4, 33, 34], we acknowledge that we have not addressed aspects of the PBMC-biology related to MCS-surgery intervention versus general heart surgery. In order to address this question, we have initiated a follow-up project examining AdHF-cohorts undergoing OMM, HTx, coronary artery bypass surgery, percutaneous coronary interventions, valve replacement, valve repair, arrhythmia interventions and healthy volunteers, utilizing the same study protocol. These results will be reported separately.

CONCLUSIONS

In AdHF patients undergoing MCS implantation, the postoperative clinical improvement of OD within one week of surgery is associated with reduced long-term mortality and a PBMC GEP that differs from that of patients who do not improve, is already present preoperatively and may lend itself to outcome prediction. The underlying mechanisms and prognostic implications to improve patient outcomes warrant further study in larger longitudinal cohorts.

REFERENCES

1. Yancy C W, et al. 2013 ACCF/AHA Guideline for the Management of Heart Failure. A Report of the American College of Cardiology Foundation/American Heart Association Task Force on Practice Guidelines. 2013; 62(16): e147-e239. pmid:23747642
2. Hunt S A, et al. 2009 Journal of the American College of Cardiology. 2009; 53(15):e1-e90. Epub 2009/04/11. pmid:19358937.
3. Weiss J N, et al. Circulation research. 2012; 111(4):493-504. Epub 2012/08/04. pmid:22859671.
4. Kirklin J K, et al. The Journal of heart and lung transplantation: the official publication of the International Society for Heart Transplantation. 2014; 33(6):555-64. Epub 2014/05/27. pmid:24856259.
5. Troughton R W, et al. Lancet (London, England). 2000; 355(9210):1126-30. pmid:10791374.
6. Gardner R S, et al. European heart journal. 2003; 24(19): 1735-43. pmid:14522568.
7. Doust J A, et al. BMJ. 2005; 330(7492):625. pmid: 15774989
8. Aaronson K D, et al. Circulation. 1997; 95(12):2660-7. pmid:9193435.
9. Levy W C, et al. Circulation. 2006; 113(11):1424-33. pmid:16534009.
10. Ketchum E S, et al. The Journal of heart and lung transplantation: the official publication of the International Society for Heart Transplantation. 2010; 29(9): 1021-5. pmid:20558086.
11. Sartipy U, et al. European journal of heart failure. 2014; 16(2):173-9. pmid:24464911.
12. Sartipy U, et al. Journal of the American Heart Association. 2014; 3(3):e000998. pmid:24906370.
13. Martinez-Selles M, et al. Revista espanola de cardiologia. 2009; 62(4):409-21. pmid:19401126.
14. Flint K M, et al. Circulation Heart failure. 2012; 5(2): 286-93. pmid:22438521.
15. Smits J M, et al. The Journal of Heart and Lung Transplantation. 32(9):873-80. pmid:23628111
16. Chyu J, et al. Circulation Heart failure. 2014; 7(1):88-95. pmid:24281135.
17. Cowger J, et al. Journal of the American College of Cardiology. 2013; 61(3):313-21. pmid:23265328.
18. Kormos R L, et al. The Journal of thoracic and cardiovascular surgery. 2010; 139(5):1316-24. pmid:20132950.
19. Wherry E J. T cell exhaustion. Nature immunology. 2011; 12(6):492-9. pmid:21739672
20. Burton D G, et al. Age. 2015; 37(2):27. pmid:25787341.
21. Dorshkind K, et al. Nature reviews Immunology. 2009; 9(1):57-62. pmid:19104499

22. Dunlay S M, et al. The Journal of Heart and Lung Transplantation. 33(4):359-65. pmid:24486165
23. Larbi A, et al. Cytometry Part A. 2014; 85(1):25-35. pmid:24124072
24. Kamath P S, et al. Hepatology (Baltimore, Md.). 2001; 33(2):464-70. Epub 2001/02/15. pmid:11172350.
25. Osler T, et al. Journal of Trauma and Acute Care Surgery. 1997; 43(6):922-6. 00005373-199712000-00009.
26. Knaus W A, et al. Critical care medicine. 1985; 13(10): 818-29. pmid:3928249.
27. Vincent J L, et al. Intensive care medicine. 1996; 22(7):707-10. Epub 1996/07/01. pmid:8844239.
28. Matthews J C, et al. Circulation. 2010; 121(2):214-20. pmid:20048215.
29. Abe S, et al. PloS one. 2014; 9(6):e100618. pmid:24955578.
30. Sinha A, et al. Human immunology. 2010; 71(2):164-9. Epub 2009/11/03. pmid:19879911.
31. Bondar G, et al. PloS one. 2014; 9(12):e115097. pmid:25517110.
32. Wisniewski N, et al. BMC Medical Genomics. 2017; 10(1):52. pmid:28851355
33. Deng M C, et al. Circulation. 2001; 103(2):231-7. pmid:11208682.
34. Deng M C, et al. The Journal of heart and lung transplantation: the official publication of the International Society for Heart Transplantation. 2005; 24(9): 1182-7. pmid:16143231.
35. Feldman D, et al. The Journal of heart and lung transplantation: the official publication of the International Society for Heart Transplantation. 2013; 32(2):157-87. Epub 2013/01/29. pmid:23352391.
36. Adigopula S, et al. Cardiology clinics. 2014; 32(1):73-93, viii. Epub 2013/11/30. pmid:24286580.
37. Deng M C, Naka Y. Mechanical Circulatory Support Therapy In ADVANCED HEART FAILURE. 2007.
38. Deng M C, et al. Comparative Outcome and Clinical Profiles in Transplantation (COCPIT) Study Group. BMJ. 2000; 321(7260):540-5. pmid:10968814.
39. Deng MC. Journal of the American College of Cardiology. 2004; 43(5):803-5. pmid:14998620
40. Deng M C, et al. American journal of transplantation: official journal of the American Society of Transplantation and the American Society of Transplant Surgeons. 2006; 6(1):150-60. Epub 2006/01/26. pmid:16433769.
41. Deng M C, et al. Transplantation. 2014; 97(6):708-14. pmid:24637869.
42. Deng M C. Clinical Transplantation. 2017:e12900-n/a. pmid:28256042
43. Pham M X, et al. The New England journal of medicine. 2010; 362(20):1890-900. Epub 2010/04/24. pmid:20413602.
44. Leek J T, et al. Nat Rev Genet. 2010; 11(10):733-9. pmid:20838408.
45. Benjamini Y, et al. Journal of the Royal Statistical Society Series B (Methodological). 1995; 57(1):289-300.
46. Storey J D, et al. Proceedings of the National Academy of Sciences. 2003; 100(16):9440-5. pmid:12883005
47. Guler R, et al. Oncotarget. 2015; 6(29):26575-82. pmid:26376615.
48. Roy S, et al. Journal of immunology. 2015; 194(12): 6035-44. pmid:25957166.
49. Neill T, et al. Biochemistry. 2015; 54(30):4583-98. pmid:26177309.
50. Iozzo R V. Nat Rev Mol Cell Biol. 2005; 6(8):646-56. pmid:16064139.
51. Iozzo R V, Schaefer L. Matrix Biol. 2015; 42:11-55. pmid:25701227.
52. Zhang J, et al. The FASEB Journal. 2006; 20(1):50-8. pmid:16394267
53. Mazzon C, et al. Blood. 2012; 119(23):5502-11. pmid:22517892
54. Chakraborty S, et al. Nat Commun. 2015; 6:6184. pmid:25630468.
55. Fujiwara Y, et al. Scientific Reports. 2016; 6:23981. pmid:27046665
56. Caba O, et al. Digestive Diseases and Sciences. 2014; 59(11):2714-20. pmid:25069573
57. Baine M J, et al. PloS one. 2011; 6(2):e17014. pmid:21347333.
58. Kariuki S N, et al. PloS one. 2016; 11(7):e0159779. pmid:27454520.
59. Abdul Aziz N A et al. BMC Medical Genomics. 2016; 9(1):58. pmid:27609023
60. Thonnart N, et al. Blood. 2014; 124(22):3330-2. pmid:25414436
61. Rajagopalan S, et al. Science signaling. 2010; 3(110): ra14-ra. pmid:20179272
62. Rajagopalan S, et al. Frontiers in Immunology. 2012; 3(258). pmid:22934097
63. Kucuk C, et al. Am J Pathol. 2016; 186(6):1435-41. pmid:27060228.
64. Ng S-B, et al. The Journal of Pathology. 2011; 223(4): 496-510. pmid:21294123
65. Laitaoja M, et al. Protein Sci. 2016; 25(3):572-86. pmid:26609676.
66. Dellaire G, et al. Bioessays. 2004; 26(9):963-77. pmid:15351967.
67. Shiio Y, et al. Mol Cell Biol. 2006; 26(4):1386-97. pmid:16449650.
68. Schulten H-J, et al. American Journal of Cancer Research. 2016; 6(10):2140-61. pmid:27822408
69. Lui E L, et al. Biomed Pharmacother. 2005; 59 Suppl 2:S363-5. pmid:16507410.
70. Garofalo M, et al. Cancer cell. 2009; 16(6):498-509. pmid:19962668
71. Urban S, et al. Genome biology. 2011; 12(10):231. pmid:22035660.
72. Liu J, et al. Nature immunology. 2014; 15(7):612-22. pmid:24859449.
73. Mann D L. Circulation research. 2002; 91(11):988-98. pmid:12456484.

Example 2: Peripheral Blood Transcriptome Biomarker Test to Diagnose Functional Recovery Potential in Advanced Heart Failure This Example illustrates the outcome prediction obtained by use of the Functional Recovery Potential (FRP), which refers to the potential to recover from stressors based on chronological age and multiple other factors, including primary and secondary organ failure, comorbidities, frailty, disabilities.

Figure 7:
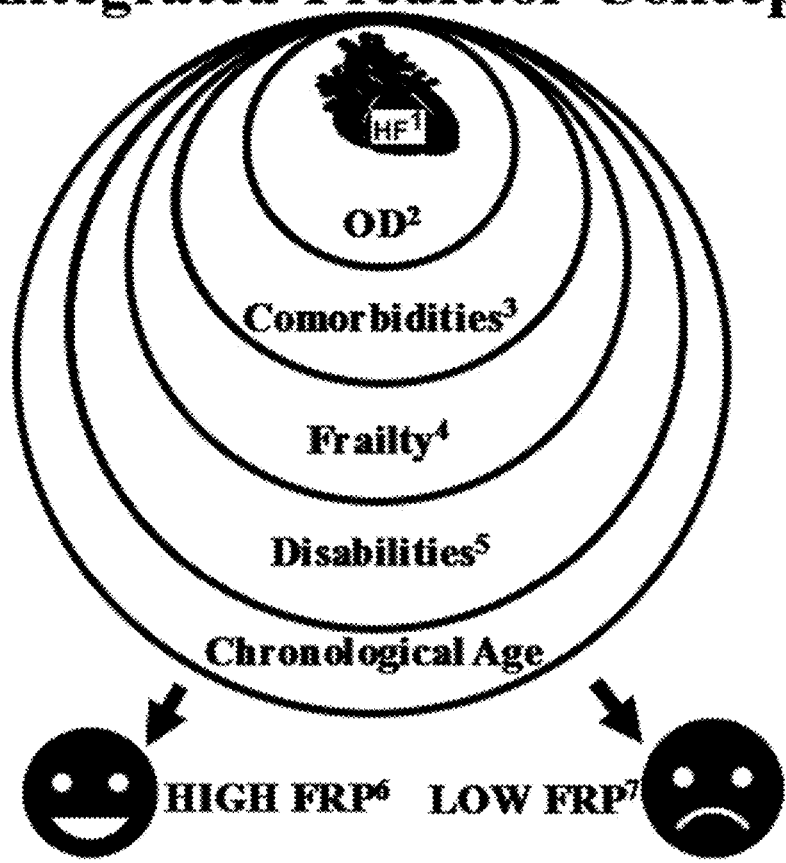
FIG. 7 illustrates the concept of FRP, a clinical composite parameter that can include chronological age as well as personal biological age (measurable by established and validated HF-, OD-, comorbidity-, frailty- and disability-instruments), that represents the instantaneous potential of the person with AdHF to cope with and survive stressors such as AdHF-surgical/interventional therapies, and can be diagnosed by a molecular biomarker.

Heart failure (HF) is a complex clinical syndrome that results from any structural or functional cardiovascular disorder that causes systemic hypoperfusion and failure to meet the body's metabolic demands. HF is initiated by various myocardial injury mechanisms. Despite chronic neurohormonal upregulation in order to maintain a compensated state, further myocardial injury leads to HF progression, resulting in overall catabolic/anabolic imbalance, secondary organ dysfunction, cardiac cachexia, iron deficiency anemia, and frailty[3]. This triggers immune system activation which coincides with progressive dysfunction of the kidneys, liver, bone marrow, brain and metabolism, creating a milieu similar to systemic diseases[4-6], clinically presenting as advanced HF (AdHF) with severely limited prognosis. Outcomes are dependent on HF-severity, but also on chronological age (CA) and multiple other factors jointly called the "Personal Biological Age (PBA)". At any given CA, there are great biological disparities and great heterogeneity in health outcomes[7,8]. This discrepancy relates to a difference in the potential of individual persons to recover from stressors termed the Functional Recovery Potential (FRP), or in equivalent term, the probability of Functional Recovery (FR). Our central postulate is that FRP integrates the clinical composite including CA as well as PBA (primary and secondary organ failure, comorbidities, frailty, disabilities) (FIG. 7).

AdHF patients with low FRP may be at increased risk for death after AdHF-therapies such as mechanical circulatory support (MCS) or heart transplantation (HTx). As described in Example 1, preoperative differential gene expression profiles (GEP) of peripheral blood mononuclear cell (PBMC) are predictive of early postoperative outcomes in AdHF patients undergoing MCS. We defined FRP outcomes as changes of Sequential Organ Failure Assessment (SOFA) and Model of Endstage Liver Disease except INR (MELD-XI) score from preoperatively to 8 days postoperatively, which correlates with long term mortality[9].

FRP is a generalizable and clinically useful concept and can be: 1) defined as a person's potential to return to a functional life, after stressor exposure; 2) modulated by long-term bio-psycho-social interventions; 3) characterized within a general clinical framework integrating CA and PBA data; 4) quantitatively described; 5) used as a surrogate for long-term outcome prediction; and 6) diagnosed from pre-stressor molecular data. Incorporating these molecular data in the clinical encounter can improve the quality of the decision-making in a shared decision-making process and help achieve the value-based healthcare goals of optimizing patient experience, minimizing morbidity and mortality outcomes and maximizing health system cost-effectiveness. In this Example, we discuss the biomedical foundation of FRP and potential clinical utility in HF medicine.

AdHF Outcomes in High-Risk AdHF Patients

During the last five decades, HF outcomes have improved with medical management[1,2,10]. However, patients with stage D, or AdHF, often cannot tolerate optimal medical management (OMM) by guideline directed medical therapy (GDMT) and do not derive the same benefit as patients with less advanced disease[11]. Older patients may not derive the same benefit as younger patients[12].

It has been suggested that biomarker-guided therapy could improve outcomes over solely GDMT[13]. We describe a biomarker to assist the clinician in predicting long-term outcomes after AdHF-surgical/interventional therapies.

Outcomes in AdHF Patients Undergoing Revascularization

For AdHF patients undergoing high risk percutaneous coronary intervention (PCI), the benefits or harms of PCI in HF populations are unknown because of a lack of randomized trials [14].

For AdHF patients undergoing high risk coronary artery bypass surgery (CABG), there is limited information regarding efficacy in different age groups. In the Surgical Treatment for Ischemic Heart Failure (STICH) Study trial, a total 1,212 patients with an left ventricular ejection fraction (LVEF) of <35% were randomly assigned to undergo CABG plus medical therapy or medical therapy alone[15,16]. In the Surgical Treatment for Ischemic Heart Failure Extended Study (STICHES) trial, the median duration of follow-up was 9.8 years. There was a trend towards a smaller reduction in all-cause mortality with CABG compared to GDMT in older compared with younger patients, implying that an improved understanding of the efficacy of CABG in different age groups is needed[14,17]. This result is consistent with recent HF trials[12]. Since there were few patients in the older age groups, the true long-term benefit may be even lower. i.e. there is equipoise between GDMT and CABG in patients>67 years with Heart failure with reduced ejection fraction (HFrEF)[14] (Table 7).

Outcomes in AdHF Patients Undergoing Valve Interventions

AdHF Patients Undergoing Transcatheter Aortic Valve Replacement (TAVR).

Following the initial TAVR experience[18,19] (Table 7), mortality in US clinical practice at 1-year follow-up was 23.7%. It is "imperative to focus on better prediction of the overall risks and benefits of the procedure, particularly given the existing comorbidities of the group of patients being considered for TAVR."[20] (Table 7). In a systematic review on TAVR outcomes, 46.4% and 51.6% of deaths were related to non-cardiovascular causes within and after the first 30 days, respectively[21]. In the Intermediate Risk TAVR trial[22] (Table 7), the guideline for patient inclusion was an Society of Thoracic Surgeons (STS) risk score [102] and EuroSCORE [103], based on the presence of coexisting illnesses to predict mortality at 30 days, between 4-8%[23]. The main results showed that TAVR was not inferior to surgery with respect to outcomes at 2 years (death from any cause or disabling stroke).

Per 2017 recommendations, the risks of death and morbidity associated with the natural history of severe aortic valve stenosis need to be weighed against the risk related to aortic valve replacement as a basis for recommendation of treatment[24,25]. TAVR is not recommended in patients in whom existing comorbidities would preclude the expected benefit from correction of aortic stenosis (AS)[26].

AdHF Patients Undergoing MitraClip.

The overall mortality rate after surgical repair of functional mitral regurgitation (FMR) ranges from 20% to 50% [27-29]. Mitra-Clip therapy is an emerging option for selected high-risk patients with FMR[30,31]. The High Risk Study, an arm of the EVEREST II trial, enrolled symptomatic patients with 3+ to 4+ MR for whom surgical risk for perioperative mortality rate was estimated to be ≥12%, using the STS calculator[32,33]. Potentially qualifying criteria included high-risk patients with porcelain aorta, mobile ascending aorta atheroma, post-mediastinal radiation, functional MR with left ventricular ejection fraction (LVEF) <40%, age older than 75 years with LVEF<40%, previous median sternotomy with patent bypass graft(s), >2 previous chest surgeries, hepatic cirrhosis, or of the following STS high-risk criteria: creatinine level>2.5 mg/dl, previous chest surgery, age older than 75 years, or LVEF<35%[34] (Table 7). A significant number of patients with symptomatic MR have extensive comorbidities or uncertain indications for surgery and are defined as high surgical risk, inoperable or not indicated for surgery, and approximately one-half of patients with symptomatic severe MR may not undergo surgery. In a recent Mitra-Clip-meta-analysis, one-year mortality rate was 16% (408/2498) and similar among groups in patients with FMR vs degenerative mitral regurgitation (DMR). The authors conclude that better patient selection and performing percutaneous edge-to-edge repair at earlier stage could avoid treatment of those patients with advanced LV remodeling, more than severe MR, and many comorbidities, who benefit less from the procedure[35] (Table 7).

Per 2017 American College of Cardiology (ACC)/American Heart Association (AHA) recommendations, transcatheter mitral valve repair may be considered for severely symptomatic patients (New York Heart Association (NYHA) class III to IV) with chronic severe primary MR (stage D) who have favorable anatomy for the repair procedure and a reasonable life expectancy but who have a prohibitive surgical risk because of severe comorbidities and remain severely symptomatic despite optimal GDMT for HF[24].

Outcomes in AdHF Patients Undergoing Ventricular Tachyarrhythmia (VT) Interventions AdHF Patients Undergoing Internal Cardioverter Defibrillator (ICD) Device Therapy.

Patients with stage D heart failure are at increased risk of sudden cardiac death (SCD) from ventricular tachyarrhythmia, thus anti-arrhythmia device therapy is an integral part of their management. Introduction of ICD for primary prevention of sudden cardiac death was proven to be of great benefit with reduction in mortality of 31% in 20 months in patients with history of myocardial infarction (MI) and EF<30%[36]. Furthermore, in patients with EF<35% regardless of etiology and mild to moderate symptoms, ICD implantation decreases mortality by 23% over 5 years [40] [Bardy 2005].

ACC/AHA heart failure guidelines recommend ICD implantation in all patients with ejection fraction of <30% and NYHA class I symptoms and in those with EF<35% with NYHA Class II and III symptoms[2]. However, this therapy is reserved for patients with projected survival of more than one year, which precludes some of the patients with very advanced disease from receiving an ICD. In octogenarians who are due for an ICD, careful thought should be given to the current clinical status, comorbidities, and general frailty prior to considering them for the procedure[38]. Goldenberg et al. highlighted a U-shaped relationship between the severity of heart failure and mortality benefit from ICD therapy[39].

AdHF Patients Undergoing BVPM-Device Therapy.

Cardiac resynchronization therapy (CRT) in patients with wide QRS complex and Left Bundle Branch Block (LBBB) pattern has led to improvement of ventricular contractility and EF, reduction in secondary mitral regurgitation, reversal of remodeling and decrease in mortality. However, around 30% of individuals receiving this therapy derive no benefit or experience worsening of their symptoms[40]. Similar to ICD, patients with stage D HF are often considered to be too sick to benefit from CRT and therefore their treatment is limited to advanced therapies (MCS and Htx) or palliative care[2].

AdHF Patients Undergoing VT-Ablation Therapy.

Ventricular tachycardia (VT)-ablation therapy has increased in the US, specifically in patients worsening clinical risk profile including age and comorbidity burden [41]. In a contemporary registry, catheter ablation of VT in patients with structural heart disease results in 70% freedom from VT recurrence, with an overall transplant and/or mortality rate of 15% at 1 year. Patients who died or underwent transplant were older and had higher rates of hyperlipidemia, diabetes mellitus, atrial fibrillation, chronic kidney disease, advanced heart failure, ICD, CRT, lower EF, electrical storm (ES), shocks, amiodarone, and antiarrhythmic drugs. In the Cox multiple regression frailty analysis, transplant or death was associated with older age, NYHA class III and IV, chronic kidney disease, electrical storm, and use of hemodynamic support devices[42] (Table 7). The International Ventricular Tachycardia Center Collaborative Study Group registry of 2,061 patients who underwent VT ablation analyzed survival of patients 70 years with and without VT recurrence. Of 681 patients, 92% were men, 71% had ischemic VT, and 42% had VT storm at presentation. LVEF was 30±11%. Compared with patients <70 years, patients ≥70 years had higher 1-year mortality (15% versus 11%; P=0.002)[43] (Table 7). Patients with electrical storm are among the highest risk VT populations because they are frailer, older, with a lower LVEF, more advanced heart failure status, and more comorbidities. A comprehensive approach needs to include not only the arrhythmia ablation but also careful treatment of the comorbidities, such as advanced heart failure, hypertension, hyperlipidemia, atrial fibrillation, diabetes, and chronic kidney disease[44]. A major challenge of VT ablation is hemodynamic intolerance of the induced arrhythmia, with as few as 10% of induced arrhythmias being stable[45]. Extracorporeal membrane oxygenation (ECMO) will be increasingly used in this scenario[46]. The challenge is to predict a prohibitively high risk of not being able to wean the patient from VA-ECMO post-interventionally.

Outcomes in AdHF Patients Undergoing MCS/HTx

AdHF Patients Undergoing MCS.

MCS devices, originally used for patients with AdHF as a bridge-to-transplant or bridge-to-recovery, now increasingly used as destination (lifelong) therapy, have the potential to outnumber HTx by a factor of 1:10[47]. Because of this success, destination MCS is increasingly being offered to patients with challenging clinical profiles. There is significant patient-to-patient variability for risk of adverse events. Overall survival continues to remain >80% at 1 year and 70% at 2 years[48] (Table 7).

AdHF Patients Undergoing Heart Transplantation.

Since its first introduction in 1967, heart transplantation (HTx) offers an unparalleled survival benefit in select patients with stage D HF, and remains the gold standard of treatment. Stage D HF is defined as refractory HF and often accompanied by the following parameters: repeated (>2) hospitalizations or emergency department visits for HF in the past year, worsening renal function, unintentional weight loss>10% (cardiac cachexia), intolerance to medical therapy due to hypotension and/or worsening renal function, persistent dyspnea/fatigue, hyponatremia and escalating use of diuretics (>160 mg/d and/or use of supplemental metolazone therapy) and frequent ICD shocks.

Annually, there are approximately 3,000 HTx performed in the U.S. and the number of donors have remained steady for decades. Current graft survival rates with advances in immunosuppressive therapy are 85-90%, 75-80%, and 70-75% in adults at 1-, 3-, 5-year respectively, and a median survival of 11-13 years. Internationally, contemporary median survival after adult heart transplantation is 10.7 years[49] (Table 7).

ACC/AHA guidelines designates a class I indication for heart transplantation only in carefully selected patients with stage D HF despite GDMT, device, and surgical management. The leading cumulative causes of death are graft failure, infection, cancer, and multiple organ failure.

TABLE 7

Summary of AdHF-intervention studies with inclusion criteria, sample size and major outcomes: Across the different interventions, the 1-year mortality rate is in the range of 10-30%.

| Author (Year) | Inclusion | Patients | Intervention | Outcome/ Comments |
|---|---|---|---|---|
| Petrie 2016 | LVEF < 35% | 1,212 | CABG | >67 y equipoise GDMT vs CABG at 10 y |
| Holmes 2015 | STS7% | 12,182 | TAVR | 1 y mortality 23% |
| Leon 2010 | STS > 15-50% | 2,032 | TAVR | 1 y mortality 30% |
| Smith 2011 | STS > 10-15% | 699 | TAVR | 1 y mortality 24% |
| Leon 2016 | STS > 4-8% | 2,032 | TAVR | 1 y mortality 12% |
| Whitlow 2012 | STS ≥ 12 | 78 | Mitra-Clip | 1 y mortality 24% |
| Chiarito 2018 | LVEF39-59% | 2,615 | Mitra-Clip | 1 y mortality 16% |
| Tung 2015 | LVEF31% | 2,061 | VT-ablation | 1 y mortality 12% |
| Vakil 2017 | LVEF30%, >70 y | 681 | VT-ablation | 1 y mortality 15% |
| Vergara 2017 | LVEF34%, ES | 677 | VT-ablation | 1 y mortality 20% |
| Kirklin 2017 | LVEF low | 17,633 | MCS | 1 y mortality 20% |
| Lund 2017 | LVEF low | 21,614 | HTx | 1 y mortality 10-15% |

Abbreviations:
CABG—coronary artery bypass surgery;
GDMT—Guideline directed medical therapy;
LVEF—left ventricular ejection fraction;
HTx—Heart transplantation;
MCS—Mechanical circulatory support;
STS—Society of Thoracic Surgeons;
TAVR—Transcatheter Aortic Valve Replacement;
VT—Ventricular tachycardia;
Y—year Outcome Prediction Biomarker Prototype In our proof-of-principle outcome prediction biomarker prototype study described in Example 1, our central postulate is that OD and patient death after MCS- or HTx-surgery results from innate and adaptive immune cell dysfunction. Therefore, our goal was to use leukocyte immune-biology information to develop a preoperative test, which would precisely predict postoperative outcomes in the individual AdHF patient. We utilized the widely accepted SOFA[72] and MELD-XI [67,73,74] scores as quantitative assessment tools to interpret the PBMC data and to develop a predictive leukocyte biomarker. We specifically hypothesized that one of the most significant clinical outcome parameters for AdHF patients undergoing MCS is the probability of organ function improvement from one day before to eight days after surgery. Therefore, patients were grouped into two organ failure risk strata: Group I=improving (both SOFA and MELD-XI scores improve from day −1 to day 8) and Group II=not improving (SOFA and/or MELD-XI score(s) do not improve from day −1 to day 8). In other words, if the MCS-surgery improves the hemodynamic situation without complications, then the patient's organ function is expected to recover by postoperative day 5 and clearly by postoperative day 8, which should be reflected in a concordant improvement of SOFA and MELD-XI score, from day −1 to day 8. On the other hand, if SOFA or MELD-XI, or both, scores do not improve from day −1 to day 8, we hypothesize that this problem may potentially impact long-term survival. We hypothesized that in AdHF patients undergoing MCS-surgery, HF-related preoperative PBMC GEP correlate with and predict changes of early postoperative organ function status as surrogates for 1-year survival. Our studies showed the set of 28 identified genes [201] derived from preoperative PBMC GEP is predictive of early postoperative improvement or non-improvement of SOFA and MELD-XI scores. Out of the 28 preoperative genes, 12 genes were of specific biological interest due to their overlap in differentiating not only early postoperative organ function improvement but also year 1 survivor status[9].

Our data suggest that the pre-interventional dynamic recovery potential, rather than the static parameter of "severity of OD", is the key prognostic property to restoring equilibrium after surgery. This also presents the possibility of using a preoperative blood sample to identify AdHF-patients who may have a high chance of early postoperative recovery and a potentially good long-term prognosis. If the preoperative blood test result predicts a high FRP (Group I), this data might lead to the recommendation to undergo surgery. If the preoperative blood test suggests a low FRP (Group II), the healthcare team may avoid a potentially harmful recommendation of surgery at that time. In the US, we estimate that out of 30,000-60,000 individuals per year with AdHF and potential candidates for MCS and other AdHF-surgical/interventional therapies, at least 7,500-15,000 might not benefit from undergoing the intervention based on the test results if they are too sick at the time of testing. Since HF is a major public health concern due to its tremendous societal and economic burden, with estimated costs in the U.S. of $37.2 billion in 2009 and with expectations to increase to $97.0 billion by 2030, our proposed prediction test would simultaneously allow to tailor high-tech modern medicine to the individual patient's needs, i.e. optimize personal morbidity and mortality benefits and personal experience while also enhancing cost-effectiveness in U.S. healthcare. This concept would contribute to the advancement of high value-healthcare and reduction of low-value-healthcare.

It is important for the patient to choose the therapeutic option with the best short-, medium- and long-term outcome. In order to do so, the doctor needs to be able to predict, from pre-intervention data of the patient, what the consequences of the different options are. First and foremost, this means that all available pre-intervention data need to be analyzed for their long-term outcome prediction capacity. None of the current established clinical scoring and prediction tools integrate immune function parameters [53-59,61-69,72-74,162,163]. They have the tendency to be imprecisely calibrated in estimating risk among severely ill patients [60,61], making the therapeutic recommendation with the best survival estimate for the individual patient very difficult. Therefore, we intend to develop a molecular blood test that predicts, from pre-intervention data, recovery of organ function and frailty reversal, which, in turn, predict 1-year survival. This information will help tackle the following challenge for the individual patient and doctor: We describe a molecular blood test, based on a PBMC GEP sample taken 1-3(7) days before undergoing surgical/interventional therapies for AdHF, that can assist clinicians in more precisely diagnosing FRP, i.e. predicting FR, as a surrogate marker for 1-year survival and help the patient and clinician in the shared-decision making process to choose the most meaningful treatment option.

Clinical Validity Study

We plan to complete a FDA-clearance Pivotal Trial with ≥1,000 AdHF patients, stratified for four primary HF-mechanisms (ischemic, overload, arrhythmia, dyscontractility). After completion of a clinical validity study of developing the test in a framework of diagnosing the potential of future organ function recovery and frailty reversal, FDA-clearance and clinical implementation, we plan to conduct a clinical utility trial, testing the impact of adding the test information to the best current clinical prediction tools of net health outcomes as we did with the AlloMAP™ test development[164-166]. We plan to make this test commercially available, likely using the Nanostring platform that has already been used for an FDA-cleared In-vitro-Diagnostic Multivariate Index Assay test[167].

Biomarkers in the Practice of Shared Decision-Making

It is critical to have a multidisciplinary heart team to provide expertise to make the best recommendation regarding the individual patient's anticipated benefit [168]. It is important for these teams to get comfortable with the decision to not pursue the most aggressive option available in patients for whom the anticipated benefits do not outweigh the risks. The decision not to offer specific AdHF-surgical/interventional therapies should not be equated with abandoning care [169]. Shared decision-making requires both the patient and the provider to share information, work toward a consensus, and reach agreement on the course of action[170] consistent with the patient's preferences[171-173]. As we work on technological innovations to improve the devices, we must also use it responsibly within a framework of care that enables shared decision making and promotes patient goals and well-being [169].

Future Perspectives

We will tailor the molecular test precision medicine results to a high quality Relational Medicine [174] encounter to maximize its effectiveness. The clinical decision-making challenge at the time of AdHF evaluation often culminates in the choice between everything modern medicine has to offer and compassionate end of life care. This ultimate scenario is medically, ethically, and economically demanding. It deserves the best evidence-based decision making support that personalized precision medicine research has to offer in order to live up to the highest humanistic expectations that society entrusts us with.

Over the next decade, this vision of a meaningful practice of modern medicine will increasingly incorporate the elements of molecular precision medicine with Relational Medicine, promoting high value healthcare over low value healthcare. The monetary have all been implemented in the US-healthcare system and are already taking effect. In order to achieve these goals, future generations of healthcare professionals will be trained to pursue a practice that allows them to achieve these goals.

References cited in this Example can be found in Deng, M. C., 2018 Biomarkers in Medicine Vol. 12(6).

Example 3: Case Studies Show Predictive Value of FRP Scoring

Figure 8:
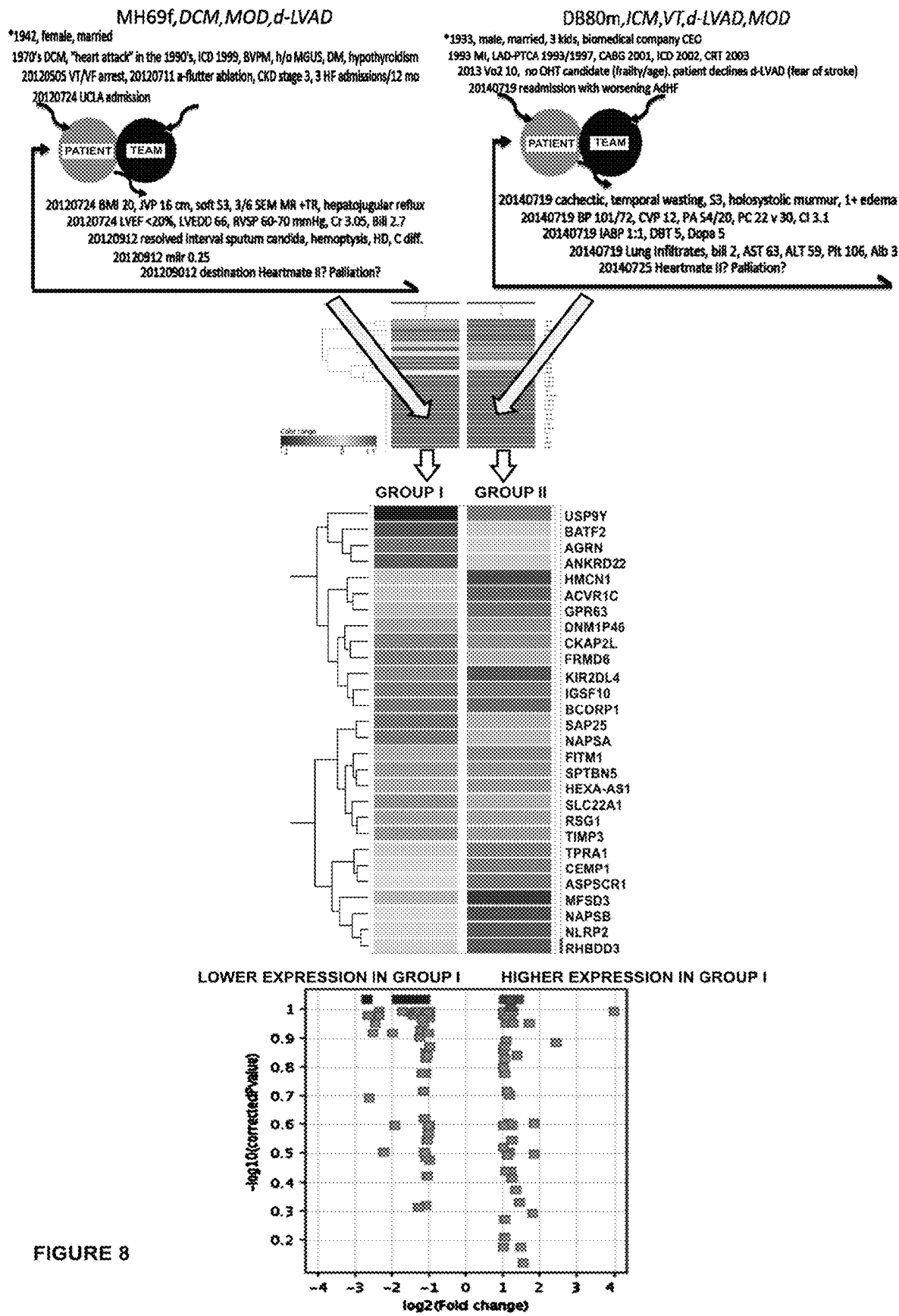
FIG. 8 shows two case studies out of the 29 AdHF-patients in the Proof-Of-Concept Study that illustrate the clinical utility of FRP scoring. The indicated color range corresponds to the differential expression, ranging from blue (−2) to gray, to yellow (0), to orange, to red (1.1).

This Example demonstrates the advantages achieved using the predictive value of the FRP scoring. Two case studies out of the 29 AdHF-patients in the Proof-Of-Concept Study illustrate the clinical utility of FRP scoring. Case Study #1 (FIG. 8): MH, a 69-year-old woman, born in 1942, married, who was in the 1970's diagnosed with Dilated Cardiomyopathy, had a "heart attack" in the 1990's, underwent Implantable Cardioverter-Defibrillator (ICD) implantation and Biventricular Pacemaker Implantation (BVPM) 1999, had a history of Monoclonal Gammopathy of Unknown Significance (MGUS), Diabetes Mellitus (DM) and hypothyroidism. In 2012, she suffered a cardiac arrest, developed renal dysfunction and was hospitalized three times in 12 months for heart failure decompensation. In July 2012, she was admitted to UCLA in cardiogenic shock and multiorgan dysfunction (liver, kidneys, lung, immune system). The AdHF-team was uncertain, but felt that she was likely approaching end-of-life, and had only a very small chance of reversing her organ dysfunction in order to be evaluated for advanced heart failure therapies such as MCS or Htx. In contrast to this assessment, the patient recovered, was eventually being evaluated, six weeks later underwent destination Heartmate II Left Ventricular Assist Device (LVAD) implantation and lived a very active life with her husband thereafter for >5 years. Her preoperative PBMC-GEP (left arrow in Figure) would have indicated—with an accuracy of 93%—a high FRP and therefore high long-term (1-year) survival probability and would have supported a proactive strategy recommending an earlier LVAD-surgery timepoint to the patient. However, this patient's test results were not available at the time of shared decision-making.

Case Study #2 (FIG. 8): DB, an 80-year-old man, born in 1933, married, 3 kids, biomedical company Ex-CEO, in 1993 suffered a large myocardial infarction (MI), underwent LAD-PTCA 1993/1997, CABG 2001, ICD 2002, and BVPM 2003. In 2013, his cardiopulmonary exercise capacity was reduced to 10 ml/kg/min, and he was evaluated for AdHF-therapy options. Since he was not a HTx candidate (frailty/age 80), he was offered destination-MCS at UCLA. The patient declined LVAD-surgery for fear of a 10% stroke risk. In July 2014, he was transferred to UCLA from an outside hospital on intra-aortic balloon pump (IABP), having become more cachectic with temporal wasting, impending renal and hepatic failure, as well as pneumonia. While the patient now requested destination-LVAD implantation, the AdHF-team was uncertain, but felt that the patient was possibly too sick for surgery. Ultimately, the team went ahead, implanted the destination Heartmate II LVAD, and the patient died 6 weeks later on the respirator and on dialysis on multiorgan failure in the Cardiothoracic Intensive Care Unit (CTICU). His preoperative PBMC-GEP (right arrow in Figure) would have indicated—with an accuracy of 93%—a low FRP and therefore low long-term (1-year) survival probability, and would have supported a palliative strategy, recommending discharge home to allow a dignified dying process in the context of the patient's family. However, this patient's FRP test results were not available at the time of shared decision-making.

Example 4: Treatment of Heart Failure

An individual presents with clinical symptoms of heart failure including shortness of breath, excessive tiredness, and leg swelling. It is determined that the individual has heart failure via diagnostic tests including echocardiography, blood tests, electrocardiography, and chest radiography. A blood sample is obtained from the individual and PBMCs are isolated from the blood sample. RNA is isolated from the isolated PBMCs and subjected to Nanostring analysis to measure gene expression of RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, and FITM1. The gene expression levels are determined to be elevated or reduced for each of these genes and a FRP score is calculated based on these gene expression levels. It is determined that the individual as an FRP score of less than 5 and is therefore referred for optimal medical management (OMM) and/or palliative care (PC).

A second individual presents with clinical symptoms of heart failure and diagnostic tests confirm that the individual has heart failure. A blood sample is obtained from the individual and PBMCs are isolated from the blood sample. RNA is isolated from the PBMCs and subjected to Nanostring analysis to measure gene expression of RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, and FITM1. The gene expression levels are determined to be elevated or reduced for each of these genes and a FRP score is calculated based on these gene expression levels. It is determined that the individual as an FRP score of 7 and is therefore referred for treatment with mechanical circulatory support (MCS) surgery. The individual survives the surgery and the symptoms of heart failure are reduced.

Example 5: Systems Biological Identification of an Age-Related Predictor of Functional Recovery Potential in Advanced Heart Failure This Example demonstrates that FRP can be improved by additional clinical and age-related transcriptome data. The Example shows that, in AdHF patients, a model obtained from preoperative data that incorporates clinical and genomic parameters including genes related to chronological age has the ability to predict Group I/II outcomes after MCS surgery. This correlates with long-term outcomes lending itself to outcome prediction beyond recovery from surgery.

From the study with 29 patients undergoing mechanical circulatory support (MCS) surgery, FRP was defined by grouping patients into two clinically relevant organ failure risk strata: Group I=IMPROVING (SOFA and MELD-XI scores both improve from day −1 to day 8) and Group II=NOT IMPROVING (SOFA and/or MELD-XI score(s) do not improve from day −1 to day 8). Peripheral blood mononuclear cell (PBMC) samples were collected one day before surgery (day −1). Clinical data was collected on day −1 and day 8 postoperatively. Purified mRNA was subjected to whole-genome Next-Generation Sequencing (NGS) analysis. Correlation analyses were performed using NGS Strand. Two groups were created by age (60 y): Age A (<60 y, n=13), Age B (≥60 y, n=16). A model was built using the following strategy: Step 1: Clinical model using multivariate logistic regression, Step 2: Transcriptomics model using support vector machine (28 genes transcriptome differentially expressed between Group I/Group II (Step 2A) and 12 genes based on biological age (Step 2B), and Step 3: Combined Model. This model prediction was proposed to optimize the clinical and transcriptome model.

Out of 29 AdHF-patients undergoing MCS-surgery, 17 patients improved (Group I) while 12 patients did not (Group II). Older patients were more likely in Group II, i.e. Age B=10/16 (62%) and Age A=2/13 (15%). One-year survival in Group Age I was 10/13 (77%) and in Group Age II 8/15 (53%).

The Clinical model, using all clinical parameters as input, identified respiratory rate, chronological age and white blood cell count as the best clinical combination (cross validation accuracy 82%) to predict Group I vs Group II. The Transcriptomics model, consisting of the 28 previously identified genes (Step 2A) (accuracy 93%) and adding 12 age-related genes (Step 2B) (derived from a sub-cohort analysis of older male patients) increased the accuracy of prediction model to 94%. To optimize the accuracy of prediction, the clinical and transcriptomic models were combined to create the Combinatorial Model (accuracy 96%).

Bondar et al., 2017, PLoS One December 13; 12(12) (see Table 1 therein) summarizes the demographics and key clinical data, which can be sorted by age grouping. NICM=nonischemic dilated cardiomyopathy, PPCM=peripartum cardiomyopathy, ICM=ischemic cardiomyopathy, ChemoCM=chemotherapy-induced cardiomyopathy, HM II=Heartmate II, CMAG=Centrimag, LVAD=Left ventricular assist device, RVAD=right ventricular assist device, BVAD=biventricular assist device, HVAD=Heartware LVAD, TAH=Total Artificial Heart, ECMO=extracorporeal membrane oxygenator, GROUP: Organ function changes of SOFA-score and MELD-XI score from preoperative day −1 (TP1) to postoperative day 8 (TP5) (Group I=WHITE ROWS=Improvement vs. Group II=GREY ROWS=No improvement.

FIG. 3A summarizes the individual patients' organ function improvement and 1-year survival trajectory (discussed further in Example 1 above). SOFA and MELD-XI across five time points (TP) grouped by age (Age A, <60 y, Age B, ≥60 y). Each black line represents one 1-year survivor while each red line represents one 1-year non-survivor. FIG. 4 shows Kaplan-Meier 1-year survival in Age B vs. Age A. The time-to-event Kaplan-Meier survival analysis suggested a trend of elevated risk of death (log rank test p=0.12) in older patients (Age B) continued over a 3-6 month period following MCS-surgery.

Table 8 summarizes role of clinical parameters in prediction of FRP. RR-Respiratory Rate; HR-Heart Rate; WBC-White Blood Cell; CB-Serum Creatinine (mg/dl); and AIC-Akaike information criterion. The total number of samples were 29. The multivariate Regression analysis model was built on 24 samples and tested on the remaining 5 samples.

TABLE 8

Clinical model building for Group I vs. II membership prediction using multivariate logistic regression

| Clinical Variables | Variable Removed | P-value for Variable Removed | AIC |
|---|---|---|---|
| RR, Age, Sofa Score, HR, WBC, CB, Glucose | Full model | — | 21.42 |
| RR, Age, Sofa Score, HR, WBC, CB | Glucose | 0.8402 | 19.44 |
| RR, Age, Sofa Score, WBC, CB | Heart Rate | 0.33447 | 18.87 |
| RR, Age, Sofa Score, WBC | Sofa Score | 0.34133 | 18.29 |
| RR, Age, WBC | CB | 0.9336 | 17.47 |

The prediction model was enhanced using the combinatorial model. To optimize the clinical and transcriptomics model, we combined respiratory rate, chronological age, and White Blood Cell, the 28 genes associated with Group I/II (Bondar 2017) and the 12 genes associated with biological age. This model increased accuracy of Group I/II prediction to 96%.

Example 6: Centralized Testing and Assigning Treatment Regimen

A preserved blood sample is received from a clinician treating an individual who has been diagnosed with heart failure. RNA is isolated from the blood and subjected to Nanostring analysis to measure gene expression of RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, and FITM1. The gene expression levels are determined to be elevated or reduced for each of these genes and a FRP score is calculated based on these gene expression levels. The FRP score of less than 5 is reported to the clinician with a recommendation for optimal medical management (OMM) and/or palliative care (PC).

Another preserved blood sample is received from a clinician treating an individual who has been diagnosed with heart failure. RNA is isolated from the blood and subjected to NanoString analysis to measure gene expression of RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, and FITM1. The gene expression levels are determined to be elevated or reduced for each of these genes and a FRP score is calculated based on these gene expression levels. The FRP score of 7 is reported to the clinician with a recommendation for treatment with mechanical circulatory support (MCS) surgery.

Example 7: Kit for Determining Treatment Regimen for Heart Failure

An individual presents with clinical symptoms of heart failure including shortness of breath, excessive tiredness, and leg swelling. It is determined that the individual has heart failure via diagnostic tests including echocardiography, blood tests, electrocardiography, and chest radiography. A blood sample is obtained from the individual and PBMCs are isolated from the blood sample. A kit is obtained for isolating RNA is the isolated PBMCs. The kit also contains reagents for Nanostring analysis to measure gene expression of RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, and FITM1. The kit includes software to determine that the gene expression levels are elevated or reduced for each of these genes and a FRP score is calculated by the software based on these gene expression levels. The software assigns to the individual an FRP score of less than 5 and recommends optimal medical management (OMM) and/or palliative care (PC).

A second individual presents with clinical symptoms of heart failure and diagnostic tests confirm that the individual has heart failure. A blood sample is obtained from the individual and PBMCs are isolated from the blood sample. A kit is obtained for isolating RNA is the isolated PBMCs. The kit also contains reagents for Nanostring analysis to measure gene expression of RSG1, TPRA1, SAP25, MFSD3, FITM1, SPTBN5, CEMP1, ASPSCR1, NAPSB, NAPSA, NLRP2, RHBDD3, FRMD6, TIMP3, ACVR1C, DNM1P46, KIR2DL4, USP9Y, ANKRD22, BCORP1, HMCN1, GPR63, BATF2, SLC22A1, AGRN, CKAP2L, IGSF10, HEXA-AS1, LOC728431, PDZK1IP1, NEGR1, KCNH8, CCR8, MME, ETV5, CXCL9, HBEGF, RANBP17, DDX43, C6orf164, C7orf50, NEFL, CDCA2, ALDH1A1, OLFM1, FADS3, SAC3D1, FZD4, RBPMS2, C15orf38, ST6GALNAC1, CHMP6, SKA1, CD209, SNAPC2, AXL, KIR2DL1, NTSR1, SEPT5, KAL1, PRRG1, XIST, RPS4Y1, ZFY, PRKY, TTTY15, DDX3Y, UTY, TXLNG2P, KDM5D, EIF1AY, and FITM1. The kit includes software to determine that the gene expression levels are elevated or reduced for each of these genes and a FRP score is calculated by the software based on these gene expression levels. The software assigns to the individual an FRP score of 7 and recommends treatment with mechanical circulatory support (MCS) surgery. The individual survives the surgery and the symptoms of heart failure are reduced.

Throughout this application various publications are referenced. The disclosures of these publications in their entireties are hereby incorporated by reference into this application in order to describe more fully the state of the art to which this invention pertains.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for treating an individual, comprising:
   (i) receiving a sample from the individual;
   (ii) determining a gene expression level in the sample for DNM1P46 and at least one gene comprising SAP25, NAPSA, RHBDD3, FRMD6, TIMP3, KIR2DL4, ANKRD22, BCORP1, BATF2, AGRN, or HEXA-AS1;
   (iii) determining, based on the gene expression level, a survival outcome probability for the individual wherein the determined survival outcome probability is the probability of post-operative survival following an interventional treatment or a surgical treatment;
   (iv) treating the individual with the interventional treatment or the surgical treatment when there is an indication to do so based on the determined survival outcome probability for the individual; and
   (v) treating the individual with a palliative treatment or a medical management when there is an indication to do so based on the determined survival outcome probability for the individual,
   wherein the interventional treatment, the surgical treatment, the palliative treatment, and the medical management treat organ failure in the individual.

2. The method of claim 1, wherein the sample comprises blood, urine, sputum, hair, or skin.

3. The method of claim 1, wherein the gene expression level is either an increase or a decrease in expression of the at least one gene relative to an expected expression level value.

4. The method of claim 1, wherein the gene expression level is assigned a score, and wherein the survival outcome probability is based on the score.

5. The method of claim 4, wherein the score comprises a Function Recovery Potential (FRP) score.

6. The method of claim 5, wherein the score is determined based on a linear discriminant analysis of data comprising known gene expression levels and known FRP scores of a plurality of individuals.

7. The method of claim 6, wherein the interventional treatment and surgical treatment are selected from mechanical circulatory support (MCS) surgery, heart transplant (HTx) surgery, coronary artery bypass graft (CABG) surgery, percutaneous coronary interventions (PCI), aortic valve replacement (AVR) surgery, mitral valve replacement (MVR) surgery, trans-catheter aortic valve replacement (TAVR), transcatheter mitral clip, ventricular tachycardia ablation, or stellate gangliectomy.

8. The method of claim 6, wherein the gene expression level is a level determined by polymerase chain reaction (PCR), next generation sequencing (NGS), or other gene expression assay platform.

9. The method of claim 8, wherein the PCR is performed using at least one primer selected from GAPDH-f: CCACTCCTCCACCTTTGAC (SEQ ID NO: 1); GAPDH-r: ACCCTGTTGCTGTAGCCA (SEQ ID NO: 2); KIR2DL4-f: ACCCACTGCCTGTTTCTGTC (SEQ ID NO: 3); KIR2DL4-r: ATCACAG-CATGCAGGTGTCT (SEQ ID NO: 4); NAPSA-f: CAGGACACCTGGGTTCACAC (SEQ ID NO: 5); NAPSA-r: GGTTGGACTCGATGAAGAGG (SEQ ID NO: 6); BATF2-f: AAAGGCAGCTGAAGAAGCAG (SEQ ID NO: 7); BATF2-r: TCTTTTTCCAGAGACTCGTGC (SEQ ID NO: 8); ANKRD22-f: CTCAGCCAGGAAGGATTTTG (SEQ ID NO: 9); ANKRD22-r: TGATAGGCTGCTTGGCA-GAT (SEQ ID NO: 10).

10. The method of claim 1, wherein the organ failure comprises a liver disease.

11. The method of claim 10, wherein the interventional treatment or the surgical treatment is liver surgery or a liver transplant.

12. The method of claim 1, wherein the medical management comprises a guideline directed medical treatment.

13. The method of claim 1, wherein the individual is suffering from kidney disease.

14. The method of claim 13, wherein the interventional treatment or the surgical treatment is kidney surgery or a kidney transplant.

15. The method of claim 13, wherein the medical management comprises guideline directed medical treatment or dialysis.

16. The method of claim 1, wherein the individual is suffering from lung disease.

17. The method of claim 16, wherein the interventional treatment or the surgical treatment is lung surgery or lung transplant.

18. The method of claim 16, wherein the medical management comprises guideline directed medical treatment or ventilator therapy.

19. The method of claim 1, wherein the individual is suffering from sepsis.

20. The method of claim 19, wherein the medical management comprises guideline directed medical treatment or ventilator therapy.

* * * * *

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
ccactcctcc acctttgac                                                19

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
accctgttgc tgtagcca                                                 18

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
acccactgcc tgtttctgtc                                               20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
atcacagcat gcaggtgtct                                               20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
caggacacct gggttcacac                                               20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ggttggactc gatgaagagg                                               20

<210> SEQ ID NO 7
<211> LENGTH: 20
<212> TYPE: DNA
<213> ORGANISM: Artificial Sequence
```

```
<220> FEATURE:
<223> OTHER INFORMATION: primer

<400> SEQUENCE: 7
aaaggcagct gaagaagcag                                      20

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8 tcttttttcca gagactcgtg c                                   21

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
ctcagccagg aaggattttg                                      20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tgataggctg cttggcagat                                      20
```